(12) United States Patent
Meruelo et al.

(10) Patent No.: US 7,071,301 B1
(45) Date of Patent: Jul. 4, 2006

(54) CHIMERIC VIRAL RECEPTOR POLYPEPTIDES, HUMAN VIRAL RECEPTOR POLYPEPTIDES AND USES THEREOF

(75) Inventors: Daniel Meruelo, Scarborough, NY (US); Takayuki Yoshimoto, Tokyo (JP)

(73) Assignee: New York University, New York, NY (US)

( * ) Notice: Subject to any disclaimer, the term of this patent is extended or adjusted under 35 U.S.C. 154(b) by 0 days.

(21) Appl. No.: 08/912,332

(22) Filed: Aug. 18, 1997

Related U.S. Application Data

(63) Continuation-in-part of application No. 08/084,729, filed on Jun. 29, 1993, now abandoned, which is a continuation-in-part of application No. PCT/US93/05569, filed on Jun. 11, 1993, which is a continuation-in-part of application No. 07/899,075, filed on Jun. 11, 1992, now abandoned, which is a continuation-in-part of application No. 07/806,178, filed on Dec. 13, 1991, now abandoned, and a continuation-in-part of application No. 07/627,950, filed on Dec. 14, 1990, now abandoned.

(51) Int. Cl.
*C07K 14/705* (2006.01)
*C07K 14/435* (2006.01)

(52) U.S. Cl. .................. 530/350; 530/387.3; 530/388.3
(58) Field of Classification Search .................. 530/350, 530/387.3, 388.3
See application file for complete search history.

(56) References Cited

PUBLICATIONS

Etienne–Julan et al., Bone Marrow Transplantation, vol. 9, Supplement 1, Jan. 5–8, 1992, 139–143.*

Albritton et al., Cell, vol. 57, 659–666, May 19, 1989.*

* cited by examiner

*Primary Examiner*—Mary E. Mosher
(74) *Attorney, Agent, or Firm*—Darby & Darby

(57) ABSTRACT

Target cell specificity of delivery vectors is provided by incorporation of a target cell specific binding domain by the use of any binding domain, which binds specifically to a binding site on the target cell. The binding site may be endogenous to the target cell, provided by engineering the target cell, or a suitable binding site may be associated with the target cell. Target cell may also be associated with a CVR polypeptide to provide specificity for the delivery vector. The association of the CVR polypeptide confers target cell specificity for a second virus host cell range, which specificity differs from the viral host cell range of the endogeneous target cell or animal host cell viral receptors. The CVR polypeptide may thus comprise a chimeric virus binding site which binds a second virus env binding domain specific for a second virus host cell range, selected from at least one of the group consisting of amphotropic, polytropic, xenotropic, ecotropic and tissue specific.

6 Claims, 28 Drawing Sheets

FIG. 1A

NUCLEOTIDE AND DEDUCED AMINO ACID SEQUENCES OF H13 cDNA

```
1081 ATGCCCTACTTCTGCCTGGACAATAACAGCCCCCTGCCCGACGCCTTTAAGCACGTGGGCTGGGAAGGTGCCAAGTACGCAGTGGCCGTG
      M  P  Y  F  C  L  D  N  N  S  P  L  P  D  A  F  K  H  V  G  W  E  G  A  K  Y  A  V  A  V      341
1171 GGCTCCCTCTGCGCTCTTCCGCAGTCTTCTAGGTCCATGTTCCCATGCCTCGGGTTATCTATGCCAATGGCTGAGGATGGACTGCTA
      G  S  L  C  A  L  S  L  L  G  S  M  F  P  M  P  R  V  I  Y  A  M  A  E  D  G  L  L           371
1261 TTTAAATTCTTAGCCAACGTCAATGATAGGACCAAATGCCACTCTCCTGGCTACTCGTTGGTGGCTGCCTGTGTGTTGGTCTTACGG
      F  K  F  L  A  N  V  N  D  R  T  K  T  P  I  A  T  L  A  S  G  A  V  A  A  V  M  A  F      401
1351 CTCTTTGACCTGAAGGACTTGGTGGACCTCATGTCCATTGGGACCCTCCTGGCCTACTCGTTGGTGGCTTGTGTTGGTCTTACGG
      L  F  D  L  K  D  L  V  D  L  M  S  I  G  T  L  L  A  Y  S  L  V  A  C  V  L  V  L  R      431
1441 TACCAGCCAGAGCAGCCTAACCTGGTATACCAGATGGCCAGTACTTCCGACGAGTTAGATCCAGCAGACCAAAATGAATTGGCAAGCACC
      Y  Q  P  E  Q  P  N  L  V  Y  Q  M  A  S  T  S  D  E  L  D  P  A  D  Q  N  E  L  A  S  T  461
1531 AATGATTCCCAGCTGGGGTTTTACCAGGAGGCAGAGATGTTCTCTTTGAAAACATGGAGCCTTCCAAAATCCAAAATC
      N  D  S  Q  L  G  F  L  P  E  A  E  M  F  S  L  K  T  I  L  S  P  K  N  M  E  P  S  K  I    491
1621 TCTGGGCTAATTGTGAACATTTCAACCAGCCTTATAGCTGTTCTCATCATCACCTTCTGTATTGTGACCGTGCTTGGAAGGGAGGCTCTC
      S  G  L  I  V  N  I  S  T  S  L  I  A  V  L  I  T  F  C  I  V  T  V  L  G  R  E  A  L      521
1711 ACCAAAGGGGCGCTAGAGAGCTCTCATTAAGGTTCCTGCCAGTGCTCCCCATCGTGAACGTATCTCATGATGCAGCTG
      T  K  G  A  L  W  A  V  F  L  L  A  G  S  A  L  L  C  A  V  V  T  G  V  I  W  R  Q  P  E  551
1801 AGCAAGACCAAGCTCTCATTAAGGTTCCTGCCAGTGCTCCCCATCCTGTCCATCATCTACTTTGGCTATGGCCTGTGGCACAGCGAGGAAGCCG
      S  K  T  K  L  S  F  K  V  P  F  L  P  V  L  P  I  L  S  I  F  V  N  V  Y  L  M  Q  L      581
1891 GACCAGGGCACCTGGGTCCGGTTTGCTGTGTGATGCTGATAGGCTTCATCATCTACTTTGGCTATGGCCTGTGGCACAGCGAGGAAGCCG
      D  Q  G  T  W  V  R  F  A  V  W  M  L  I  G  F  I  I  Y  F  G  Y  G  L  W  H  S  E  E  A  611
1981 TCCCTGGATGCCGACCAAGCAACTTGACGCAACTGGACGCAGTGCAACTTGACGTGCAACAGTGACGACGCAGCAGCCCCGCCCCCGGAGGTGGCAGCAGC
      S  L  D  A  D  Q  A  R  T  P  D  G  N  L  D  Q  C  K  *                                    629
2071 CCGAGGGACGCCCCAGAGAGGACCGGGAGGGCACCCCACCCCTGCGTCCACACCCTCACTGCA
```

FIG. 1B

NUCLEOTIDE AND DEDUCED AMINO ACID SEQUENCES OF H13 cDNA

```
1081 ATGCCCTACTTCTGCCTGGACAATAACAGCCCCCTGCCCGACGCCTTTAAGCACGTGGGCTGGGAAGGTGCCAAGTACGCAGTGGCCGTG
      M  P  Y  F  C  L  D  N  N  S  P  L  P  D  A  F  K  H  V  G  W  E  G  A  K  Y  A  V  A  V    341
1171 GGCTCCCTCTGCGCTCTTAGTCTCCTAGTCTCTTCCGCCAGTCTTCTAGGTTCCATGCCCATGCCTCGGGTTATCTATGCCGAGGACTGCTA
      G  S  L  C  A  L  S  L  L  G  S  M  F  P  M  P  R  V  I  Y  A  M  A  E  D  G  L  L       371
1261 TTTAAATTCTAGCCAACGTCAATGATAGGACCAAAACATCATTGGCACTCTCCTGGCTTACTCGTTGGTGCTGTTGGTCTTACGG
      F  K  F  L  A  N  V  N  D  R  T  K  T  P  I  A  T  L  A  S  G  A  V  A  V  M  A  F       401
1351 CTCTTTGACCTGAAGGACTTGGTGGACCTCATGTCCATTGGCACTCTCCTGGCTTACTCGTTGGTGCTGTTGGTCTTACGG
      L  F  D  L  K  D  L  V  D  L  M  S  I  G  T  L  L  A  Y  S  L  V  A  C  V  L  V  L  R    431
1441 TACCAGCCAGAGCAGCCTAACCTGGTATACCAGATGGCCAGTACTTCCGACGAGTTAGATCCAGCAGACAACGAACTGGCAAGCACC
      Y  Q  P  E  Q  P  N  L  V  Y  Q  M  A  S  T  S  D  E  L  D  P  A  D  Q  N  E  L  A  S  T  461
1531 AATGATTCCCAGCTGGGCGTCTTGTGGGCAGTCTTTCTGCTCGCGGCAGTCTTCCTGCTCGCTGGTGGTCACGGGCGTCATCTGGAGGCCCGAG
      N  D  S  Q  L  G  F  L  P  E  A  E  M  F  S  L  K  T  I  L  S  P  K  N  M  E  P  S  K  I  491
1621 TCTGGGCTAATTGTGAACATTTGTGAACAGCTCTTATAGCGTCTCATCATCACCTTCTGCATTGTGACCGTTGGAAGGGAGGCTCTC
      S  G  L  I  V  N  I  S  T  S  L  I  A  V  L  I  I  T  F  C  I  V  T  V  L  G  R  E  A  L  521
1711 ACCAAAGGGGCGCTGTGGGCAGTCTTTCTGCTCGCGGCAGTCTTCCTGCTCGCAGTCCCCATCCTGAGCATCTTGTGAACGTCTATCTCATGATGCAGCTG
      T  K  G  A  L  W  A  V  F  L  L  A  G  S  A  L  L  C  A  V  V  T  G  V  I  W  R  Q  P  E  551
1801 AGCAAGACCAAGCTCTCATTTAAGGTTCCCTTCCTGCCAGTGCTCCCCATCCTGAGCATCTTGTGAACGTCTATCTCATGATGCAGCTG
      S  K  T  K  L  S  F  K  V  P  F  L  P  V  L  P  I  L  S  I  F  V  N  V  Y  L  M  M  Q  L  581
1891 GACCAGGGGACCTGGACTGCGACCAAGCAACTTGGATGCCAACTTGGACGCCAACTTGACGACACAGAAACCACCTGTTGGCAGCAGC
      D  Q  G  T  W  V  R  F  A  V  W  M  L  I  G  F  I  I  Y  F  G  Y  G  L  W  H  S  E  E  A  611
1981 TCCCTGGATGCCGACCAAGCAACTTGGATGCCAACTTGACGACACAGAAACCACCTGTCCCCACACCCTCACTGCA
      S  L  D  A  D  Q  A  R  T  P  D  G  N  L  D  Q  C  K  *                                   629
2071 CCCGAGGGACGCCCCCAGAGGACCGGGAGGCACCCTCCCCACACCCTGCTCCACACCCTCACTGCA
```

FIG. 2A(1)

```
H13    1                              CGATCCTGCCGGAGCCCCGC....CGCCGCCGGCTTGGATTCTGAAACCTTCCTTGTATCCCT    59
                                      ||| ||||      ||||||    ||||| || || ||||| ||  |||| ||  || |||
ERR   51   CTACCCGCGGGTCTCCACACAGCTCAACATCTTGCCGAGCCTGAAGCTACCGTGG..ACTCT                118

H13   60   CCTGAGACATCTTGCTGCAGATCGAGGCTGTCCTCTGGTGAGAAGGTGGTGAGGCTTCCGTGAGGCTTCCGTCATATT  129
           |||  |  |||| |||    ||| |   |||   | ||  | ||  |   ||  ||    |||||  || |
ERR  119   GCTGTGGCGTCTTGGCCCCCAGGT.GCGGATCCTCCCCAGTGAGAAG........TCCCACGAGTCTTACA        180

H13  130   CCAGCTCTGAACAGCAACATGGGGGTGCAAAGTCCTCAACATTGGGCAGCAGATGCTGCGGCGGAAGG            199
           ||||  |   ||  | |   ||| |      |||| |   ||  ||  |   || ||  | | ||||
ERR  181   GCAGATTCGCTCAGCACAATGGGCTGCAAAAACCTGCTCGGTCTCGGCCTGAACACTTTGATCTGGATTGGCCCCTCGG  250

H13  200   TGGTGGACTGTAGCCGGGAGGAGACGCGGCTGGTGTCTTACGTCCTGGCTGGGAGCTGTGGCCCGTGAGAATGCAGGCCCT  269
           |||||||||| ||| ||  |||| | |  ||| | |  | |||||||| |  ||  ||||  |||||  ||| ||| |||
ERR  251   TGGTGGACTGCAGCCGGCACGGAGAGCCGGCTGGTGCTCAACACCTCAACACCTAGCCTGGTGCTGGGACCTGGGCCCCTT  320

H13  270   GGTGGGCAGCAGACACTGGGTGCTGGGTTCTACGTCCTGGGCCCTGAGTCCTGGAGCTGGCTGTGTCCTATGGCGAGTTTG  339
           |||||||||||| || ||||  || || | | | |||| ||||| ||  |||| |||| ||| | | |  | ||||  |
ERR  321   TGGTGGGCAGCAGCACCTTGGGACGCTGGTGTCTATGTCCTGGGCCCTGGTGCTGGACCTGGCTGTGTCTAGGCGGAGTTTG  390

H13  340   GCCATTGTCATCTCCTTCCTGATCGCTGGCCTCAGTGCTGCTGGCTGTGCTATGGCGAGTTTG                 409
           |||||||||||| ||| |||| || |||  || | ||| | |||||| ||| | |  |
ERR  391   GCCATGGTCATCTCCTTCTTGATTGCTGGTCTGCTGCCTCTCGGCCTCGGCTGTGCTACGGCGAGTTTG            460

H13  410   GTGCTCGGGGTCCCCAAGACGGGGCTCAGCTTACCTCTACAGCTATGTCACCGTGGAGAGAGCTCTGGGCCTT         479
           |||| ||| |||  |||| |||||||||||||| |||||||||||| ||  ||| || |||||||||   |||
ERR  461   GTGCCCGGTGTCCCCAAGACGGGGCTCAGCTTACCTCTACAGCTACGTGAGCGTGGGGGAGCTTGGGCCTT          530
```

FIG. 2A(2)

```
H13  480 CATCACCGGCTGGAACTTAATCCTCCTACATCATCGGTACTTCAAGCGTAGCGAGGGCCTGGAGCGCC  549
         ||||||||||||||||||| || ||| ||||||||||||||||||||| || ||| || ||||||||
ERR  531 CATCACTGGCTGGAACCTGATTCTCCTACATCGGTACTTCAAGCGTGGCAAGAGCCTGGAGTGCG   600

H13  550 ACCTTCGACGAGCTGATAGGCAGACCCATCGGGGAGTTCTCACGGACACACATGACTCTGAACGCCCCG  619
         |||||||||| ||||||| ||  |||||||  || |||||| | ||| |||||||| ||||| || |
ERR  601 ACTTTGACGAGCTGATAGGCCAAGCCCATGGGAGAGTTCTCACGTCAGCAGCACATGGCCCTGAATGCTCCTG  670

H13  620 GCGTGCTGGCTGAAAACCCCGACATATTCGCAGTGATCATAATTCTCATCTTGACAGGACTTTTAACTCT  689
         |||||||| |    ||||  |||  ||| ||| |||||||||| |||| |||| ||||||| ||||||
ERR  671 GGGTGCTGGCCCAAACCCCGGACATATTTGCAGTGATCAAAATTATAATTATCATCTTAACAGGACTGTTAACTCT  740

H13  690 TGGTGAAAGAGTCGGCCATGGTCAACAAAATATTCACTTGTATTAACGTCCTGGTCCTGGGCTTCATA  759
         ||  || ||||| || |||| |||||||||  ||| | |  |||||  | ||||||| |||| ||
ERR  741 TGGCGTGAAGGAGTCAGCCATGGTCAACAAAATTTTCACCTGTATCAATGTCCTGGTCTGTGCTTCATC  810

H13  760 ATGGTGTCAGGATTTGTGAAGGATCGGTTAAAAAACTGGCAGCTCACGGAGGAGGATTTGGGAACACAT  829
         |||  ||| || || || ||    ||    ||||||||||||||||||| ||||      |||
ERR  811 GTGGGTGTCCGGGTTCGTGAAGGCTCCATTAAAAAACTGGCAGCTCACGGAGAAAATT........   868

H13  830 CAGGCCCGTCTCTGTTGAACAATGACAAAGAGGAAGCCCGGTGTGGTGATTCATGCCCTTCGG  899
         ||||| |||| |||  || |||| || || ||  |||| || ||||||  | |||||||||
ERR  869 .........TCTCCCTGTAACAACGACACAAACGTGAAATACGGTGAGGGAGGGTTTATGCCCTTTGG  929

H13  900 GTTCTCTGGTGTCCTGTCCTTCGTGCTTCTATGCCTTTGACTTGACTTGACTCGATCGCCACC  969
         |||||||||||||||||||||  ||||||| |||| ||||| |||||||||||||||||||||
ERR  930 ATTCTCTGGTGTCCTGTCAGGGGCAGCGGACCTGCTTTATGCCTTCGTGGGGGCTTTGACTTGACTTGACTCGTGTCATCGCCACC  999
```

FIG. 2B(1)

```
H13   970 ACAGGTGAAGAGGTGAAGAACCCAGAAGGCCATCCCGTGGGATCGTGGCCTCCCTGATCTGCT 1039
          |||||| |||| ||||| ||||||||||||||||| |||||||| |||||||||||| ||||
ERR  1000 ACAGGGGAAGAAGTCAAGAACCCCCAGAAGGCCATTCCGTGGGCATCGTGGCCTCCTCATTGCT 1069

H13  1040 TCATCGCCTACTTTGGGGGTGTCGGCTGCCCCTCACGCTCATGATGCCTACTTCTGCCTGACAATAACAG 1109
          |||| |||||||||||| ||||||| ||| ||| ||||||||| ||||||||| |||||| ||||
ERR  1070 TCATAGCGTACTTTGGCGTGTCCGCCGCTCTCACGCTCATGATGCCTTACTTCTGCCTGGACATCGACAG 1139

H13  1100 CCCCCCTGCCCGACGCCCTTAAGCACGTGGGGAAGAGTGCCAAGTACCAGTGGGCCGTGGGGCTCCCTC 1179
          ||| |||||| ||| ||||||||| |||||| ||| ||||||||| |||||||||||||||| ||
ERR  1140 CCCGCTGCCTGTGGTGCCCTTCAAGCACGTGGGGAAGAGCTAAGTACACGCAGTGGCCATTGGCCTCTCTC 1209

H13  1180 TGCGCTCTTTCCGCCAGTCTCTCTAGGTTCCATGCCTTCGGGTTATCTATGCCATGGCTGAGG 1249
          |||||||||| |||||| |||||  |||||||||||||| |||||| |||||||||||||
ERR  1210 TGCGACTTTCCACCAGTCTCCTAGGCTCCATGCCTATGATGTTATCTATGCCATGGCTGAAG 1279

H13  1250 ATGGACTGCTATTTAAATTCTTAGCCAACGTCAATGATAGGACCAAAACACCAATAATCGCCACATTAGC 1319
          |||||||||| |||| ||||||  |||| |||||| |||| |||||||| ||| |||||||| ||||
ERR  1280 ATGGACTGTTTAAATTTTTGGCCAAAATCAACAATAGGACCAAAACACCCGTAATGCCACTGTGAC 1349

H13  1320 CTCGGGTGCCGTTGTCGTGCTGATGGCCTTCCTCTTTGACCTGGTGGACTTGGTGACCTTCATGTCCATT 1389
          ||||||||||||| ||||||||| |||||| ||||||||| |||||||||||||| |||||||||
ERR  1350 CTCAGGCGCCATTGCTGCTGCTGATGGCCTTCCTCTTGAACTGAAGGACCTCATGTCCATT 1419

H13  1390 GGCACTCTCCTGGCTTACTCTTTGGTGCTGGTGTTTGGTCTTACGGTACCAGCAGCAGCCTA 1459
          ||||||||||||||||||||  |||||||||||| |||||| |||||||||||||||
ERR  1420 GGCACTCTCCTGGCTTACTCTTTGGTGCTGGTGTTTGGTCTTACGGTACCAGCCAGAACAACCTA 1489
```

FIG. 2B(2)

```
H13  1460 ACCTGGTATACCAGATGGCCAGTACTTCCGACGAGTTAGATCCAGCAGACCAAAATGAATTGGCAAGCAC 1529
          : |||||||||||||||||| ||   ||  |||||  ||||| |||   ||  |||||  ||  ||
ERR  1490 ATCTGGTATACCAGATGGCCAGAACCACCAGAACCAGAGATCGAGTAGATCAGAATGAGCTGGTCAGTGC 1559

H13  1530 CAATGATTCCCAGCTGGGCTGGGGTTTTACCAGAGGCAGAGATGTTCTCTTGAAAACCATACTCTCACCCAAA 1599
          ||||  ||||||||||   ||  |||| ||||||||  ||| |||| |||||||  ||||| ||||||| 
ERR  1560 CAGTGAATCACAGACAGGCTTTTTACGGTAGCCGAGAAGTTTTCTCTGAAATCCATCCTCTCACCCAAG 1629

H13  1600 AACATGGAGCCTTCCAAAATCTCTGGGCTAATTGTGAACATTTCAACCAGCCTTATAGCTGTTCTCATCA 1669
          |||| ||||||  ||||| |||  || |||||||||||| ||||| ||||| ||||| ||||||| |||
ERR  1630 AACGTGGAGCCCTCCAAATTCTCAGGGCTAATTGTGAACATTTCAGCCGGCCCTCCTAGCCGGCTCTTATCA 1699

H13  1670 TCACCTTCTGCATTGTGACGTGCTTGGAAGGGAGGCTCTCACCAAAGGGGCGTGTGGGCAGTCTTTCT 1739
          |||||  || |||||| | |||| |||| |||  || ||  ||||| |||| | |||||||||||| |
ERR  1700 TCACCGTGTGCATTGTGGCCGTGCTTGGAAGAGAGGCCCTGGGCCGAAGGGACACTGTGGGCAGTCTTTGT 1769

H13  1740 GCTCGCAGGGGTCTGCCCCTCTGTGTCCCTCTTGGGTGGTCACGGGGCGTCATCTGGAGGCAGCCCGAGAGCAAGACC 1809
          ||  ||||||    |||||||  |||| ||  ||||  ||  ||||  |||||||||||||||||||||||||||
ERR  1770 AATGACAGGGTCAGTCCTCCTCCTGCAGGTGACAGGCATCATCTGGAGACAGCCTGAGAGCAGCCCGAGAGCAAGACC 1839

H13  1810 AAGCTCTCATTTAAGGTTCCTTCCCTGCCAGTGCTCCCCATCCTGAGCATCTTCGTGAACGTCTATCTCA 1879
          ||||||||||||||||  ||||| ||  |||| |||||||||||||| |||||||||| ||||||||||
ERR  1840 AAGCTCTCATTTAAGGTACCCTTTGTCCCCGTACTTCCTGTCTTGAGCATCTTCGTGAACATCTATCTCA 1909

H13  1880 TGATGCAGCTGGACCAGGGCACCTGGGGTTTGCTCTGGGTTGCTGATAGGCTTCATCATCTACTT 1949
          |||||||||||||||||||||| |||||| |||  ||||  |||  ||||| || | || ||
ERR  1910 TGATGCAGCTGGACCAGGGCACGTGGGGTCCGGTTTGCAGTGTGGATGTCTGATAGGTTTCAGTAGGTTTCA 1979
```

FIG. 2C

```
H13  1950 TGGCTTATGGCCTGTGGCACAGCGAGGAGGCGTCCCTGGATGCCGACCAAGCAAGGACTCCTGACGGGCAAC 2019
              || |||||   |||||  || |||||| ||||||  ||| ||  ||| ||| |||||||| |||||||
ERR  1980 CGGTTATGGGATCTGGCACAGTGAGGAAGCGTCCCTGCTGGCCAGGCAAAGACTCCTGACAGCAAC 2049

H13  2020 TTGGACCAGTGCAAGTGACGCACAGCCCCG.........CCCCCGGAGCCCGAGGGACGCCCCAGA 2089
          ||||| ||||||| |||||  ||||||  ||          ||| || || || || |||  |||
ERR  2050 TTGGACCAGTGCAAATGAGTGCAAACGTGCAGCCCCACCAG.GGTGACAGCGG..TTGACGGGTGCCCGTAGA 2116

H13  2090 GGACCGGGGAGGCACCCCACCCTCCCCACCAGTGCAACAGAAACCACCTGCGTCCACACCCTCACTGCA 2157
          || |||| ||||  |   |||||||  |||    ||| ||  ||||  || || ||||  ||  |||
ERR  2117 AGCCTGGGA.CCCTCACAATCTCTCCACTCATGCCTCACTCAGGATCAGCTCACACCCCCAATGTCACCAAAGC 2185
```

FIG. 3A

```
ERR    1 MGCKNLLQLGQQMLRRKVVDCSREESRLSRCLNTYDLVALGVGSTLGAGVYVLAGAVARENAGPAIVISF  70
         ||||  ||  ||:||||||||| |||||| |||||| ||||||||||||||||||||||||||||||||
H13    1 MGCKVLLNIGQQMLRRKVVDCSREETRLSRCLNTFDLVALGVGSTLGAGVYVLAGAVARENAGPAIVISF  70

ERR   71 LIAALASVLAGLCIGEFGARVPKTGSAYLISYVTVGELMAFITGWNLILSYIIGTSSVARAWSATFDELI 140
         |||||||||||||||||||||||||||||||||||||||||||||||||||||||||||||||||||||
H13   71 LIAALASVLAGLCIGEFGARVPKTGSAYLISYVTVGELMAFITGWNLILSYIIGTSSVARAWSATFDELI 140

ERR  141 GRPIGEFSRQHMALNAPGVLAQTPDIFAVIIIILTQLLTLGVKESAMVNKIFTCINVLVLCFIVVSGFV  210
         |||||||| |:|||||||||| |:||||||||| |||||||||||||||||||||||||||:|||||
H13  141 GRPIGEFSRTHTLMAPGVLAENPDIFAVIIILLTQLLTLGVKESAMVNKIFTCINVLVLQFIMVSGFV   210
                                                                     ||.|||
TEA    1                                                              MVAGFV    6

ERR  211 RGSIKNMQLTEKNFS......CNNNDT.NVKY.GEGGFMPFGFSGVLSGAATCFYAFVGFDCIATTGEEV 272
         |||:|||||||||||      :|||||  |:| |||||||||||||||||||||||||||||||||||
H13  211 RGSVKNWQLTEEDFGNTSGRLCLNNDTKEGKP.GVGGFMPFGFSGVLSGAATCFYAFVGFDCIATTGEEV 279
         :|.|||:|||.|||:       .|::| | .|  |||  ||||||||||||||||||||||||||||
TEA    7 KGNVANWKISEEFLKWISASAREPPSENGTSIYGAGGFMPYGFTGTLAGAATCFYAFVGFDCIATTGEEV  76

ERR  273 RNPQKAIPVGIVASLLICFIAYFGVSAALTLMMPYFCLDIDSPLPGAFKHQQWEEAKYAVAIGSLCALST 342
           |::|:|||||:|:|||| ||:|||||||||||:    ::|:: :||||                  .
H13  280 RNPQKAIPVGIVASLLICFIAYFGVSAALTLMMPYFCLDNNSPLPDAFKHVGWEGAKYAVAVGSLCALSA 349
         :||||| ||||:||:||||:||||||||||||||||      |:: | :|  | ::|::|:|:|:||||
TEA   77 RNPQKAIPIGIVTSLLVCFMAYFGVSAALTLMMPYYLLDEKSPLPVAFEYVRMGPAKYVVAAGSLCALST 146
```

FIG. 3B

```
ERR 343 SLLGSMFPMPRVIYAMAEDGLLFKFLAKINNRTKTPVIATVTSGAIAAVMAFLFELKDLVDLMSIGTLLA 412
            ||||||||||||||||||||||||||||||||||||||||||||||||||||||||||||||||||
H13 350 SLLGSMFPMPRVIYAMAEDGLLFKFLANVNDRTKTPIIATLASGAVAAVMAFLFDLKDLVDLMSIGTLLA 419
            ||:|:|||||||||||||||||||::|:|||:|:::|:|:|:|||||||||||:|::|||||||||||
TEA 147 SLLGSIFPMPRVIYAMAEDGLLFKCLAQINSKTKTPVIATLSSGAVAAVMAFLFDLKALVDMSIGTLMA 216

ERR 413 YSLVAACVLVLRIYQPEQPNLVIQMARTTEELDRVDQNELVSASESQTGFLPVAEKFSLKSILSPKNVEPS 482
            ||||||||||||||||||||||:||:.|:..|:|:.|..||..::|:|
H13 420 YSLVAACVLVLRIYQPEQPNLVIQMASTSDELDPADQNELASTNDSQLGFLPEAEMFSLKTILSPKNMEPS 489
            ||||||||:|:|||||||||: ::: |:|::: :::|:
TEA 217 YSLVAACVLILRIYQPGLCIEQPKITPEKETLESCTNATLKS..ESQVIML.QGQGFSLRTLFSPSAL.PT 282

ERR 483 KFSGLIVNISAGLLAALIITVCIVAVLGREALAEGTIMAVFVMTGSVLLCMLVTGIWMRQPESKTKLSFK 552
            |:|||||||:.:::..:|:||:.::|:.|.:.||:|::||: :|:|
H13 490 KISGLIVNISTSLIAVLIITPCIVTVLGREALTKGALMAVPLLAGSALLCAVVTGVIWRQPESKTKLSFK 559
            :|: :|:.::: .::::::::::|:||..:| :::|:||: || |
TEA 283 RQSASLVSFLVGFLAFLILGLSILTTIGVQAIARLEAMSLALLALFVLCAAVILTINRQPQNQQKVAFM 352

ERR 563 VPFVPVLPVLSIFVNIILMQLDQGTMVRFPAVMLIGFTIYFGYGIWHSEEASL..AAGQAKTPDSNLDQ 620
            ||:|:||:||:|||||||||||||||||||||||||||||||||||||||||  :|:||:|||||||
H13 560 VPFLPVLPILSIFVNVILMQLDQGTWVRFPAVMLIGFIIYFGYGIWHSEEASL..DADQARTPDGNLDQ 627
            :. :: ::.: .:|:: :: :| |:
TEA 353 VPFLPFLPAFSILVNIILMVQLSADTWIRFSIKMALGFLIYFAYGIRHSLEGNPRDEEDDEDAFSENINV 422

ERR 621 CK 622
            ||
H13 628 CK 629
            ::
TEA 423 ATEEKSVMQANDHHQRNLSLPFILNEKTSEC 453
```

Numbers are the percent of the cell population containing the noted chromosome. Lane 1, human; lane 11, hamster; D, deletion at p15.1 -15.2; Dq, multiple deletion in 5q.

FIG. 14

```
H13  210  V  K  G  S  V  K  N  W  Q  L  T  E  E  D  F  G  N  T  S  G                           229
     775  GTGAAAGGATCGGTTAAAAACTGGCAGCTCACGGAGGAGGATTTTGGGAACACATCAGGC                           834
          ||||||||| || ||  |  |||||||||||||||||||||||| |  |||| |  |||
ERR  826  GTGAAAGGCTCCATTAAAAACTGGCAGCTCACGGAGAAAAATTCTCC............             873
     210     .     .     K     .     .     .     .     .     .  K  N  -  S                     225
                                            *                                 *

H13  230  R  L  C  L  N  N  D  T  K  E  G  K  P  G  V  G  G  F  M  P                           249
     835  CGTCTCTGTTTGAACAATGACACAAAAGAAGGGAAGCCCGGTGTTGGTGGATTCATGCCC                           894
          |||  ||||||  |||  ||  ||||     |||  ||| ||| || || ||  ||||||
ERR  874  TGTAACAACAACGACACA                AACGTGAAA TACGGTGAGGGAGGGTTTATGCCC                   924
     226     .  N  .  .  .  .  .  .           N  V  -  Y  -  E  .  .  .  .                     242
                   *
```

\* GLYCOSYLATION SITES

FIG. 17

EXTRACELLULAR DOMAIN 3

```
              1
H13 210   V  K  G  S   V  K N W Q L T E  E D  F G  N   T S G  229
     775  GTGAAAGGATCGGT AAAAACTGGCAGTCACGGAGGA TTT GGGAACACATCAGGC  834
          ||||||||||||||  ||||||||||||||||||||||  |||  ............
ERR 828   GTGAAAGGCTCCAT AAAAACTGGCAGTCACGGAG AAAAAT CTCC..........  873
     210                 I                          N  S            225

4            5                6              7A 7 7B
H13 230   R  L  C  L   N  N  D  T  K  E  G  K   E G  K   P  G  V  G  G  F  M  P  249
     835  CGTCTCTGT TTG AACAATGACACAAAGGAAGGG AAG GAAGGGAAG CCG GGT GTT GG TGGATTCATGCCC  924
          |||||||||  ||  |||||||      ||||||  |||    ||||||  |||  |||  |||  |  |||||||||
ERR 874   CGTCTCTGT TGT AACAACGACACA              AACGTG AA ATACGGT GAG GGGTTTATGCCC  924
     226              N                            N  V         Y  -  E           242
```

EXTRACELLULAR DOMAIN 4

```
              8                      9             10        11
H13 309   T  L  M  M  P  Y  F  C  L  D  N  N   S  P  L  P   D  A  F  K  H   V  G  W  E  G  A  335
    1072  ACGGCTCATGATGCCCTACTTCTGCCTGGA CAATAACAGCCCCCTGCCC GACGCCTTTAAGCAC GTGGGCTGGGAAGGTGCC  1152
          |||||||||||||||||||||||||||||| |||  ||||||||||||||| |||||||  ||||||| |||   |||||||||||
ERR 1102  ACGGCTCATGATGCCCTACTTCTGCCTGGA CAATATCGACAGCCCGCTGCCT GCCCTCAAGCACCTG GTCCAGGGGGAAGCT  1182
     302                               I  D                G              Q  -   E .       328
```

FIG. 20

```
AKv    391
       TTTCTCCTCCCCGGGGCCCCTGCTGTTCAGGAAGCAGGACTCCAGGCTCCAGGCTGTTCCAGA
       F  S  P  P  P  G  P  P  P  C  C  S  G  S  S  D  S  T  P  G  C  S  R
       64                SMAI
       304
AMPHO  ----------------------TATGTCGGGTAT-----------------------------
                           Y  V  G  Y
       64

AKv    GATTGTGAGGAGCCCCTGACTTCATATACTCCCGGTGCAATACGGCCTTGGAACAGACTTAAGTTA
       D  C  E  E  P  L  T  S  Y  T  P  H  C  N  T  A  W  N  R  L  K  L
                                        RSAI
AMPHO  ---------------------------------GGCTGCAAGTACCCCGCAGGGAGACAGCGGACC
                                        G  C  L  Y  P  A  G  R  Q  R  T
                                                                        78
                                                       SMAI   576
AKv    TCTAAAGTGACACACATGCACACACAATGGAGAGGATTCTATGTCTGCCCGGGCCACAT
       S  K  V  T  H  M  H  T  Q  W  R  G  F  Y  V  C  P  G  P  H
                                                                  126
                                                                        394
AMPHO  CGGACTTTTGAC---------------------------TTTACGTGTGCCCTGGGTAACCGTAAAGTCGGGCG
       R  T  F  D                              F  Y  V  C  P  G  H  T  V  K  S  G
                                                                                  94
```

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
      (A) LENGTH: 1102 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..1102

(xi) SEQUENCE DESCRIPTION: SEQ ID NO:1:

CCG GGC GCC ACC TTC GAC GAG CTG ATA GGC AGA CCC ATC GGG GAG TTC    48

```
Pro Gly Ala Thr Phe Asp Glu Leu Ile Gly Arg Pro Ile Gly Glu Phe
  1               5                  10                 15

TCA CGG ACA CAC ATG ACT CTG AAC GCC CCC GGC GTG CTG GCT GAA AAC        96
Ser Arg Thr His Met Thr Leu Asn Ala Pro Gly Val Leu Ala Glu Asn
                 20                  25                 30

CCC GAC ATA TTC GCA GTG ATC ATA ATT CTC ATC TTG ACA GGA CTT TTA       144
Pro Asp Ile Phe Ala Val Ile Ile Ile Leu Ile Leu Thr Gly Leu Leu
             35                  40                  45

ACT CTT GGT GTG AAA GAG TCG GCC ATG GTC AAC AAA ATA TTC ACT TGT       192
Thr Leu Gly Val Lys Glu Ser Ala Met Val Asn Lys Ile Phe Thr Cys
         50                  55                  60

ATT AAC GTC CTG GTC CTG GGC TTC ATA ATG GTG TCA GGA TTT GTG AAA       240
Ile Asn Val Leu Val Leu Gly Phe Ile Met Val Ser Gly Phe Val Lys
 65                  70                  75                  80

GGA TCG GTT AAA AAC TGG CAG CTC ACG GAG GAG GAT TTT GGG AAC ACA       288
Gly Ser Val Lys Asn Trp Gln Leu Thr Glu Glu Asp Phe Gly Asn Thr
                 85                  90                  95

TCA GGC CGT CTC TGT TTG AAC AAT GAC ACA AAA GAA GGG AAG CCC GGT       336
Ser Gly Arg Leu Cys Leu Asn Asn Asp Thr Lys Glu Gly Lys Pro Gly
             100                 105                 110

GTT GGT GGA TTC ATG CCC TTC GGG TTC TCT GGT GTC CTG TCG GGG GCA       384
Val Gly Gly Phe Met Pro Phe Gly Phe Ser Gly Val Leu Ser Gly Ala
         115                 120                 125

GCG ACT TGC TTC TAT GCC TTC GTG GGC TTT GAC TGC ATC GCC ACC ACA       432
Ala Thr Cys Phe Tyr Ala Phe Val Gly Phe Asp Cys Ile Ala Thr Thr
     130                 135                 140

GGT GAA GAG GTG AAG AAC CCA CAG AAG GCC ATC CCC GTG GGG ATC GTG       480
Gly Glu Glu Val Lys Asn Pro Gln Lys Ala Ile Pro Val Gly Ile Val
145                 150                 155                 160

GCG TCC CTC TTG ATC TGC TTC ATC GCC TAC TTT GGG GTG TCG GCT GCC       528
Ala Ser Leu Leu Ile Cys Phe Ile Ala Tyr Phe Gly Val Ser Ala Ala
                 165                 170                 175

CTC ACG CTC ATG ATG CCC TAC TTC TGC CTG GAC AAT AAC AGC CCC CTG       576
Leu Thr Leu Met Met Pro Tyr Phe Cys Leu Asp Asn Asn Ser Pro Leu
             180                 185                 190

CCC GAC GCC TTT AAG CAC GTG GGC TGG GAA GGT GCC AAG TAC GCA GTG       624
Pro Asp Ala Phe Lys His Val Gly Trp Glu Gly Ala Lys Tyr Ala Val
         195                 200                 205

GCC GTG GGC TCC CTC TGC GCT CTT TCC GCC AGT CTT CTA GGT TCC ATG       672
Ala Val Gly Ser Leu Cys Ala Leu Ser Ala Ser Leu Leu Gly Ser Met
     210                 215                 220

TTT CCC ATG CCT CGG GTT ATC TAT GCC ATG GCT GAG GAT GGA CTG CTA       720
Phe Pro Met Pro Arg Val Ile Tyr Ala Met Ala Glu Asp Gly Leu Leu
225                 230                 235                 240

TTT AAA TTC TTA GCC AAC GTC AAT GAT AGG ACC AAA ACA CCA ATA ATC       768
Phe Lys Phe Leu Ala Asn Val Asn Asp Arg Thr Lys Thr Pro Ile Ile
                 245                 250                 255

GCC ACA TTA GCC TCG GGT GCC GTT GCT GCT GTG ATG GCC TTC CTC TTT       816
Ala Thr Leu Ala Ser Gly Ala Val Ala Ala Val Met Ala Phe Leu Phe
             260                 265                 270

GAC CTG AAG GAC TTG GTG GAC CTC ATG TCC ATT GGC ACT CTC CTG GCT       864
Asp Leu Lys Asp Leu Val Asp Leu Met Ser Ile Gly Thr Leu Leu Ala
         275                 280                 285

TAC TCG TTG GTG GCT GCC TGT GTG TTG GTC TTA CGG TAC CAG CCA GAG       912
Tyr Ser Leu Val Ala Ala Cys Val Leu Val Leu Arg Tyr Gln Pro Glu
     290                 295                 300

CAG CCT AAC CTG GTA TAC CAG ATG GCC AGT ACT TCC GAC GAG TTA GAT       960
Gln Pro Asn Leu Val Tyr Gln Met Ala Ser Thr Ser Asp Glu Leu Asp
305                 310                 315                 320
```

```
CCA GCA GAC CAA AAT GAA TTG GCA AGC ACC AAT GAT TCC CAG CTG GGG      1008
Pro Ala Asp Gln Asn Glu Leu Ala Ser Thr Asn Asp Ser Gln Leu Gly
            325                 330                 335

TTT TTA CCA GAG GCA GAG ATG TTC TCT TTG AAA ACC ATA CTC TCA CCC      1056
Phe Leu Pro Glu Ala Glu Met Phe Ser Leu Lys Thr Ile Leu Ser Pro
            340                 345                 350

AAA AAC ATG GAG CCT TCC AAA ATC TCT GGG CTA ATT GTG AAC CCG G        1102
Lys Asn Met Glu Pro Ser Lys Ile Ser Gly Leu Ile Val Asn Pro
            355                 360                 365
```

(2) INFORMATION FOR SEQ ID NO:2:

(i) SEQUENCE CHARACTERISTICS:
        (A) LENGTH: 367 amino acids
        (B) TYPE: amino acid
        (D) TOPOLOGY: linear (ii) MOLECULE TYPE: protein (xi) SEQUENCE DESCRIPTION: SEQ ID NO:2:

```
Pro Gly Ala Thr Phe Asp Glu Leu Ile Gly Arg Pro Ile Gly Glu Phe
 1               5                  10                  15

Ser Arg Thr His Met Thr Leu Asn Ala Pro Gly Val Leu Ala Glu Asn
                20                  25                  30

Pro Asp Ile Phe Ala Val Ile Ile Leu Ile Leu Thr Gly Leu Leu
            35                  40                  45

Thr Leu Gly Val Lys Glu Ser Ala Met Val Asn Lys Ile Phe Thr Cys
 50                  55                  60

Ile Asn Val Leu Val Leu Gly Phe Ile Met Val Ser Gly Phe Val Lys
 65                  70                  75                  80

Gly Ser Val Lys Asn Trp Gln Leu Thr Glu Glu Asp Phe Gly Asn Thr
                85                  90                  95

Ser Gly Arg Leu Cys Leu Asn Asn Asp Thr Lys Glu Gly Lys Pro Gly
                100                 105                 110

Val Gly Gly Phe Met Pro Phe Gly Phe Ser Gly Val Leu Ser Gly Ala
            115                 120                 125

Ala Thr Cys Phe Tyr Ala Phe Val Gly Phe Asp Cys Ile Ala Thr Thr
            130                 135                 140

Gly Glu Glu Val Lys Asn Pro Gln Lys Ala Ile Pro Val Gly Ile Val
145                 150                 155                 160

Ala Ser Leu Leu Ile Cys Phe Ile Ala Tyr Phe Gly Val Ser Ala Ala
                165                 170                 175

Leu Thr Leu Met Met Pro Tyr Phe Cys Leu Asp Asn Asn Ser Pro Leu
                180                 185                 190

Pro Asp Ala Phe Lys His Val Gly Trp Glu Gly Ala Lys Tyr Ala Val
            195                 200                 205

Ala Val Gly Ser Leu Cys Ala Leu Ser Ala Ser Leu Leu Gly Ser Met
            210                 215                 220

Phe Pro Met Pro Arg Val Ile Tyr Ala Met Ala Glu Asp Gly Leu Leu
225                 230                 235                 240

Phe Lys Phe Leu Ala Asn Val Asn Asp Arg Thr Lys Thr Pro Ile Ile
                245                 250                 255

Ala Thr Leu Ala Ser Gly Ala Val Ala Val Met Ala Phe Leu Phe
            260                 265                 270

Asp Leu Lys Asp Leu Val Asp Leu Met Ser Ile Gly Thr Leu Leu Ala
            275                 280                 285

Tyr Ser Leu Val Ala Ala Cys Val Leu Val Leu Arg Tyr Gln Pro Glu
```

```
                    290                  295                  300
Gln Pro Asn Leu Val Tyr Gln Met Ala Ser Thr Ser Asp Glu Leu Asp
305                 310                 315                 320

Pro Ala Asp Gln Asn Glu Leu Ala Ser Thr Asn Asp Ser Gln Leu Gly
                325                 330                 335

Phe Leu Pro Glu Ala Glu Met Phe Ser Leu Lys Thr Ile Leu Ser Pro
            340                 345                 350

Lys Asn Met Glu Pro Ser Lys Ile Ser Gly Leu Ile Val Asn Pro
        355                 360                 365

(2) INFORMATION FOR SEQ ID NO:3:

(i) SEQUENCE CHARACTERISTICS:
        (A) LENGTH: 2425 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 199..2064

(xi) SEQUENCE DESCRIPTION: SEQ ID NO:3:

GATTCCGCCC GCGTGCGCCA TCCCCTCAGC TAGCAGGTGT GAGAGGCTTT CTACCCGCGG      60

TCTCCACACA GCTCAACATC TTGCCGCCTC CTCCGAGCCT GAAGCTACCG TGGACTCTGC    120

TGTGGCGTCT TGGCCCCCAG GTGCGGATCC TCCCCAGTGA AAGTCCCAC GAGTCTTACA     180

GCAGATTCGC TCAGCACA ATG GGC TGC AAA AAC CTG CTC GGT CTG GGC CAG      231
                    Met Gly Cys Lys Asn Leu Leu Gly Leu Gly Gln
                     1               5                  10

CAG ATG CTG CGC CGG AAG GTG GTG GAC TGC AGC CGG GAG GAG AGC CGG      279
Gln Met Leu Arg Arg Lys Val Val Asp Cys Ser Arg Glu Glu Ser Arg
            15                  20                  25

CTG TCC CGC TGC CTC AAC ACC TAT GAC CTG GTA GCT CTT GGG GTG GGC      327
Leu Ser Arg Cys Leu Asn Thr Tyr Asp Leu Val Ala Leu Gly Val Gly
        30                  35                  40

AGC ACC TTG GGC GCT GGT GTC TAT GTC CTA GCC GGT GCC GTG GCC CGT      375
Ser Thr Leu Gly Ala Gly Val Tyr Val Leu Ala Gly Ala Val Ala Arg
    45                  50                  55

GAA AAT GCT GGC CCT GCC ATC GTC ATC TCC TTC TTG ATT GCT GCT CTC      423
Glu Asn Ala Gly Pro Ala Ile Val Ile Ser Phe Leu Ile Ala Ala Leu
60                  65                  70                  75

GCC TCC GTG CTG GCC GGC CTG TGC TAC GGC GAG TTT GGT GCC CGT GTC      471
Ala Ser Val Leu Ala Gly Leu Cys Tyr Gly Glu Phe Gly Ala Arg Val
                80                  85                  90

CCC AAG ACG GGC TCA GCC TAC CTC TAC AGC TAC GTG ACG GTG GGG GAG      519
Pro Lys Thr Gly Ser Ala Tyr Leu Tyr Ser Tyr Val Thr Val Gly Glu
            95                  100                 105

CTT TGG GCC TTC ATC ACT GGC TGG AAC CTG ATT CTC TCC TAC ATC ATC      567
Leu Trp Ala Phe Ile Thr Gly Trp Asn Leu Ile Leu Ser Tyr Ile Ile
        110                 115                 120

GGT ACT TCA AGC GTG GCA AGA GCC TGG AGT GCG ACT TTT GAC GAG CTG      615
Gly Thr Ser Ser Val Ala Arg Ala Trp Ser Ala Thr Phe Asp Glu Leu
    125                 130                 135

ATA GGC AAG CCC ATC GGA GAG TTC TCA CGT CAG CAC ATG GCC CTG AAT      663
Ile Gly Lys Pro Ile Gly Glu Phe Ser Arg Gln His Met Ala Leu Asn
140                 145                 150                 155

GCT CCT GGG GTG CTG GCC CAA ACC CCG GAC ATA TTT GCT GTG ATT ATA      711
Ala Pro Gly Val Leu Ala Gln Thr Pro Asp Ile Phe Ala Val Ile Ile
```

```
                    160                 165                 170
ATT ATC ATC TTA ACA GGA CTG TTA ACT CTT GGC GTG AAG GAG TCA GCC     759
Ile Ile Ile Leu Thr Gly Leu Leu Thr Leu Gly Val Lys Glu Ser Ala
            175                 180                 185

ATG GTC AAC AAA ATT TTC ACC TGT ATC AAT GTC CTG GTC TTG TGC TTC     807
Met Val Asn Lys Ile Phe Thr Cys Ile Asn Val Leu Val Leu Cys Phe
        190                 195                 200

ATC GTG GTG TCC GGG TTC GTG AAA GGC TCC ATT AAA AAC TGG CAG CTC     855
Ile Val Val Ser Gly Phe Val Lys Gly Ser Ile Lys Asn Trp Gln Leu
    205                 210                 215

ACG GAG AAA AAT TTC TCC TGT AAC AAC AAC GAC ACA AAC GTG AAA TAC     903
Thr Glu Lys Asn Phe Ser Cys Asn Asn Asn Asp Thr Asn Val Lys Tyr
220                 225                 230                 235

GGT GAG GGA GGG TTT ATG CCC TTT GGA TTC TCT GGT GTC CTG TCA GGG     951
Gly Glu Gly Gly Phe Met Pro Phe Gly Phe Ser Gly Val Leu Ser Gly
                240                 245                 250

GCA GCG ACC TGC TTT TAT GCC TTC GTG GGC TTT GAC TGC ATC GCC ACC     999
Ala Ala Thr Cys Phe Tyr Ala Phe Val Gly Phe Asp Cys Ile Ala Thr
            255                 260                 265

ACA GGG GAA GAA GTC AAG AAC CCC CAG AAG GCC ATT CCT GTG GGC ATC    1047
Thr Gly Glu Glu Val Lys Asn Pro Gln Lys Ala Ile Pro Val Gly Ile
        270                 275                 280

GTG GCG TCC CTC CTC ATT TGC TTC ATA GCG TAC TTT GGC GTG TCC GCC    1095
Val Ala Ser Leu Leu Ile Cys Phe Ile Ala Tyr Phe Gly Val Ser Ala
    285                 290                 295

GCT CTC ACG CTC ATG ATG CCT TAC TTC TGC CTG GAC ATC GAC AGC CCG    1143
Ala Leu Thr Leu Met Met Pro Tyr Phe Cys Leu Asp Ile Asp Ser Pro
300                 305                 310                 315

CTG CCT GGT GCC TTC AAG CAC CAG GGC TGG GAA GAA GCT AAG TAC GCA    1191
Leu Pro Gly Ala Phe Lys His Gln Gly Trp Glu Glu Ala Lys Tyr Ala
                320                 325                 330

GTG GCC ATT GGC TCT CTC TGC GCA CTT TCC ACC AGT CTC CTA GGC TCC    1239
Val Ala Ile Gly Ser Leu Cys Ala Leu Ser Thr Ser Leu Leu Gly Ser
            335                 340                 345

ATG TTT CCC ATG CCC CGA GTT ATC TAT GCC ATG GCT GAA GAT GGA CTA    1287
Met Phe Pro Met Pro Arg Val Ile Tyr Ala Met Ala Glu Asp Gly Leu
        350                 355                 360

CTG TTT AAA TTT TTG GCC AAA ATC AAC AAT AGG ACC AAA ACA CCC GTA    1335
Leu Phe Lys Phe Leu Ala Lys Ile Asn Asn Arg Thr Lys Thr Pro Val
    365                 370                 375

ATC GCC ACT GTG ACC TCA GGC GCC ATT GCT GCT GTG ATG GCC TTC CTC    1383
Ile Ala Thr Val Thr Ser Gly Ala Ile Ala Ala Val Met Ala Phe Leu
380                 385                 390                 395

TTT GAA CTG AAG GAC CTG GTG GAC CTC ATG TCC ATT GGC ACT CTC CTG    1431
Phe Glu Leu Lys Asp Leu Val Asp Leu Met Ser Ile Gly Thr Leu Leu
                400                 405                 410

GCT TAC TCT TTG GTG GCT GCC TGT GTT TTG GTC TTA CGG TAC CAG CCA    1479
Ala Tyr Ser Leu Val Ala Ala Cys Val Leu Val Leu Arg Tyr Gln Pro
            415                 420                 425

GAA CAA CCT AAT CTG GTA TAC CAG ATG GCC AGA ACC ACC GAG GAG CTA    1527
Glu Gln Pro Asn Leu Val Tyr Gln Met Ala Arg Thr Thr Glu Glu Leu
        430                 435                 440

GAT CGA GTA GAT CAG AAT GAG CTG GTC AGT GCC AGT GAA TCA CAG ACA    1575
Asp Arg Val Asp Gln Asn Glu Leu Val Ser Ala Ser Glu Ser Gln Thr
    445                 450                 455

GGC TTT TTA CCG GTA GCC GAG AAG TTT TCT CTG AAA TCC ATC CTC TCA    1623
Gly Phe Leu Pro Val Ala Glu Lys Phe Ser Leu Lys Ser Ile Leu Ser
460                 465                 470                 475

CCC AAG AAC GTG GAG CCC TCC AAA TTC TCA GGG CTA ATT GTG AAC ATT    1671
```

```
                                                                      Pro Lys Asn Val Glu Pro Ser Lys Phe Ser Gly Leu Ile Val Asn Ile
                                                                                      480                 485                 490

TCA GCC GGC CTC CTA GCC GCT CTT ATC ATC ACC GTG TGC ATT GTG GCC                                                                  1719
Ser Ala Gly Leu Leu Ala Ala Leu Ile Ile Thr Val Cys Ile Val Ala
                495                 500                 505

GTG CTT GGA AGA GAG GCC CTG GCC GAA GGG ACA CTG TGG GCA GTC TTT                                                                  1767
Val Leu Gly Arg Glu Ala Leu Ala Glu Gly Thr Leu Trp Ala Val Phe
                510                 515                 520

GTA ATG ACA GGG TCA GTC CTC CTC TGC ATG CTG GTG ACA GGC ATC ATC                                                                  1815
Val Met Thr Gly Ser Val Leu Leu Cys Met Leu Val Thr Gly Ile Ile
        525                 530                 535

TGG AGA CAG CCT GAG AGC AAG ACC AAG CTC TCA TTT AAG GTA CCC TTT                                                                  1863
Trp Arg Gln Pro Glu Ser Lys Thr Lys Leu Ser Phe Lys Val Pro Phe
540                 545                 550                 555

GTC CCC GTA CTT CCT GTC TTG AGC ATC TTC GTG AAC ATC TAT CTC ATG                                                                  1911
Val Pro Val Leu Pro Val Leu Ser Ile Phe Val Asn Ile Tyr Leu Met
                560                 565                 570

ATG CAG CTG GAC CAG GGC ACG TGG GTC CGG TTT GCA GTG TGG ATG CTG                                                                  1959
Met Gln Leu Asp Gln Gly Thr Trp Val Arg Phe Ala Val Trp Met Leu
                575                 580                 585

ATA GGT TTC ACC ATC TAT TTC GGT TAT GGG ATC TGG CAC AGT GAG GAA                                                                  2007
Ile Gly Phe Thr Ile Tyr Phe Gly Tyr Gly Ile Trp His Ser Glu Glu
                590                 595                 600

GCG TCC CTG GCT GCT GGC CAG GCA AAG ACT CCT GAC AGC AAC TTG GAC                                                                  2055
Ala Ser Leu Ala Ala Gly Gln Ala Lys Thr Pro Asp Ser Asn Leu Asp
        605                 610                 615

CAG TGC AAA TGACGTGCAG CCCCACCCAC CAGGGTGACA GCGGTTGACG                                                                          2104
Gln Cys Lys
620

GGTGCCCGTA GAAGCCTGGG ACCCTCACAA TCTCTCCACT CATGCCTCAG GATCAGCTCA                                                                2164

CACCCCCAAT GTCACCAAAG CTGGTTTGCT GCCAGCTCGT GAGATCCTGG TCATTTCTGG                                                                2224

ACAGTCCCTT GGTTTACTCA TCTCCCTCTG AACAAAGAAA GCAGCCCTTC TCCTTGCCGG                                                                2284

CCGGCCGGGC GCTTCGCTGC TGCGGCCCCA GCAGAAGGGA GGCCCCCTTC TCCTCTCACT                                                                2344

TGGGAAGCAG GCCTCCCTCC CTCCCTGGGA CCACCCTGGC ATCGCCCATG TGCACACTCC                                                                2404

AGATGGCTAG TGAGCCTCTC C                                                                                                          2425

(2) INFORMATION FOR SEQ ID NO:4:

(i) SEQUENCE CHARACTERISTICS:
        (A) LENGTH: 622 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Met Gly Cys Lys Asn Leu Leu Gly Leu Gly Gln Gln Met Leu Arg Arg
1               5                   10                  15

Lys Val Val Asp Cys Ser Arg Glu Glu Ser Arg Leu Ser Arg Cys Leu
                20                  25                  30

Asn Thr Tyr Asp Leu Val Ala Leu Gly Val Gly Ser Thr Leu Gly Ala
            35                  40                  45

Gly Val Tyr Val Leu Ala Gly Ala Val Ala Arg Glu Asn Ala Gly Pro
        50                  55                  60

Ala Ile Val Ile Ser Phe Leu Ile Ala Ala Leu Ala Ser Val Leu Ala
65                  70                  75                  80
```

-continued

```
Gly Leu Cys Tyr Gly Glu Phe Ala Arg Val Pro Lys Thr Gly Ser
                 85                  90                  95
Ala Tyr Leu Tyr Ser Tyr Val Thr Val Gly Glu Leu Trp Ala Phe Ile
                100                 105                 110
Thr Gly Trp Asn Leu Ile Leu Ser Tyr Ile Ile Gly Thr Ser Ser Val
            115                 120                 125
Ala Arg Ala Trp Ser Ala Thr Phe Asp Glu Leu Ile Gly Lys Pro Ile
        130                 135                 140
Gly Glu Phe Ser Arg Gln His Met Ala Leu Asn Ala Pro Gly Val Leu
145                 150                 155                 160
Ala Gln Thr Pro Asp Ile Phe Ala Val Ile Ile Ile Ile Leu Thr
                165                 170                 175
Gly Leu Leu Thr Leu Gly Val Lys Glu Ser Ala Met Val Asn Lys Ile
                180                 185                 190
Phe Thr Cys Ile Asn Val Leu Val Leu Cys Phe Ile Val Val Ser Gly
            195                 200                 205
Phe Val Lys Gly Ser Ile Lys Asn Trp Gln Leu Thr Glu Lys Asn Phe
        210                 215                 220
Ser Cys Asn Asn Asn Asp Thr Asn Val Lys Tyr Gly Glu Gly Gly Phe
225                 230                 235                 240
Met Pro Phe Gly Phe Ser Gly Val Leu Ser Gly Ala Ala Thr Cys Phe
                245                 250                 255
Tyr Ala Phe Val Gly Phe Asp Cys Ile Ala Thr Thr Gly Glu Glu Val
                260                 265                 270
Lys Asn Pro Gln Lys Ala Ile Pro Val Gly Ile Val Ala Ser Leu Leu
            275                 280                 285
Ile Cys Phe Ile Ala Tyr Phe Gly Val Ser Ala Ala Leu Thr Leu Met
        290                 295                 300
Met Pro Tyr Phe Cys Leu Asp Ile Asp Ser Pro Leu Pro Gly Ala Phe
305                 310                 315                 320
Lys His Gln Gly Trp Glu Glu Ala Lys Tyr Ala Val Ala Ile Gly Ser
                325                 330                 335
Leu Cys Ala Leu Ser Thr Ser Leu Leu Gly Ser Met Phe Pro Met Pro
            340                 345                 350
Arg Val Ile Tyr Ala Met Ala Glu Asp Gly Leu Leu Phe Lys Phe Leu
        355                 360                 365
Ala Lys Ile Asn Asn Arg Thr Lys Thr Pro Val Ile Ala Thr Val Thr
    370                 375                 380
Ser Gly Ala Ile Ala Ala Val Met Ala Phe Leu Phe Glu Leu Lys Asp
385                 390                 395                 400
Leu Val Asp Leu Met Ser Ile Gly Thr Leu Leu Ala Tyr Ser Leu Val
                405                 410                 415
Ala Ala Cys Val Leu Val Leu Arg Tyr Gln Pro Glu Gln Pro Asn Leu
            420                 425                 430
Val Tyr Gln Met Ala Arg Thr Thr Glu Glu Leu Asp Arg Val Asp Gln
        435                 440                 445
Asn Glu Leu Val Ser Ala Ser Glu Ser Gln Thr Gly Phe Leu Pro Val
450                 455                 460
Ala Glu Lys Phe Ser Leu Lys Ser Ile Leu Ser Pro Lys Asn Val Glu
465                 470                 475                 480
Pro Ser Lys Phe Ser Gly Leu Ile Val Asn Ile Ser Ala Gly Leu Leu
                485                 490                 495
Ala Ala Leu Ile Ile Thr Val Cys Ile Val Ala Val Leu Gly Arg Glu
```

-continued

```
                    500                 505                 510
Ala Leu Ala Glu Gly Thr Leu Trp Ala Val Phe Val Met Thr Gly Ser
        515                 520                 525

Val Leu Leu Cys Met Leu Val Thr Gly Ile Ile Trp Arg Gln Pro Glu
    530                 535                 540

Ser Lys Thr Lys Leu Ser Phe Lys Val Pro Phe Pro Val Leu Pro
545                 550                 555                 560

Val Leu Ser Ile Phe Val Asn Ile Tyr Leu Met Met Gln Leu Asp Gln
                565                 570                 575

Gly Thr Trp Val Arg Phe Ala Val Trp Met Leu Ile Gly Phe Thr Ile
            580                 585                 590

Tyr Phe Gly Tyr Gly Ile Trp His Ser Glu Glu Ala Ser Leu Ala Ala
        595                 600                 605

Gly Gln Ala Lys Thr Pro Asp Ser Asn Leu Asp Gln Cys Lys
610                 615                 620
```

(2) INFORMATION FOR SEQ ID NO:5:

(i) SEQUENCE CHARACTERISTICS:
        (A) LENGTH: 2397 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION:410..1768

(xi) SEQUENCE DESCRIPTION: SEQ ID NO:5:

```
GGGTGTCTTT CCTCATCGCT GCCCTGGCCT CGGTTATGGC CGGCCTTTGC TATGCTGAAT      60

TTGGGGCCCG AGTACCCAAG ACTGGATCTG CGTATCTATA CACTTACGTC ACGGTCGGAG     120

AGCTGTGGGC CTTCATCACT GGCTGGAATC TCATCCTGTC ATATGTCATA GGTACGTCCA     180

GTGTCGCAAG AGCATGGAGT GGCACCTTTG ACGAACTTCT TAATAAACAG ATTGGCCAGT     240

TTTTCAAAAC GTACTTCAAA ATGAATTACA CTGGTCTGGC AGAGTATCCA GACTTCTTTG     300

CCGTGTGCCT TGTATTACTC CTGGCAGGTC TTTTATCTTT TGGAGTAAAA GAGTCTGCTT     360

GGGTGAATAA ATTTTTACAG CTATTAATAT CCTGGTCCTT CTCTTTGTC ATG GTG         415
                                                     Met Val
                                                       1

GCT GGG TTT GTG AAA GGA AAT GTG GCT AAC TGG AAG ATC AGT GAA GAG       463
Ala Gly Phe Val Lys Gly Asn Val Ala Asn Trp Lys Ile Ser Glu Glu
        5                  10                  15

TTT CTC AAA AAT ATA TCA GCA AGT GCT AGA GAA CCA CCT TCT GAG AAC       511
Phe Leu Lys Asn Ile Ser Ala Ser Ala Arg Glu Pro Pro Ser Glu Asn
 20                  25                  30

GGA ACA AGC ATC TAC GGG GCT GGC GGC TTT ATG CCC TAT GGC TTT ACA       559
Gly Thr Ser Ile Tyr Gly Ala Gly Gly Phe Met Pro Tyr Gly Phe Thr
 35                  40                  45                  50

GGG ACG TTG GCT GGT GCT GCA ACG TGC TTT TAT GCC TTT GTG GGC TTT       607
Gly Thr Leu Ala Gly Ala Ala Thr Cys Phe Tyr Ala Phe Val Gly Phe
             55                  60                  65

GAC TGC ATT GCA ACA ACC GGT GAA GAG GTT CGG AAT CCA CAA AAG GCG       655
Asp Cys Ile Ala Thr Thr Gly Glu Glu Val Arg Asn Pro Gln Lys Ala
         70                  75                  80

ATC CCC ATC GGA ATA GTG ACG TCC TTA CTT GTC TGC TTT ATG GCT TAC       703
Ile Pro Ile Gly Ile Val Thr Ser Leu Leu Val Cys Phe Met Ala Tyr
     85                  90                  95
```

-continued

```
TTT GGG GTT TCT GCA GCT TTA ACG CTT ATG ATG CCT TAC TAC CTC CTG      751
Phe Gly Val Ser Ala Ala Leu Thr Leu Met Met Pro Tyr Tyr Leu Leu
    100                 105                 110

GAT GAG AAA AGT CCA CTC CCA GTC GCG TTT GAG TAT GTC AGA TGG GGC      799
Asp Glu Lys Ser Pro Leu Pro Val Ala Phe Glu Tyr Val Arg Trp Gly
115                 120                 125                 130

CCC GCC AAA TAC GTT GTC GCA GCA GGC TCC CTC TGC GCC TTA TCA ACA      847
Pro Ala Lys Tyr Val Val Ala Ala Gly Ser Leu Cys Ala Leu Ser Thr
                135                 140                 145

AGT CTT CTT GGA TCC ATT TTC CCA ATG CCT CGT GTA ATC TAT GCT ATG      895
Ser Leu Leu Gly Ser Ile Phe Pro Met Pro Arg Val Ile Tyr Ala Met
            150                 155                 160

GCG GAG GAT GGG TTG CTT TTC AAA TGT CTA GCT CAA ATC AAT TCC AAA      943
Ala Glu Asp Gly Leu Leu Phe Lys Cys Leu Ala Gln Ile Asn Ser Lys
        165                 170                 175

ACG AAG ACA CCA GTA ATT GCT ACT TTG TCA TCG GGT GCA GTG GCA GCT      991
Thr Lys Thr Pro Val Ile Ala Thr Leu Ser Ser Gly Ala Val Ala Ala
    180                 185                 190

GTG ATG GCC TTT CTT TTT GAC CTG AAG GCC CTC GTG GAC ATG ATG TCT     1039
Val Met Ala Phe Leu Phe Asp Leu Lys Ala Leu Val Asp Met Met Ser
195                 200                 205                 210

ATT GGC ACC CTC ATG GCC TAC TCT CTG GTG GCA GCC TGT GTG CTT ATT     1087
Ile Gly Thr Leu Met Ala Tyr Ser Leu Val Ala Ala Cys Val Leu Ile
                215                 220                 225

CTC AGG TAC CAA CCT GGC TTG TGT TAC GAG CAG CCC AAA TAC ACC CCT     1135
Leu Arg Tyr Gln Pro Gly Leu Cys Tyr Glu Gln Pro Lys Tyr Thr Pro
            230                 235                 240

GAG AAA GAA ACT CTG GAA TCA TGT ACC AAT GCG ACT TTG AAG AGC GAG     1183
Glu Lys Glu Thr Leu Glu Ser Cys Thr Asn Ala Thr Leu Lys Ser Glu
        245                 250                 255

TCC CAG GTC ACC ATG CTG CAA GGA CAG GGT TTC AGC CTA CGA ACC CTC     1231
Ser Gln Val Thr Met Leu Gln Gly Gln Gly Phe Ser Leu Arg Thr Leu
    260                 265                 270

TTC AGC CCC TCT GCC CTG CCC ACA CGA CAG TCG GCT TCC CTT GTG AGC     1279
Phe Ser Pro Ser Ala Leu Pro Thr Arg Gln Ser Ala Ser Leu Val Ser
275                 280                 285                 290

TTT CTG GTG GGA TTC CTG GCT TTC CTC ATC CTG GGC TTG AGT ATT CTA     1327
Phe Leu Val Gly Phe Leu Ala Phe Leu Ile Leu Gly Leu Ser Ile Leu
                295                 300                 305

ACC ACG TAT GGC GTC CAG GCC ATT GCC AGA CTG GAA GCC TGG AGC CTG     1375
Thr Thr Tyr Gly Val Gln Ala Ile Ala Arg Leu Glu Ala Trp Ser Leu
            310                 315                 320

GCT CTT CTC GCC CTG TTC CTT GTC CTC TGC GCT GCC GTC ATT CTG ACC     1423
Ala Leu Leu Ala Leu Phe Leu Val Leu Cys Ala Ala Val Ile Leu Thr
        325                 330                 335

ATT TGG AGG CAG CCA CAG AAT CAG CAA AAA GTA GCC TTC ATG GTC CCG     1471
Ile Trp Arg Gln Pro Gln Asn Gln Gln Lys Val Ala Phe Met Val Pro
    340                 345                 350

TTC TTA CCG TTT CTG CCG GCC TTC AGC ATC CTG GTC AAC ATT TAC TTG     1519
Phe Leu Pro Phe Leu Pro Ala Phe Ser Ile Leu Val Asn Ile Tyr Leu
355                 360                 365                 370

ATG GTC CAG TTA AGT GCG GAC ACT TGG ATC AGA TTC AGC ATC TGG ATG     1567
Met Val Gln Leu Ser Ala Asp Thr Trp Ile Arg Phe Ser Ile Trp Met
                375                 380                 385

GCG CTT GGC TTT CTG ATC TAT TTC GCC TAT GGC ATT AGA CAC AGC TTG     1615
Ala Leu Gly Phe Leu Ile Tyr Phe Ala Tyr Gly Ile Arg His Ser Leu
            390                 395                 400

GAG GGT AAC CCC AGG GAC GAA GAA GAC GAT GAG GAT GCC TTT TCA GAA     1663
Glu Gly Asn Pro Arg Asp Glu Glu Asp Asp Glu Asp Ala Phe Ser Glu
```

```
                    405                 410                 415
AAC ATC AAT GTA GCA ACA GAA GAA AAG TCC GTC ATG CAA GCA AAT GAC        1711
Asn Ile Asn Val Ala Thr Glu Glu Lys Ser Val Met Gln Ala Asn Asp
            420                 425                 430

CAT CAC CAA AGA AAC CTC AGC TTA CCT TTC ATA CTT CAT GAA AAG ACA        1759
His His Gln Arg Asn Leu Ser Leu Pro Phe Ile Leu His Glu Lys Thr
435                 440                 445                 450

AGT GAA TGT TGATGCTGGC CCTCGGTCTT ACCACGCATA CCTTAACAAT                1808
Ser Glu Cys

GAGTACACTG TGGCCGGATG CCACCATCGT GCTGGGCTGT CGTGGGTCTG CTGTGGACAT      1868

GGCTTGCCTA ACTTGTACTT CCTCCTCCAG ACAGCTTCTC TTCAGATGGT GGATTCTGTG      1928

TCTGAGGAGA CTGCCTGAGA GCACTCCTCA GCTATATGTA TCCCCAAAAC AGTATGTCCG      1988

TGTGCGTACA TGTATGTCTG CGATGTGAGT GTTCAATGTT GTCCGTTATT AGTCTGTGAC      2048

ATAATTCCAG CATGGTAATT GGTGGCATAT ACTGCACACA CTAGTAAACA GTATATTGCT      2108

GAATAGAGAT GTATTCTGTA TATGTCCTAG GTGGCTGGGG AAATAGTGGT GGTTTCTTTA      2168

TTAGGTATAT GACCATCAGT TTGGACATAC TGAAATGCCA TCCCCTGTCA GGATGTTTAA      2228

CAGTGGTCAT GGGTGGGGAA GGGATAAGGA ATGGGCATTG TCTATAAATT GTAATGCATA      2288

TATCCTTCTC CTACTTGCTA AGACAGCTTT CTTAAACGGC CAGGGAGAGT GTTTCTTTCC      2348

TCTGTATGAC AAGATGAAGA GGTAGTCTGT GGCTGGAGAT GGCCAATCC                  2397
```

(2) INFORMATION FOR SEQ ID NO:6:

(i) SEQUENCE CHARACTERISTICS:
        (A) LENGTH: 453 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Met Val Ala Gly Phe Val Lys Gly Asn Val Ala Asn Trp Lys Ile Ser
1               5                   10                  15

Glu Glu Phe Leu Lys Asn Ile Ser Ala Ser Ala Arg Glu Pro Pro Ser
                20                  25                  30

Glu Asn Gly Thr Ser Ile Tyr Gly Ala Gly Gly Phe Met Pro Tyr Gly
            35                  40                  45

Phe Thr Gly Thr Leu Ala Gly Ala Ala Thr Cys Phe Tyr Ala Phe Val
50                  55                  60

Gly Phe Asp Cys Ile Ala Thr Thr Gly Glu Glu Val Arg Asn Pro Gln
65                  70                  75                  80

Lys Ala Ile Pro Ile Gly Ile Val Thr Ser Leu Leu Val Cys Phe Met
                85                  90                  95

Ala Tyr Phe Gly Val Ser Ala Ala Leu Thr Leu Met Met Pro Tyr Tyr
            100                 105                 110

Leu Leu Asp Glu Lys Ser Pro Leu Pro Val Ala Phe Glu Tyr Val Arg
        115                 120                 125

Trp Gly Pro Ala Lys Tyr Val Val Ala Ala Gly Ser Leu Cys Ala Leu
130                 135                 140

Ser Thr Ser Leu Leu Gly Ser Ile Phe Pro Met Pro Arg Val Ile Tyr
145                 150                 155                 160

Ala Met Ala Glu Asp Gly Leu Leu Phe Lys Cys Leu Ala Gln Ile Asn
                165                 170                 175
```

-continued

```
Ser Lys Thr Lys Thr Pro Val Ile Ala Thr Leu Ser Ser Gly Ala Val
        180                 185                 190

Ala Ala Val Met Ala Phe Leu Phe Asp Leu Lys Ala Leu Val Asp Met
        195                 200                 205

Met Ser Ile Gly Thr Leu Met Ala Tyr Ser Leu Val Ala Ala Cys Val
    210                 215                 220

Leu Ile Leu Arg Tyr Gln Pro Gly Leu Cys Tyr Glu Gln Pro Lys Tyr
225                 230                 235                 240

Thr Pro Glu Lys Glu Thr Leu Glu Ser Cys Thr Asn Ala Thr Leu Lys
                245                 250                 255

Ser Glu Ser Gln Val Thr Met Leu Gln Gly Gln Gly Phe Ser Leu Arg
            260                 265                 270

Thr Leu Phe Ser Pro Ser Ala Leu Pro Thr Arg Gln Ser Ala Ser Leu
        275                 280                 285

Val Ser Phe Leu Val Gly Phe Leu Ala Phe Leu Ile Leu Gly Leu Ser
    290                 295                 300

Ile Leu Thr Thr Tyr Gly Val Gln Ala Ile Ala Arg Leu Glu Ala Trp
305                 310                 315                 320

Ser Leu Ala Leu Leu Ala Leu Phe Leu Val Leu Cys Ala Ala Val Ile
            325                 330                 335

Leu Thr Ile Trp Arg Gln Pro Gln Asn Gln Gln Lys Val Ala Phe Met
        340                 345                 350

Val Pro Phe Leu Pro Phe Leu Pro Ala Phe Ser Ile Leu Val Asn Ile
        355                 360                 365

Tyr Leu Met Val Gln Leu Ser Ala Asp Thr Trp Ile Arg Phe Ser Ile
    370                 375                 380

Trp Met Ala Leu Gly Phe Leu Ile Tyr Phe Ala Tyr Gly Ile Arg His
385                 390                 395                 400

Ser Leu Glu Gly Asn Pro Arg Asp Glu Glu Asp Glu Asp Ala Phe
            405                 410                 415

Ser Glu Asn Ile Asn Val Ala Thr Glu Glu Lys Ser Val Met Gln Ala
        420                 425                 430

Asn Asp His His Gln Arg Asn Leu Ser Leu Pro Phe Ile Leu His Glu
        435                 440                 445

Lys Thr Ser Glu Cys
    450
```

(2) INFORMATION FOR SEQ ID NO:7:

(i) SEQUENCE CHARACTERISTICS:
        (A) LENGTH: 2157 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 148..2034

(xi) SEQUENCE DESCRIPTION: SEQ ID NO:7:

```
CGATCCTGCC GGAGCCCCGC CGCCGCCGGC TTGGATTCTG AAACCTTCCT TGTATCCCTC      60

CTGAGACATC TTTGCTGCAA GATCGAGGCT GTCCTCTGGT GAGAAGGTGG TGAGGCTTCC     120

CGTCATATTC CAGCTCTGAA CAGCAAC ATG GGG TGC AAA GTC CTG CTC AAC ATT    174
                            Met Gly Cys Lys Val Leu Leu Asn Ile
                              5
```

-continued

| | | |
|---|---|---|
| GGG CAG CAG ATG CTG CGG CGG AAG GTG GTG GAC TGT AGC CGG GAG GAG<br>Gly Gln Gln Met Leu Arg Arg Lys Val Val Asp Cys Ser Arg Glu Glu<br>10                     15                    20                   25 | 222 |
| ACG CGG CTG TCT CGC TGC CTG AAC ACT TTT GAT CTG GTG GCC CTC GGG<br>Thr Arg Leu Ser Arg Cys Leu Asn Thr Phe Asp Leu Val Ala Leu Gly<br>               30                    35                    40 | 270 |
| GTG GGC AGC ACA CTG GGT GCT GGT GTC TAC GTC CTG GCT GGA GCT GTG<br>Val Gly Ser Thr Leu Gly Ala Gly Val Tyr Val Leu Ala Gly Ala Val<br>          45                    50                    55 | 318 |
| GCC CGT GAG AAT GCA GGC CCT GCC ATT GTC ATC TCC TTC CTG ATC GCT<br>Ala Arg Glu Asn Ala Gly Pro Ala Ile Val Ile Ser Phe Leu Ile Ala<br>             60                    65                    70 | 366 |
| GCG CTG GCC TCA GTG CTG GCT GGC CTG TGC TAT GGC GAG TTT GGT GCT<br>Ala Leu Ala Ser Val Leu Ala Gly Leu Cys Tyr Gly Glu Phe Gly Ala<br>75                     80                    85 | 414 |
| CGG GTC CCC AAG ACG GGC TCA GCT TAC CTC TAC AGC TAT GTC ACC GTT<br>Arg Val Pro Lys Thr Gly Ser Ala Tyr Leu Tyr Ser Tyr Val Thr Val<br>90                     95                   100               105 | 462 |
| GGA GAG CTC TGG GCC TTC ATC ACC GGC TGG AAC TTA ATC CTC TCC TAC<br>Gly Glu Leu Trp Ala Phe Ile Thr Gly Trp Asn Leu Ile Leu Ser Tyr<br>                    110                 115               120 | 510 |
| ATC ATC GGT ACT TCA AGC GTA GCG AGG GCC TGG AGC GCC ACC TTC GAC<br>Ile Ile Gly Thr Ser Ser Val Ala Arg Ala Trp Ser Ala Thr Phe Asp<br>          125                    130                    135 | 558 |
| GAG CTG ATA GGC AGA CCC ATC GGG GAG TTC TCA CGG ACA CAC ATG ACT<br>Glu Leu Ile Gly Arg Pro Ile Gly Glu Phe Ser Arg Thr His Met Thr<br>             140                    145                  150 | 606 |
| CTG AAC GCC CCC GGC GTG CTG GCT GAA AAC CCC GAC ATA TTC GCA GTG<br>Leu Asn Ala Pro Gly Val Leu Ala Glu Asn Pro Asp Ile Phe Ala Val<br>155                      160                    165 | 654 |
| ATC ATA ATT CTC ATC TTG ACA GGA CTT TTA ACT CTT GGT GTG AAA GAG<br>Ile Ile Ile Leu Ile Leu Thr Gly Leu Leu Thr Leu Gly Val Lys Glu<br>170                      175                    180                   185 | 702 |
| TCG GCC ATG GTC AAC AAA ATA TTC ACT TGT ATT AAC GTC CTG GTC CTG<br>Ser Ala Met Val Asn Lys Ile Phe Thr Cys Ile Asn Val Leu Val Leu<br>             190                    195                  200 | 750 |
| GGC TTC ATA ATG GTG TCA GGA TTT GTG AAA GGA TCG GTT AAA AAC TGG<br>Gly Phe Ile Met Val Ser Gly Phe Val Lys Gly Ser Val Lys Asn Trp<br>          205                    210                    215 | 798 |
| CAG CTC ACG GAG GAG GAT TTT GGG AAC ACA TCA GGC CGT CTC TGT TTG<br>Gln Leu Thr Glu Glu Asp Phe Gly Asn Thr Ser Gly Arg Leu Cys Leu<br>             220                    225                  230 | 846 |
| AAC AAT GAC ACA AAA GAA GGG AAG CCC GGT GTT GGT GGA TTC ATG CCC<br>Asn Asn Asp Thr Lys Glu Gly Lys Pro Gly Val Gly Gly Phe Met Pro<br>235                      240                    245 | 894 |
| TTC GGG TTC TCT GGT GTC CTG TCG GGG GCA GCG ACT TGC TTC TAT GCC<br>Phe Gly Phe Ser Gly Val Leu Ser Gly Ala Ala Thr Cys Phe Tyr Ala<br>250                      255                    260               265 | 942 |
| TTC GTG GGC TTT GAC TGC ATC GCC ACC ACA GGT GAA GAG GTG AAG AAC<br>Phe Val Gly Phe Asp Cys Ile Ala Thr Thr Gly Glu Glu Val Lys Asn<br>             270                    275                  280 | 990 |
| CCA CAG AAG GCC ATC CCC GTG GGG ATC GTG GCG TCC CTC TTG ATC TGC<br>Pro Gln Lys Ala Ile Pro Val Gly Ile Val Ala Ser Leu Leu Ile Cys<br>          285                    290                    295 | 1038 |
| TTC ATC GCC TAC TTT GGG GTG TCG GCT GCC CTC ACG CTC ATG ATG CCC<br>Phe Ile Ala Tyr Phe Gly Val Ser Ala Ala Leu Thr Leu Met Met Pro<br>             300                    305                  310 | 1086 |
| TAC TTC TGC CTG GAC AAT AAC AGC CCC CTG CCC GAC GCC TTT AAG CAC<br>Tyr Phe Cys Leu Asp Asn Asn Ser Pro Leu Pro Asp Ala Phe Lys His<br>315                      320                    325 | 1134 |

-continued

```
GTG GGC TGG GAA GGT GCC AAG TAC GCA GTG GCC GTG GGC TCC CTC TGC      1182
Val Gly Trp Glu Gly Ala Lys Tyr Ala Val Ala Val Gly Ser Leu Cys
330             335                 340                 345

GCT CTT TCC GCC AGT CTT CTA GGT TCC ATG TTT CCC ATG CCT CGG GTT      1230
Ala Leu Ser Ala Ser Leu Leu Gly Ser Met Phe Pro Met Pro Arg Val
                350                 355                 360

ATC TAT GCC ATG GCT GAG GAT GGA CTG CTA TTT AAA TTC TTA GCC AAC      1278
Ile Tyr Ala Met Ala Glu Asp Gly Leu Leu Phe Lys Phe Leu Ala Asn
            365                 370                 375

GTC AAT GAT AGG ACC AAA ACA CCA ATA ATC GCC ACA TTA GCC TCG GGT      1326
Val Asn Asp Arg Thr Lys Thr Pro Ile Ile Ala Thr Leu Ala Ser Gly
        380                 385                 390

GCC GTT GCT GCT GTG ATG GCC TTC CTC TTT GAC CTG AAG GAC TTG GTG      1374
Ala Val Ala Ala Val Met Ala Phe Leu Phe Asp Leu Lys Asp Leu Val
    395                 400                 405

GAC CTC ATG TCC ATT GGC ACT CTC CTG GCT TAC TCG TTG GTG GCT GCC      1422
Asp Leu Met Ser Ile Gly Thr Leu Leu Ala Tyr Ser Leu Val Ala Ala
410                 415                 420                 425

TGT GTG TTG GTC TTA CGG TAC CAG CCA GAG CAG CCT AAC CTG GTA TAC      1470
Cys Val Leu Val Leu Arg Tyr Gln Pro Glu Gln Pro Asn Leu Val Tyr
                430                 435                 440

CAG ATG GCC AGT ACT TCC GAC GAG TTA GAT CCA GCA GAC CAA AAT GAA      1518
Gln Met Ala Ser Thr Ser Asp Glu Leu Asp Pro Ala Asp Gln Asn Glu
            445                 450                 455

TTG GCA AGC ACC AAT GAT TCC CAG CTG GGG TTT TTA CCA GAG GCA GAG      1566
Leu Ala Ser Thr Asn Asp Ser Gln Leu Gly Phe Leu Pro Glu Ala Glu
        460                 465                 470

ATG TTC TCT TTG AAA ACC ATA CTC TCA CCC AAA AAC ATG GAG CCT TCC      1614
Met Phe Ser Leu Lys Thr Ile Leu Ser Pro Lys Asn Met Glu Pro Ser
    475                 480                 485

AAA ATC TCT GGG CTA ATT GTG AAC ATT TCA ACC AGC CTT ATA GCT GTT      1662
Lys Ile Ser Gly Leu Ile Val Asn Ile Ser Thr Ser Leu Ile Ala Val
490                 495                 500                 505

CTC ATC ATC ACC TTC TGC ATT GTG ACC GTG CTT GGA AGG GAG GCT CTC      1710
Leu Ile Ile Thr Phe Cys Ile Val Thr Val Leu Gly Arg Glu Ala Leu
                510                 515                 520

ACC AAA GGG GCG CTG TGG GCA GTC TTT CTG CTC GCA GGG TCT GCC CTC      1758
Thr Lys Gly Ala Leu Trp Ala Val Phe Leu Leu Ala Gly Ser Ala Leu
            525                 530                 535

CTC TGT GCC GTG GTC ACG GGC GTC ATC TGG AGG CAG CCC GAG AGC AAG      1806
Leu Cys Ala Val Val Thr Gly Val Ile Trp Arg Gln Pro Glu Ser Lys
        540                 545                 550

ACC AAG CTC TCA TTT AAG GTT CCC TTC CTG CCA GTG CTC CCC ATC CTG      1854
Thr Lys Leu Ser Phe Lys Val Pro Phe Leu Pro Val Leu Pro Ile Leu
    555                 560                 565

AGC ATC TTC GTG AAC GTC TAT CTC ATG ATG CAG CTG GAC CAG GGC ACC      1902
Ser Ile Phe Val Asn Val Tyr Leu Met Met Gln Leu Asp Gln Gly Thr
570                 575                 580                 585

TGG GTC CGG TTT GCT GTG TGG ATG CTG ATA GGC TTC ATC ATC TAC TTT      1950
Trp Val Arg Phe Ala Val Trp Met Leu Ile Gly Phe Ile Ile Tyr Phe
                590                 595                 600

GGC TAT GGC CTG TGG CAC AGC GAG GAG GCG TCC CTG GAT GCC GAC CAA      1998
Gly Tyr Gly Leu Trp His Ser Glu Glu Ala Ser Leu Asp Ala Asp Gln
            605                 610                 615

GCA AGG ACT CCT GAC GGC AAC TTG GAC CAG TGC AAG TGACGCACAG           2044
Ala Arg Thr Pro Asp Gly Asn Leu Asp Gln Cys Lys
        620                 625

CCCCGCCCCC CGGAGGTGGC AGCAGCCCCG AGGGACGCCC CCAGAGGACC GGGAGGCACC    2104
```

CCACCCTCCC CACCAGTGCA ACAGAAACCA CCTGCGTCCA CACCCTCACT GCA    2157

(2) INFORMATION FOR SEQ ID NO:8:

(i) SEQUENCE CHARACTERISTICS:
        (A) LENGTH: 629 amino acids
        (B) TYPE: amino acid
        (D) TOPOLOGY: linear (ii) MOLECULE TYPE: protein (xi) SEQUENCE DESCRIPTION: SEQ ID NO:8:

```
Met Gly Cys Val Leu Leu Asn Ile Ile Gly Gln Gln Met Leu Arg Arg
                 5                  10                  15

Lys Val Val Asp Cys Ser Arg Glu Glu Thr Arg Leu Ser Arg Cys Leu
             20                  25                  30

Asn Thr Phe Asp Leu Val Ala Leu Gly Val Gly Ser Thr Leu Gly Ala
             35                  40                  45

Gly Val Tyr Val Leu Ala Gly Ala Val Ala Arg Glu Asn Ala Gly Pro
         50                  55                  60

Ala Ile Val Ile Ser Phe Leu Ile Ala Ala Leu Ala Ser Val Leu Ala
 65                  70                  75                  80

Gly Leu Cys Tyr Gly Glu Phe Gly Ala Arg Val Pro Lys Thr Gly Ser
                 85                  90                  95

Ala Tyr Leu Tyr Ser Tyr Val Thr Val Gly Glu Leu Trp Ala Phe Ile
            100                 105                 110

Thr Gly Trp Asn Leu Ile Leu Ser Tyr Ile Ile Gly Thr Ser Ser Val
            115                 120                 125

Ala Arg Ala Trp Ser Ala Thr Phe Asp Glu Leu Ile Gly Arg Pro Ile
        130                 135                 140

Gly Glu Phe Ser Arg Thr His Met Thr Leu Asn Ala Pro Gly Val Leu
145                 150                 155                 160

Ala Glu Asn Pro Asp Ile Phe Ala Val Ile Ile Leu Ile Leu Leu Thr
                165                 170                 175

Gly Leu Leu Thr Leu Gly Val Lys Glu Ser Ala Met Val Asn Lys Ile
            180                 185                 190

Phe Thr Cys Ile Asn Val Leu Val Leu Gly Phe Ile Met Val Ser Gly
            195                 200                 205

Phe Val Lys Gly Ser Val Lys Asn Trp Gln Leu Thr Glu Glu Asp Phe
        210                 215                 220

Gly Asn Thr Ser Gly Arg Leu Cys Leu Asn Asn Asp Thr Lys Glu Gly
225                 230                 235                 240

Lys Pro Gly Val Gly Gly Phe Met Pro Phe Gly Phe Ser Gly Val Leu
                245                 250                 255

Ser Gly Ala Ala Thr Cys Phe Tyr Ala Phe Val Gly Phe Asp Cys Ile
            260                 265                 270

Ala Thr Thr Gly Glu Glu Val Lys Asn Pro Gln Lys Ala Ile Pro Val
            275                 280                 285

Gly Ile Val Ala Ser Leu Leu Ile Cys Phe Ile Ala Tyr Phe Gly Val
        290                 295                 300

Ser Ala Ala Leu Thr Leu Met Met Pro Tyr Phe Cys Leu Asp Asn Asn
305                 310                 315                 320

Ser Pro Leu Pro Asp Ala Phe Lys His Val Gly Trp Glu Gly Ala Lys
                325                 330                 335

Tyr Ala Val Ala Val Gly Ser Leu Cys Ala Leu Ser Ala Ser Leu Leu
            340                 345                 350
```

Gly Ser Met Phe Pro Met Pro Arg Val Ile Tyr Ala Met Ala Glu Asp
            355                 360                 365

Gly Leu Leu Phe Lys Phe Leu Ala Asn Val Asn Asp Arg Thr Lys Thr
        370                 375                 380

Pro Ile Ile Ala Thr Leu Ala Ser Gly Ala Val Ala Ala Val Met Ala
385                 390                 395                 400

Phe Leu Phe Asp Leu Lys Asp Leu Val Asp Leu Met Ser Ile Gly Thr
                405                 410                 415

Leu Leu Ala Tyr Ser Leu Val Ala Ala Cys Val Leu Val Leu Arg Tyr
            420                 425                 430

Gln Pro Glu Gln Pro Asn Leu Val Tyr Gln Met Ala Ser Thr Ser Asp
        435                 440                 445

Glu Leu Asp Pro Ala Asp Gln Asn Glu Leu Ala Ser Thr Asn Asp Ser
    450                 455                 460

Gln Leu Gly Phe Leu Pro Glu Ala Glu Met Phe Ser Leu Lys Thr Ile
465                 470                 475                 480

Leu Ser Pro Lys Asn Met Glu Pro Ser Lys Ile Ser Gly Leu Ile Val
                485                 490                 495

Asn Ile Ser Thr Ser Leu Ile Ala Val Leu Ile Ile Thr Phe Cys Ile
            500                 505                 510

Val Thr Val Leu Gly Arg Glu Ala Leu Thr Lys Gly Ala Leu Trp Ala
        515                 520                 525

Val Phe Leu Leu Ala Gly Ser Ala Leu Leu Cys Ala Val Val Thr Gly
    530                 535                 540

Val Ile Trp Arg Gln Pro Glu Ser Lys Thr Lys Leu Ser Phe Lys Val
545                 550                 555                 560

Pro Phe Leu Pro Val Leu Pro Ile Leu Ser Ile Phe Val Asn Val Tyr
                565                 570                 575

Leu Met Met Gln Leu Asp Gln Gly Thr Trp Val Arg Phe Ala Val Trp
            580                 585                 590

Met Leu Ile Gly Phe Ile Ile Tyr Phe Gly Tyr Gly Leu Trp His Ser
        595                 600                 605

Glu Glu Ala Ser Leu Asp Ala Asp Gln Ala Arg Thr Pro Asp Gly Asn
    610                 615                 620

Leu Asp Gln Cys Lys
625

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

AAAGAAGGGA AGTACGGTGT TGGTGG                                      26

(2) INFORMATION FOR SEQ ID NO:10:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

ACACAAAAGA AGTGAAGTAC GGTGTTGGTG G　　　　　　　　　　　　　　　　　　　31

(2) INFORMATION FOR SEQ ID NO:11:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

AATGACACAA AAAACGTGAA GTACGGTGTT GGTGG　　　　　　　　　　　　　　　　35

(2) INFORMATION FOR SEQ ID NO:12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

AAAGAAGGGA AGTACGGTGA GGGTGGATTC ATG　　　　　　　　　　　　　　　　　33

(2) INFORMATION FOR SEQ ID NO:13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

TGAAGTACGG TGTTGGTGGA TTCATG　　　　　　　　　　　　　　　　　　　　　26

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

ACACAAAAGA AGTGAAGTAC GGTGA　　　　　　　　　　　　　　　　　　　　　25

(2) INFORMATION FOR SEQ ID NO:15:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

```
AATGACACAA AAAACGTGAA GTACGGTGA                                              29

(2) INFORMATION FOR SEQ ID NO:16:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

AACAATGACA CAAACGTGAA GTACGGTGAG GGTGGATTCA TG                               42

(2) INFORMATION FOR SEQ ID NO:17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

GGTGGCGATG CAGTCAA                                                          17

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

TCAGCCATGG CATAGATA                                                         18

(2) INFORMATION FOR SEQ ID NO:19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

AAGGCTCCGT TAAAAAC                                                          17

(2) INFORMATION FOR SEQ ID NO:20:

(i) SEQUENCE CHARACTERISTICS:
        (A) LENGTH:  28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

TACAGGAGAA ATCTTCCTCC GTGAGCTG                                              28

(2) INFORMATION FOR SEQ ID NO:21:
```

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:21:

GAGAAAAATT TCGGCAACTG TAACAACAAC                30

(2) INFORMATION FOR SEQ ID NO:22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

AAAAATTTCT CCCGTCTCTG TAACAACAAC                30

(2) INFORMATION FOR SEQ ID NO:23:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

AATTTCTCCT GTTTCAACAA CGACAC                    26

(2) INFORMATION FOR SEQ ID NO:24:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

TCACCGTATT TCCCTTCTGT GTCGTTGTT                 29

(2) INFORMATION FOR SEQ ID NO:25:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

ACAAACGTGA AACCCGGTGT GGGAGGGTTT AT             32

(2) INFORMATION FOR SEQ ID NO:26:

(i) SEQUENCE CHARACTERISTICS:
        (A) LENGTH: 26 base pairs
        (B) TYPE: nucleic acid (C) STRANDEDNESS: single
        (D) TOPOLOGY: linear (ii) MOLECULE TYPE: DNA (xi) SEQUENCE DESCRIPTION: SEQ ID NO:26:

ACAAACGTGA AACCCGGTGA GGGAGG                                                26

(2) INFORMATION FOR SEQ ID NO:27:

(i) SEQUENCE CHARACTERISTICS:
        (A) LENGTH:   17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

ATACGGTGTG GGAGGGT                                                          17

(2) INFORMATION FOR SEQ ID NO:28:

(i) SEQUENCE CHARACTERISTICS:
        (A) LENGTH:   27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

TCTGCCTGGA CAACAACAGC CCGCTGC                                               27

(2) INFORMATION FOR SEQ ID NO:29:

(i) SEQUENCE CHARACTERISTICS:
        (A) LENGTH:   26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

GCCCGCTGCC TGACGCCTTC AAGCAC                                                26

(2) INFORMATION FOR SEQ ID NO:30:

(i) SEQUENCE CHARACTERISTICS:
        (A) LENGTH:   38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

GCCTTCAAGC ACGTGGGCTG GGAAGGAGCT AAGTACGC                                   38

(2) INFORMATION FOR SEQ ID NO:31:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA

```
(xi) SEQUENCE DESCRIPTION: SEQ ID NO:31:

GCCTTCAAGC ACGTGGGCTG GGAAGGAGCT AAGTACGC                              38
```

US 7,071,301 B1

CHIMERIC VIRAL RECEPTOR POLYPEPTIDES, HUMAN VIRAL RECEPTOR POLYPEPTIDES AND USES THEREOF

CROSS-REFERENCE TO RELATED APPLICATIONS

The present application is a continuation-in-part of U.S. Ser. No. 08/084,729, filed Jun. 29, 1993 now abandoned, which is a continuation-in-part of both international application PCT/US93/05569, filed Jun. 11, 1993, and U.S. Ser. No. 07/899,075, filed Jun. 11, 1992, which U.S. application is a continuation-in-part of U.S. Ser. No. 07/806,178, filed December 13, 1991, now abandoned, which is a continuation-in-part of U.S. Ser. No. 07/627,950, filed Dec. 14, 1990, now abandoned, the contents of each of said 08/084,729, US93/05569 and 07/899,075 applications being entirely incorporated herein by reference.

BACKGROUND OF THE INVENTION

1. Field of the Invention

The present invention, in the fields of virology and molecular biology, relates to nucleic acid, methods and polypeptides relating to target cell specific delivery of therapeutic and/or diagnostic agents by target cell specific delivery vectors. Target cells are made specific for such delivery vectors by their (i) association with a chimeric viral receptor polypeptide having a second virus host cell range different from the target cell viral host cell range and/or (iii) providing a delivery vector having a binding domain specific for the target cell.

2. Description of the Background Art

Cell specific delivery of therapeutic or diagnostic agents in animals and human patients has suffered from the problems of non-tissue specific delivery, detrimental side effects and lack of effective dosage delivered to the target cells. While the use of monoclonal antibodies as diagnostic agents, therapeutic agents or delivery vectors overcomes the problem of tissue specificity, monoclonal antibodies suffer from the problem of immunogenicity, as well as insufficient dosage, due to clearance of antibody and/or fragments thereof by the kidneys or liver.

As an alternative delivery vector, the use of recombinant viruses has been investigated to determine suitable delivery vectors for therapeutic or diagnostic agents.

Viruses infect a cell by first binding their viral binding domain to a cell at the cell's viral receptor. The viral binding domain of the virus binds the cell's viral receptor at the viral binding site. A number of virus-specific cellular receptors have been identified, and most of these viral receptors have other known cellular functions for the cell. The degree of expression of such viral binding receptors in cells is thus a strong determinant of susceptibility of these cells to viral infection. Binding to the viral receptor is required for fusion of the virus envelope protein (env) to the target cell at the cell surface. (White et al., *Quant. Rev. Biophys.* 16: 151–195 (1983)). After fusion of the viral binding domain via viral binding to the cell's viral receptor binding site, the viron core enters the cytoplasm of the bound cell and the viral replication process is initiated. In some cases viruses bound to their receptors can also enter cells by receptor mediated endocytosis, such as by some retroviruses.

Retroviruses may be classified by the range of species that they are able to infect. For example, the mouse type C retroviruses, which are used in genetic engineering, fall into five general classes: amphotropic, which exhibit the broadest host range, encompassing a diversity of mammalian species including humans and rodents; polytropic, which use a receptor distinct from that for amphotropic viruses and also exhibit a more restricted host range; 10A1, which use both the amphotropic receptor as well as a second, widely expressed, receptor (Ott, et al., *J. Virol* (1990), *J. Virol* 19:13–18 (1976)); xenotropic, which also have a wide mammalian species host range but cannot infect mouse cells; ecotropic, which infect only rodent species or any combination thereof. Of these five mouse retrovirus receptor classes, only the receptor for the ecotropic Moloney murine leukemia virus (MLV) (see, e.g., Albritton, et al., *Cell* 57:659–666 (1989) has been cloned.

Human cells have been characterized at having at least eight distinct receptors for retroviruses (Sommerfelt, et al., *Virology* 176:58–69 (1990)). Of these, at least two now been cloned: the receptor for human immunodeficiency virus, a lentivirus (Maddon, Cell 47:333–348 (1986), McDougal, et al., *Science* 231:382–285 (1986), and the receptor for gibbon ape leukemia virus, a type C Retrovirus (O'Hara, et al. *Cell Growth Differ.* 1:119–127 (1990). The receptor used by human immunodeficiency virus, the CD4 antigen, is similar to receptors used by a number of other viruses in that it is a member of the immunoglobulin superfamily of cell surface proteins. In contrast, the gibbon ape leukemia virus receptor is not an immunoglobulin-like protein (O'Hara, et al., *Cell Growth Differ.* 1:119–127 (1990)).

Although amphotropic mouse retroviruses have a broad tropism, there are restrictions to their host cell range, both phylogenetic and based on tissue distribution. While many human cell types are infectable by amphotropic murine retroviruses, cell lines derived from certain mammalian species tissues, (e.g., bovine kidney cell line MDBK and Chinese hamster ovary cell line CHO-K1), are not infectible et al., *J. Virol.* 19:19–25 (1976), Rasheed, et al., *J. Virol.* 19:13–18 (1976)). Other tissues, such as, but not limited to, human lymphoid cells, are also poorly infectable and express relatively low amounts of the receptor on their surfaces (Kadan, et al., *J. Virol.* 66:2281–2287 (1992).

A cDNA clone (termed W1) encoding a medium ecotropic retroviral receptor (ERR) (SEQ ID NO:4) was identified (Albritton, L. W. et al., *Cell* 57:659–666 (1989)). The ERR was postulated to be ecotropic murine specific viral receptor for the MuLV retrovirus.

Viral Receptor Mediated Tissue Specificity

Viral receptors can provide tissue specificity for susceptibility to viral infection by tissue specific expression of cell surface proteins that act as specific viral receptors. HIV is an example of a virus exhibiting receptor-mediated tissue restriction, apparently based on its use of the CD4 protein as its primary receptor. Cell receptor concentration is a predominant factor, e.g., the concentration of CD4 receptors on the surface of mouse NIH 3T3 cells is not sufficient to make these cells susceptible to infection by HIV.

The tea (T cell early activation, SEQ ID NO:5) gene, as exemplified by clone 20.5 of MacLeod et al. (*J. Biol. Chem.* 1:371–279 (1990)), was the first example of a cloned gene or cDNA that has the potential to encode a multiple transmembrane-spanning protein which is induced during T cell activation (Crabtree, *Science* 243:355–361 (1989)). The function of the tea gene is not yet known.

The sequence of 20.5 cDNA (SEQ ID NO:5) was found to be strikingly homologous to the murine ERR cDNA clone (SEQ ID NO:3) discussed above (Albritton, supra the Rec-1 gene). Retroviral binding and infection studies are required to determine whether the tea-encoded protein functions as a viral receptor (Rein et al., *Virology* 136:144–152 (1984)). Despite the high degree of similarity between tea and ERR, the two genes differ in chromosomal location, and their predicted protein products differ in tissue expression patterns.

Use of Viruses as Delivery Vectors

The investigation of how viruses replicate and how their genes code for viral proteins has lead to their use as engineered viral vectors for delivering DNA into cells, in vitro, or in situ for the purpose of expressing heterologous DNA in target cells. Thus, viral vectors have been used as delivery vectors to specifically infect and deliver potentially therapeutic or diagnostic DNA or RNA into target cells, based on the target cell specificity of the virus. Viruses have been found to have specific host ranges, termed viral host cell ranges, wherein the trophism of a particular virus is found to be species or tissue specific.

Such viral host cell ranges have been best characterized in the case of the Moloney murine luekemia virus (MLV) which has been most extensively used as a delivery vector for delivery of a heterologous nucleic acid into cells which correspond to the viral host cell range of the MLV. For example, ecotropic MLV will only infect certain types of mouse cells. However, amphotropic MLV as a broad host range, such that amphotropic MLV viruses also infect cells of species other than murine, such as, but not limited to, human.

Accordingly, amphotropic MLV has been most widely used in the laboratory to deliver specific human DNA sequences into target human cells or murine cells. However, to prevent viral replication and further infection in target cells, amphotropic MLV viral vectors have been modified by genetic engineering to be incapable of replicating, by deletion of nucleic acid encoding the env protein. Such engineered amphotrophic MLV have been proposed and preliminarily used to infect human cells in vitro. This MLV is also proposed to be used in vivo human gene therapy, but suffers potential problems of non-specific infection, reversion to replication, competence and/or cancer induction.

Gene Therapy and Gene Transfer

One in every hundred newborn children is born with a serious genetic disorder (Verma, *Sci. Amer.* 262:68–84 (1990). Often, the effect is accomplished by physical or mental abnormalities, pain and early death (Verma, supra). Because no effective therapies exist for most of the 4,000 known inherited disorders, gene therapists have long sought methods to introduce healthy genes into patients to replace defective genes, or simply to substitute their functions. Advances in recombinant DNA technology, which have made possible the isolation of many genes, as well as much progress in understanding gene regulation, have made this once remote goal possible in the near future. Indeed, over the past several years, the field has seen an enormous amount of progress.

Gene therapy is still in its infancy and many problems remain to be solved. Several areas need further study; such as, but not limited to, gene expression and safety as well as direct, targeted, in viro delivery. The development of vectors that can be safely and efficiently injected directly into patients is a problem that for which there has been a long felt need without suitable solutions. Gene therapy's impact will be limited so long as the technique is carried out as it is currently, where cells are removed from a patient, and the desired gene is transferred in vitro to these cells, which are then returned to the patient. The procedure is also very expensive, and requires too much scientific and medical expertise to be used extensively except in major medical centers (Anderson, W. F. *Science* 256:808–813 (1992)).

Gene therapy will have a major impact on health care only when vectors are developed that can be safely and efficiently injected directly into patients, a drugs like insulin are now (Anderson, W. F., supra). Vectors need to be discovered and developed that will target specific cell types, insert their genetic information into a safe site in the genome and be regulated by normal physiological signals (Anderson, W. F., supra).

One relatively efficient but problematic means for achieving transfer of genes is by amphotropic retrovirus-mediated gene transfer (see, e.g., Gilboa, E., *Bio-Essays* 5:252–258 (1987); Williams, D. A. et al., *Nature* 310:476–480 (1984); Weiss, R. A. et al., *RNA Tumor Viruses,* Cold Spring Harbor Laboratory Press, Cold Spring Harbor, New York, 1985). Recombinant amphotropic retroviruses have been used and studied for the possibility of being used as vectors for the transfer of genes into human cells (Cone, R. D. et al., *Proc. Natl. Acad. Sci. USA* 81:6349–6353 (1984); Danos, O. et al., *Proc. Natl. Acad. Sci. USA* 6460–6464 (1988)). Such amphotropic viruses, e.g., murine amphotropic MuLV, are capable of infecting human cells. One of the safety problems inherent in this approach which may preclude progress in the clinic, is the fact that even amphotropic retroviruses that have been rendered replication-defective are sometimes capable of generating wild-type variants through recombinational events which provide replication ability (see, e.g., Thompson, *Science* 257–1854 (1992)). Such an alteration could lead to the widespread retroviral infection in cells and tissues which were not intended to be genetically modified, (Mulligan, *Science* 257:1854, 1937). Generalized disease could result, such as, but not limited to, cancer or other pathologies caused by insertion of the amphotropic virus' nucleic acid with the LTR's into important functioning genes within a cell which disruption could lead to a pathologic state (Mulligan, R., *Science,* 260:926 (1993). It is to these needs and problems that the present invention is also directed.

Accordingly, there is a need to overcome one or more problems associated with the use of known retroviruses or other viral vectors for introducing heterologous genes into eukaryotic cells. There is also a need to provide viral receptor proteins which bind viruses and which can be used in diagnostic and/or therapeutic applications without known problems, such as, but not limited to, immunogenicity, blood clearance and non-specific cell binding found with the present use of murine amphotropic viruses.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention is intended to overcome one or more deficiencies of the related background art.

The present invention also provides new and/or improved diagnostic/therapeutic methods for target cell delivery of diagnostic/therapeutic agents, such as, but not limited to, gene therapy. The target cell delivery is provided by the use of novel target cell receptors and/or target cell specific delivery vectors. Such delivery vectors of this invention deliver the diagnostic/therapeutic agent to a target cell in vitro, in situ, or in vivo, utilizing the mechanisms of modification of a binding site of a target cell receptor and/or modification of a binding domain on delivery vector.

Accordingly, delivery vectors of the present invention are substantially specific only for target cells and not for other cells of the tissue or animal which has administered the diagnostic/therapeutic agent.

A CVR polypeptide is alternatively or additionally provided having at least 80% (e.g., 80–99%, or any range or value therein) homology to a human amphotropic, polytropic, xenotropic, ecotropic and/or tissue specific first viral binding site with substituted, deleted, or added amino acid residues corresponding to residues of second virus receptor binding site having a second virus host cell range binding site, to confer binding to the second virus host cell range.

A CVR polypeptide is alternatively or additionally provided in soluble form and/or optionally further comprising a surrogate binding domain or an antibody sequence capable of binding a viral env. protein, having the same or different viral host cell range.

A CVR polypeptide is also provided, optionally further comprising at least one transmembrane domain of a viral receptor, or a fusion protein thereof, which contains the variable/constant light peptide chains of an antibody against a second virus host cell range env binding domain.

The present invention also provides a CVR polypeptide substituted by an antibody specific for a second vira env binding domain corresponding to the binding domain of the delivery vector, wherein the antibody to the second env binding domain binds a viral host cell range that is different from the target cell and/or the viral host range of the animal from which the target cell is derived.

Nucleic acid coding for, cells or tissues expressing, such a CVR or viral receptor polypeptide are also provided by the present invention.

The viral host cell range of a first or second env binding domain may include a species host cell range, e.g., at least one of amphotropic, polytropic, xenotropic and ecotropic of any mammal, human and non-human, or a tissue specific host range, e.g., at least one of any tissue type having a tissue specific viral receptor, including a CVR polypeptide having a binding site specific for a virus having a tissue specific host cell range.

Virus types which are non-limiting examples of viruses corresponding to a second virus having a second virus host cell range are mammalian leukemia viruses, adenovirus, adenovirus associated virus, herpes virus, and tissue specific viruses, such as, but not limited to, rabies virus (neuronal tissue), Borna disease virus (BDV) Epstein-Barr virus (EBV) (human B-cells, CD21 receptor oral mucosa), reovirus type 3 (neurons and glia) (fibroblast and thykoma cells); lymphocytic chloriomeningitis virus (LCMV) (F-cell receptors); Poliovirus (liver cells); hepatitis B (hepatocytes, fibroblasts, blood mononuclear cells); human papilloma virus-16 (HPV-16); HIV (human brain 60 kd protein CDM on T-cells; reovirus (neuronal and lymphoid); sendai virus (gangliosides, brain tissue). Tumor specific receptors are also included.

Functional derivatives of chimeric polypeptides, muteins of chimeric polypeptides, and fragments of chimeric polypeptides are also provided according to the present invention.

The present invention is therefore intended to include all compounds, compositions, and methods of making and using such CVR polypeptides, without undue experimentation, based on the teachings and guidance presented herein. The invention also is intended to provide nucleic acid coding for, and/or cells or tissues expressing, such a chimeric receptor polypeptide or delivery vector.

Viral binding activity and other known methods are provided for screening for activity of CVR polypeptides or delivery vectors of the present invention.

Therapeutic and/or diagnostic agents/compositions for delivery to chimeric cells of the present invention are also provided which include CVR specific or tissue specific receptor ligands containing delivery vectors further comprising; (a) nucleic acids which code for protein or which affect transcription, translation, or post-transcription events; (b) labeled diagnostic biologically active proteins (such as, but not limited to, an enzyme) therapeutic protein; (c) normal protein; (d) toxin; (e) growth-factor; (f) cytokine or (g) a labeled diagnostic or therapeutic.

Chemical compounds may also be used as therapeutic/diagnostic agents with CVR or receptor specific delivery vectors in conjunction with a target cell having an associated CVR polypeptide. A CVR polypeptide antibody or target cell specific receptor ligand may also be provided as a pharmaceutical composition as part of the delivery vector.

Therapeutic administration is provided utilizing a delivery vector, chimeric receptor and/or delivery vector specific ligand of the present invention. Diagnostic assays are also provided, such as, but not limited to, methods for evaluating the presence and/or the level of normal or CVR polypeptide or viral receptor, or encoding nucleic acid in a subject.

Chimeric or human viral receptor specific antibodies and methods are also provided according to the present invention. An antibody or fragment specific for an epitope of a human or chimeric viral receptor polypeptide can be made by hybridoma technology, genetic engineering and/or chemical synthesis.

The present invention also provides antibody (Ab) and methods to inhibit viral infection, viability, replication or binding of a human cell or tissue, in vivo or in vitro or in situ. Such Abs can be used to prevent and/or treat retrovirus infection, and/or detect the presence of, and/or measure the quantity or concentration of, a chimeric viral receptor polypeptide or chimeric viral receptor polypeptide in a cell, or in a cell or tissue extract, or a biological fluid.

Antibody diagnostic assays are also provided, such as, but not limited to, utilizing labeled antibodies, fragments or derivatives thereof, which may be used to quantitatively or qualitatively detect the presence of cells which express a CVR polypeptide or viral receptor polypeptide or second env binding domain ligand, on their surface or intracellularly. Sample detection/support/labeling is also provided.

Transgenic and chimeric non-human mammals are also provided, comprising nucleic acid encoding, or protein, corresponding to, at least a viral binding site of a CVR polypeptide, second env binding domain, ligand and tissue specific second viral receptor.

Other objects, features and advantages of the present invention will become apparent to those skilled in the art from the following detailed description. It should be understood however, that the detailed description and specific examples, while indicating preferred embodiments of the present invention, are given by way of illustration and not of limitation. Many changes and/or modifications within the scope of the present invention may be made without departing from the spirit thereof, and the invention includes all such changes and/or modifications.

BRIEF DESCRIPTION OF THE DRAWINGS

FIG. 1 shows the H13 nucleic acid sequence (SEQ ID NO:7), including coding and non-coding sequences, and the predicted protein sequence (SEQ ID NO:8) of the H13 protein.

FIG. 2 shows a schematic diagram of the alignment of one strand of the H13 and ERR cDNA sequence (SEQ ID NOS:7 and 3, respectively). The sequences were analyzed using the Genetics computer group sequence analysis software package (Devereus, J. et al., *Nucl. Acids Res.* 12:387–395 (1984)).

FIG. 3 shows the alignment of H13, ERR and TEA deduced amino acid sequences. Vertical lines indicate sequence homology. Dots indicate lack of homology and double dots representing conservative amino acid changes. The sequences were analyzed as in FIG. 2. Shown in brackets are the sequences of H13 corresponding to Extracellular Domain 3 (residues 210–249) and Extracellular Domain 4 (residues 310–337).

FIG. 12A–B shows the genetic mapping of the H13 gene to human chromosome 13. The autoradiogram (FIG. 12A) shows the hybridization pattern of EcoRI-digested nucleic acid from human-hamster somatic cell hybrids probed with H13 CDNA (SEQ ID NO:1). Lane 1 and 11 contain nucleic acid from human and hamster, respectively. Lanes 2–10 contain nucleic acid which is derived from the chromosomes as designated in the table in FIG. 12B.

FIG. 14 shows a comparison of sequences (nucleotide and amino acid) of the region of H13 and ERR termed Extracellular Domain 3 (as also depicted as part of SEQ ID NO:7, SEQ ID NO:8 and FIG. 1). This region of the receptor protein is the most diverse between the human and mouse sequences. The sequences were aligned using Genetics computer group sequence analysis software package (See, e.g., Devereux, J. et al., *Nucl. Acids Res.* 12:387–395 (1984)).

FIG. 17 shows a comparison of nucleotide and amino acid sequence of extracellular domains 3 and 4 in murine ERR and human H13. The alignment was made using the Genetics computer group sequence analysis software package (See, e.g., Devereux et al *Nucleic Acids Res.* 12:387–395 (1984)). To pinpoint the critical amino acid residues, oligonucleotide-directed mutagenesis was carried out and 13 individual mutant ERR molecules were created with contain one or two amino acids substitutions or insertions as marked by boxes.

FIG. 20 shows an amino acid and nucleic acid comparison of the N-terminal env region of the ecotropic Akv and amphotropic MLV 4070A, which contains a 30 amino acid gap within the amphotropic sequence. Nucleotide sequence and corresponding amino acids are shown. Akv sequence Genbank Accession number V01164 Amphotrophic MLB 4070 Genbank Accession number mm469. Numbers above indicate nucleotide positions in reported sequences. Numbers below indicate amino acid positions (see FIG. 4). The positions of Akv SmaI and Amph. RsaI restriction sites are also shown. Nucleotide sequences suitable for PCR primers are indicated by arrows.

DETAILED DESCRIPTION OF THE PREFERRED EMBODIMENTS

Figure 4:
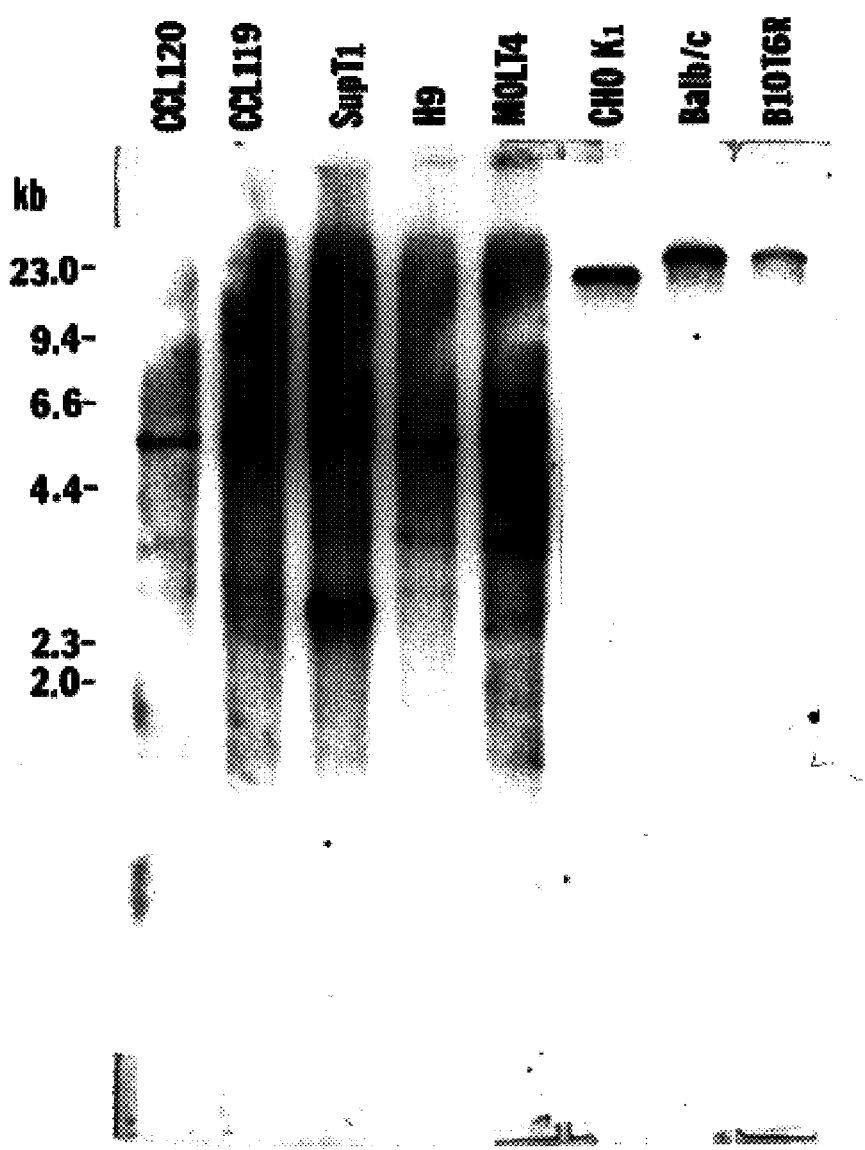
FIG. 4 shows an autoradiogram of the hybridization pattern of EcoRI-digested nucleic acid of human (CCL120, CCL119, SupT1, H9, MOLT4), Hamster (CHO-K1) and mouse (Balb/c thymocytes, BIOT6R) origin, probed with the KpnI—KpnI fragment (390 bp) of murine ERR CDNA.
Figure 5:
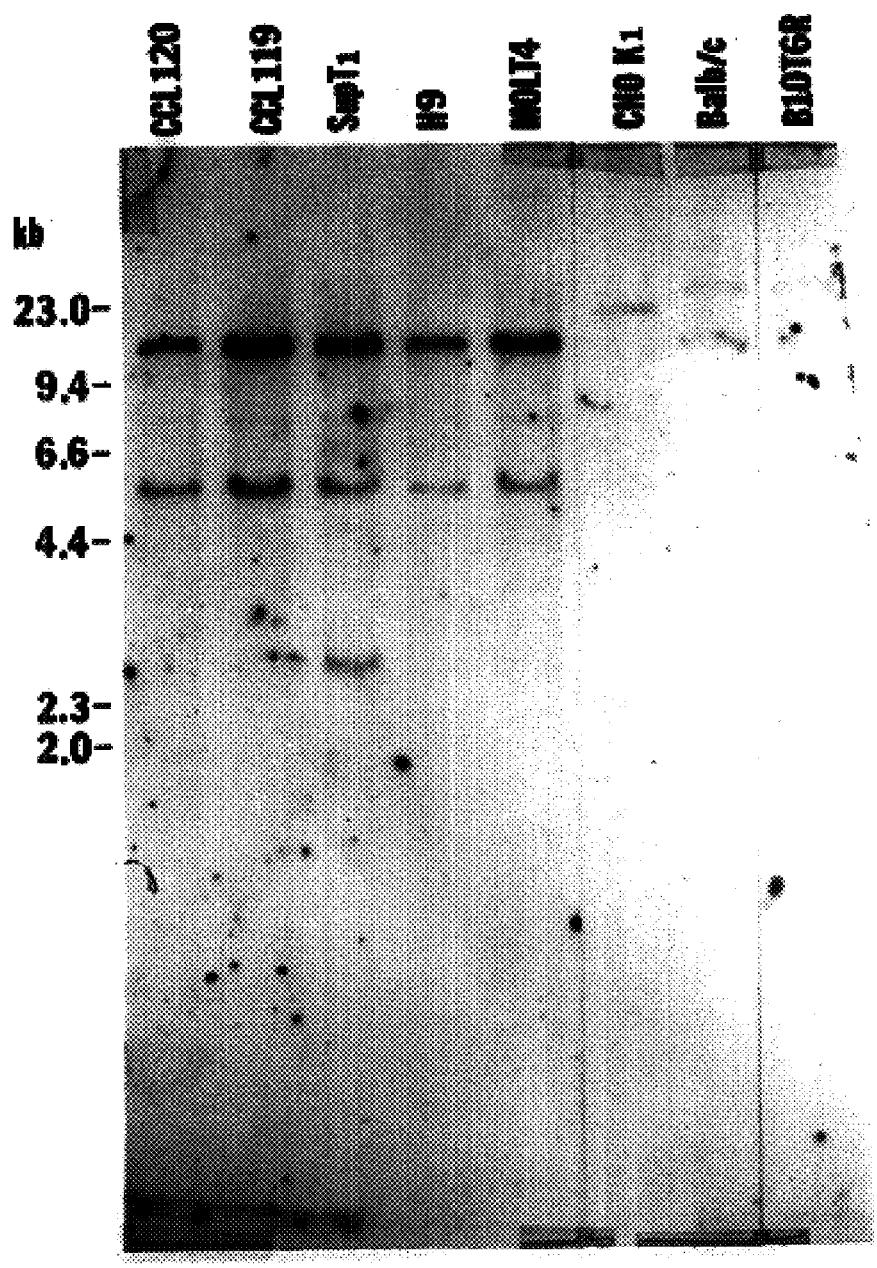
FIG. 5 shows an autoradiogram of a Southern blot analysis nucleic acid from various species with H13 CDNA (SEQ ID NO:1). Nucleic acid hybridized was EcoRI-digested nucleic acid of human (CCL120, CCL 119, SupT1, H9, MOLT4), hamster (CHO-K1) or mouse thymocyces (Balb/c or BIOT6R) origin.

A long felt need in the field of diagnostic/therapeutic methods has been target cell specific delivery of diagnostic/therapeutic agents. Diagnostic/therapeutic agents can be administered to a patient by the use of delivery vectors which facilitate delivery to the target cell, such as, but not limited to, monoclonal antibodies, liposomes, glycans, proteins and other carriers, by protecting the agent from degradation, reducing immuno-genicity and/or by preferentially associating with the target cell.

However, present methods suffer from the problems such as non-target cell delivery of the diagnostic/therapeutic agent, immunogenicity of the agent, lack of effective concentration of agent as target cells, and detrimental side effects, such as pathological states in non-target cells.

The present invention meets this long felt need by providing target cell specific delivery of a diagnostic/therapeutic agent with increased specificity and decreased non-target cell delivery, decreased immunogenicity, effective concentration at the target cell and decreased side effects.

The present invention is based on the discovery that viral receptors are present on particular cell types in animals (e.g., humans) have specific binding sites for various types of viruses having specific host cell ranges, which receptors can be cloned, isolated and/or sequenced. Since different types of viruses have different host cell ranges, it is also now discovered that animal, such as, but not limited to, human, binding sites on target cells can be engineered to bind viruses having a non-target cell, viral host cell range.

The utility of the present invention thus may comprise the modification of human viral receptors to allow target cell specific binding of delivery vectors of therapeutic and/or diagnostic agents.

Based on the above discovery that viral receptors can be modified to bind different viral binding domains of different viral host ranges, the viral vector, as a delivery vector, can also be modified to have a binding domain specific for a target cell. Methods and compositions of the present invention can thus provide target cell delivery of at least one therapeutic and/or diagnostic agent via a delivery vector made specific for the target cell by (a) modification of a delivery vector binding domain to become target cell specific, (b) by modification of a cell viral receptor binding site to bind substantially only to the target cell.

In modification, a target cell specificity of delivery vectors is provided in one aspect of the present invention, by modification of the delivery vector to incorporate a target cell specific binding domain, using any molecule or combination which associates with unique specificity to a binding site on the target cell.

As a non-limiting example of modification (a) of the delivery vector binding domain, the binding domain is engineered to have a unique specificity for the target cell, such as, but not limited to, incorporation of a target cell specific ligand. A non-limiting sub-example of such incorporation is the use of an anti-HIV delivery vector as a toxin/viral vector. The viral vector has its viral receptor binding domain replaced by an anti-HIV-gp120 antibody fragment and toxin. The resulting delivery vector is specific for HIV infected T-cells as target cells, and specifically kills these T-cells.

Alternatively, in modification (b) a target cell receptor is altered in the present invention to be made specific for a delivery vector by association of the target cell with a delivery vector binding site specific for the delivery vector, where the delivery vector cannot bind to cells or tissues other than the modified target cell. The binding site may comprise at least one chimeric viral receptor (CVR) polypeptide which comprises a chimeric receptor binding site specific for the binding domain of the delivery vector.

A CVR polypeptide of the present invention can be provided as an isolated, recombinant and/or synthesized polypeptide which confers on the target cell binding specificity for the delivery vector. The binding specificity of the CVR polypeptide is provided by a chimeric virus binding site which is specific for a second viral binding domain of a second virus. The second virus has a second viral host cell range different from a first viral host cell range of the target cell and/or other cells of the animal from which the target cell is provided. The second viral host range is unique to the target cell as to the other cells in the same animal or species, and supplies the target cell specificity for the delivery vector that binds the CVR polypeptide at its chimeric virus binding site.

The delivery vector is able to bind only the CVR polypeptide associated with the target cell, and not the target cell alone and/or other cells present with the target cell, such as, but not limited to, other cells in the same animal. The CVR polypeptide is permanently or transiently associated with the target cell, such as, but not limited to, by recombinant expression in the target cell, or by direct or indirect association with the surface of the target cell. The surface association may optionally include an intermediate that binds both the surface of the target cell and the CVR polypeptide.

A non-limiting example of an association of a CVR polypeptide with a target cell is the use of delivery vector having nucleic acid encoding an H13 human ecotropic viral receptor binding site which is modified at amino acids 242 and 238 of SEQ ID NO:8 with the corresponding amino acids of the murine ecotropic viral receptor. The resulting CVR polypeptide is a human protein capable of binding the env binding domain of a murine ecotropic viral vector, which vector cannot bind any other human cells. The delivery vector further comprises a Mab fragment which is specific for a tumor cell as the target cell.

The tumor cells and their progeny express the CVR polypeptide constitutively by incorporation of the CVR polypeptide encoding nucleic acid. Subsequent treatment of the target cells with a murine ecotropic viral vector having nucleic acid encoding thymidine kinase (TK), causes the tumor cells and their progeny to express TX and to be susceptible to selective killing by pharmaceutical administration of an antiviral agent that kills cells expressing thymidine kinase.

Of course, the present invention is not limited to the use or modification of human viral receptors with murine receptor sequences, but includes any modification of a viral receptor of a first viral host cell range with amino acids corresponding or similar to a sequence of receptor having a second viral host cell range. The modification confers binding capability for the second viral host cell range, e.g., a host cell range including a different species or cell type. And any type of delivery vector may be used which contains a second viral host cell range specific binding domain, wherein the target cell has a CVR polypeptide or second virus binding domain ligand associated or expressed on its surface.

The term "chimeric viral receptor polypeptide" or "CVR polypeptide" may thus refer to a polypeptide comprising at least 10 amino acids corresponding to a first viral receptor binding site or consensus sequence thereof, modified to confer, binding to the second virus, wherein the CVR polypeptide contains the first binding site modified to become a chimeric receptor binding site capable of binding a binding domain of the second virus, said chimeric binding site have 10–1000 amino acids, such as, but not limited to 10–700, 10–100, 10–50, 10–30, 20–30, 20–40, 40–60 amino acids or any range or value therein.

Alternatively, or additionally, CVR polypeptides of the present invention may be defined as amino acid sequences of at least 10 residues having at least 80% (such as 81–99%, or any value or range therein, such as 83–85, 87–90, 93–95, 97–98, or 99% or any range or value therein) homology with the corresponding amino acid sequence of a first viral receptor, for a virus having a first virus host cell range which has then been modified to confer binding capability to a second virus having a second virus host cell range different from the first virus. Preferably the first virus receptor binding site is derived from a human and the second virus receptor from a rodent, or vice versa. A non-limiting example of such a corresponding human viral receptor sequence is a binding site contained in SEQ ID NO:8, such as, but not limited to, corresponding to 10 to 629 amino acids of SEQ ID NO: 8, or any value or range therein.

Additionally or alternatively, a CVR polypeptide of the present invention may further comprise a hydrophobic amino acid sequence corresponding to at least one to twenty transmembrane domains of a first viral receptor protein which is at least 80% (such as 80–100%, or any range or value therein) homologous to the corresponding a first viral receptor. Such transmembrane domains may be analogous to those described, e.g., a human H13 sequence (SEQ ID NO:8) or a murine ERR (SEQ ID NO:4) having 14 potential transmembrane domains (see, e.g., Eisenberg et al., *J. Mol. Biol.* 179:125–142 (1984)), and which can be determined using hydrophobicity plots according to known method steps, e.g., as referenced therein or herein.

Such a non-limiting example of a CVR polypeptide of the present invention may be, e.g., a modified human H13 amino acid sequence (e.g., such as, but not limited to, SEQ ID NO: 8) of at least 10 amino acids which is modified to provide binding capability to a non-human specific virus, such is the non-limiting examples of E-MuLV, gp-70 or ERR receptor protein (SEQ ID NO: 4). Such modifications may preferably include substitution, at a receptor binding site of a human viral receptor sequence, by at least one non-human viral receptor amino acid, such as a murine ERR amino acid in the corresponding site in H13, to permit infection of a human or non-murine target cell having the CVR polypeptide, preferably a human cell, with a virus or retrovirus, such as edotropic murine leukemia virus (E-MuLV).

Thus, as a further non-limiting subexample, to confer E-MuLV infection susceptibility on a human or non-murine cell, it is preferred to substitute corresponding E-MuLV receptor amino acid residues of domain 3 of H13. Domain 3 comprises residues between positions 210 and 250 (SEQ ID NO:7). Preferred substitution is with 1–10 amino acid residues, or any number or range therein, from the corresponding domain of ERR, between amino acid residues 210 and 242 (SEQ ID NO:4), preferably amino acids 238, 239 and 242, with more preferably at least 242 being substituted. Substitution of between 1 and 4 residues is preferred. For example, residues and positions with differ in extracellular domain 3 of H13 and ERR are listed below in Table 1. In a more preferred embodiment, at least Pro242 of H13 (SEQ ID NO:8) is replaced by Tyr, and at least one of Gly240 and Val244 (SEQ ID NO:8) is replaced by Val and Glu, respectively, and as presented in FIG. 18. Additionally, at least one of H13 amino acid 239 may be preferably replaced by the corresponding ERR amino acid 233.

TABLE 1

Exemplary Substitutions in H13 Extracellular Domain 3 and Domain 4 for E-MuLV Binding Domain 3

| Original H13 Residue | Substituting ERR Residue |
|---|---|
| V 214 | I 214 |
| E 222 | K 222 |
| E 223 | N 223 |
| G 225 | S 225 |
| L 233 | N 227 |
| E 239 | N 232 |
| P 242 | Y 235 |
| V 244 | E 237 |

Non-limiting examples of CVR polypeptides according to the present invention may include Tyr242, Phe242 and/or Trp242 and at least one of Val240, Met240, Leu240, Ile240, Glu244, Gln244, Asp244, or Asn244; and Asn239, Asp239, Glu239 or Gln239 (SEQ ID NO:3), wherein at least Pro242 or H13 (SEQ ID NO:8) is replaced by Tyr, and at least one of Gly240 and Val244 (SEQ ID NO:8) is replaced by Val and Glu, respectively.

Another means for modifying virus binding specificity of H13 is by deletion of one or more of the "extra" amino acid residues in H13 that do not correspond to residues of ERR. Preferred deletions (in extracellular domain 4) are of between one and six residues from H13 positions 326 to 331 (SEQ ID NO:1), most preferably, deletion of all six of these residues.

In another non-limiting example of a CVR polypeptide of the present invention, an H13 CVR polypeptide may be provided which confers the binding ability of a human cell, to bind an env binding domain of a non-human virus, wherein 1 to 30 amino acids of H13 are substituted, deleted or modified by corresponding amino acids from ERR, in order to confer such binding ability. Preferably, such a CVR polypeptide may preferably comprises a peptide wherein at least Pro242 of the H13 polypeptide (SEQ ID NO:8) is replaced by Tyr, and at least one of the Gly240 and Val244 (SEQ ID NO:8) is replaced by Val and Glu, respectively, or fragments having amino acid sequences substantially corresponding to the amino acid sequence of H13, such that the resulting chimeric receptor is selectively bound by a murine ecotropic retrovirus, which cannot infect other human or non-murine cell or tissue types.

Alternatively, a homologous CVR polypeptide of an amphotropic first species viral receptor may be similarly modified to allow binding of a non-first species specific amphotropic virus, such as, but not limited to, a chimeric receptor cell or tissue. Preferably the first species is human or rodent.

Also included are soluble forms of H13 or a CVR polypeptide, as well as muteins and functional derivatives thereof, having similar bioactivity for all the uses described herein. Also intended are all active forms of chimeric receptors or viral receptor polypeptide derived from the chimeric receptor or H13 transcript, respectively, and all mutants with H13-like activity. Likewise, any antibody or antibody binding site for the viral envelope protein which is incorporated into the chimeric construct or the viral envelope respectively, can also be used according to the present invention.

Method steps for production of soluble forms of receptors which are normally transmembrane proteins are known in the art (see, for example, Smith, D. H. et al., *Science* 238:1704–1707 (1987); Fischer, R. A. et al., *Nature* 331:76–78 (1988); Hussey, R. E. et al., *Nature* 331:78–81 (1988); Deen, K. C. et al., *Nature* 331:82–84 (1988); Traunecker, A. et al., *Nature* 331:84–86 (1988); Gershoni, J. M. et al., *Proc. Natl. Acad. Sci. USA* 85:4087–4089 (1988), which references are hereby entirely incorporated by reference). Such methods are generally based on truncation of the nucleic acid encoding the receptor protein to exclude the transmembrane portion, leaving intact the extracellular domain (or domains) capable of interacting with specific ligands, such as, but not limited to, an intact retrovirus or a retroviral protein or glycoprotein.

For the purposes of the present invention, it is important that the soluble CVR polypeptide or viral receptor polypeptide, comprise elements of the binding site of the chimeric receptor or first viral receptor, alternatively, or a binding domain of an antibody to the env that permits binding to a virus. A CVR polypeptide or viral receptor polypeptide may have many amino acid residues, of which only one or two or more, such as 2–15, or any value or range therein, such as, but not limited to, 3–5, 6–9 or 10–15, which are critically involved in virus recognition and binding and which may be modified to provide a CVR polypeptide of the present invention. An antibody binding site may have a larger binding site, however, such as 4–50 amino acids, or any range or value therein.

The present invention thus overcomes one or more problems associated with the use of known viral vectors, such as, but not limited to, known amphotropic viral vectors, which are susceptible to non-specific infection with non-target cells, as well as reversion or mutation to replication competence, leading to viral infection in the animal, such as, but not limited to, human.

The term "chimeric receptor cell" or "chimeric receptor tissue" refers to a target cell or tissue having associated therewith a CVR polypeptide or tissue type having a second viral host cell range, a delivery vector of the present invention may specifically bind the chimeric cell or tissue, in vivo, in situ, or in vitro.

The term "associated" in the context of the present invention refers to any type of covalent or non-covalent binding or association such as, but not limited to, a covalent bind, hydrophobic/hydrophilic interaction, Van der Wahls forces, ion pairs, ligand-receptor interaction, epitope-antibody binding site interaction, enzyme-substrate interaction, liposome-hydrophobic interaction, nucleotide base pairing, membrane-hydrophobic interaction, and the like.

A "fragment" of the H13 protein or CVR polypeptide of this invention is any subset of the molecule, that is, a shorter peptide.

In a further embodiment, the invention provides muteins of a CVR polypeptide of the present invention. By "mutein" is meant a "variant," or "chemical derivative" of an H13 protein or a CVR polypeptide. A mutient retains at least a portion of the function of the H13 protein or CVR polypeptide which permits its utility in accordance with the present invention.

A "mutein" of the H13 CVR polypeptide refers to a molecule substantially similar to either the entire peptide or a fragment thereof. Muteins may be conveniently prepared by direct chemical synthesis or recombinant production, including mutagenesis, of the mutein, using methods well-known in the art. See, e.g., Sambrook, infra, Ausubel, infra, Colligan, infra.

At the genetic level, these muteins ordinarily are prepared by site-directed mutagenesis (as exemplified by Adelman et al., *DNA* 2:183 (1983) or Ausubel, supra, Sambrook, supra) or Colligan et al, eds., *Current Protocols in Immunology,* Greene Publishing Association and Wiley Intersciences N.Y., N.Y., (1992, 1993) of nucleotide in the nucleic acid encoding the peptide molecule, thereby producing nucleic acid encoding the mutant, and thereafter expressing the nucleic acid in recombinant cell culture. The muteins typically exhibit the same qualitative biological activity as a chimeric peptide.

Another group of muteins are those in which at least one amino acid residue in the protein molecule, and preferably, only one, has been removed and a different residue inserted in its place, where the replacement does not include the chimeric receptor binding site. For a detailed description of protein chemistry and structure, see Schulz, G. E. et al., *Principles of Protein Structure,* Springer-Verlag, New York, 1978, and Creighton, T. E., *Proteins: Structure and Molecular Properties,* W. H. Freeman & Co., San Francisco, 1983, which are hereby entirely incorporated by reference. The types of substitutions which may be made in the protein or peptide molecule of the present invention may be based on analysis of the frequencies of amino acid changes between a homologous protein of different species, such as, but not limited to, those presented in Table 1–2 of Schulz et al., supra and FIGS. 3–9 of Creighton supra.

Substantial changes in functional or immunological properties are made by selecting substitutions that are less conservative, such as, but not limited to, between, rather than within, the above five groups, which will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (a) substitution of gly and/or pro another amino acid or deletion of insertion of gly or pro; (b) substitution of a hydrophilic residue, e.g., ser or thr, for (or by) a hydrophobic residue, e.g., leu, ile, phe, val or ala; (c) substitution of a cys residue for (or by) any other residue; (d) substitution of a residue having an electropositive side chain, e.g., lys, arg or his, for (or by) a residue having an electronegative charge, e.g., Glu or asp; or (e) substitution of a residue having a bulky side chain, e.g., phe, for (or by) a residue not having such a side chain, e.g., gly.

Moste deletions and insertions, and substitutions according to the present invention are those which do not produce radical changes in the characteristics of the protein or peptide molecule. However, when it is difficult to predict the exact effect of the substitution, deletion, or insertion in advance of doing so, one skilled in the art will appreciate that the effect will be evaluated by routine screening assays, either immunoassays or bioassays. For example, a mutein typically is made by site-specific mutagenesis of the peptide molecule encoding nucleic acid, expression of the mutant nucleic acid in recombinant cell culture, and, optionally, purification from the cell culture, for example, by immunoaffinity chromatography using a specific antibody on a column (to absorb the mutein by binding to a least one epitope).

The activity of the cell lysate containing H13 or a CVR polypeptide, or of a purified preparation of a human viral receptor or chimeric receptor, can be screened in a suitable screening assay for the desired characteristic. For example, a change in the immunological character of the protein molecule, such as, but not limited to, binding to a given antibody, is measured by a competitive type immunoassay (as described herein). Biological activity is screened in an appropriate bioassay, such as, but not limited to, virus infectivity, as described herein.

Modifications of such peptide properties as redox or thermal stability, hydrophobicity, susceptibility to proteolytic degradation or the tendency to aggregate with carriers or into multimers are assayed by methods well known to the ordinarily skilled artisan.

Additionally, modified amino acids or chemical derivatives of amino acids of a CVR polypeptide according to the present invention, may be provided, which polypeptides contain additional chemical moieties or modified amino acids not normally a part of the protein. Covalent modifications of the peptide are thus included within the scope of the present invention. Such modifications may be introduced into a CVR polypeptide by reacted targeted amino acid residues of the polypeptide with an organic derivatizing agent that is capable of reacting with selected side chains or terminal residues.

Derivatization with bifunctional agents is useful for cross-linking the peptide to a water-insoluble support matrix or to other macromolecular carriers, according to known method steps. Alternatively, reactive water-insoluble matrices such as, but not limited to, cyanogen bromide-activated carbohydrates and the reactive substrates described in U.S. Pat. Nos. 3,969,287; 3,691,016; 4,195,128; 4,247,642; 4,229,537; and 4,330,440 (which are herein entirely incorporated by reference), may be employed for protein immobilization.

Other modifications of a CVR polypeptide of the present invention may include hydroxylation of the proline and lysine, phosphorylation of hydroxyl groups of seryl or threonyl residues, methylation of the alpha-amino groups of lysine, arginine, and histidine side chains (T. E. Creighton, *Proteins: Structure and Molecule Properties,* W. H. Freeman & Co., San Francisco, pp. 79–86 (1983)), acetylation of the N-terminal amine, and, in some instances, amidation of the C-terminal carboxyl groups, according to known method steps.

Such derivatized moieties may improve the solubility, absorption biological half life, and the like. Such moieties or modifications of a CVR polypeptide may alternatively eliminate or attenuate any undesirable side effect of the protein and the like. Moieties capable of mediating such effects are disclosed, for example, in *Remington's Pharmaceutical Sciences,* 16the ed., Mack Publishing Co., Easton, Pa. (1980).

Such chemical derivatives of a CVR polypeptide or viral receptor polypeptide also may provide attachment to solid supports, such as, but not limited to, for purification, generation of antibodies or cloning; or to provide altered physical properties, such as resistance to enzymatic degradation or increased binding affinity or modulation of a CVR polypeptide, which is desired for therapeutic compositions comprising a CVR polypeptide, antibodies thereto or fragments thereof. Such peptide derivatives are known in the art, as well as method steps for making such derivatives.

Methods for Making Chimeric Viral Receptor Polypeptides or Human Viral Receptor Polypeptides. Chemical synthesis, recombinant nucleic acid technology, purification from natural sources, or any other known method steps may be used to make a CVR polypeptide or human viral receptor polypeptide, according to the present invention.

Cloning and Expression of a Human Viral Receptor. Recombinant technology method steps (see, e.g., Ausubel, infra or Sambrook, infra) may be used to clone and/or express a nucleic acid encoding a viral receptor suitable for use in production of a CVR polypeptide or human viral polypeptide of the present invention from any species or cell type, without undue experimentation, based on the teaching and guidance presented herein. As a non-limiting example of such a procedure, one will initially screen (using methods routine in the art) a cDNA library of the species or cell type of interest, for example, a human T cell CDNA library, using a probe based on the sequence of a human viral receptor, such as, but not limited to, a 10–1000 base nucleotide probe, corresponding to a sequenced human amphotropic, polytropic, xenotropic or ecotropic viral receptor, such as, but not limited to, H13 (SEQ ID NO:7). Next, one can clone and sequence the hybridizing nucleic acid to obtain the sequence of the "new" retroviral receptor. By visual inspection or with the aid of a computer program (as described herein) it is possible to identify the regions in which the sequence of the new retroviral receptor protein differs from a mammalian or human viral receptor, e.g., ERR or H13. In particular, one may determine regions corresponding to extracellular domain regions 3 or 4 of a human viral receptor, such as, but not limited to, human receptor H13 (SEQ ID NOS: 7 and 8) or analogous domains.

Based on the sequence differences observed, it is possible, using the techniques provided herein, to create a sequence having one or more amino acid substitutions, deletions or additions such that the resulting CVR polypeptide is created as a chimeric of the new receptor and a known receptor. The CVR polypeptide can then be recombinantly expressed in a cell of choice, or chemically synthesized, and its binding site specificity and/or viral host cell range routinely tested using known method steps or virus infectivity assays and/or virus binding assays.

It is also within the scope of the present invention to express more than one intact human viral or CVR polypeptide on the surface of the same cell.

Oligonucleotides representing a portion of the H13 sequence (SEQ ID NO:2) are useful for screening for the presence of homologous viral receptor genes and for the cloning of such genes. Techniques for synthesizing such oligonucleotides are disclosed by, for example, Wu, R., et al., *Prog. Nucl. Acid. Res. Molec. Biol.* 21:101–141 (1978)), Ausubel et al., infra; Sambrook, infra.

Additionally, DNA synthesis may be achieved through the use of automated synthesizers. Techniques of DNA hybridization are disclosed by Sambrook et al. supra, and by Haymes, B. D., et al., (In: *DNA Hybridization, A Practical Approach,* IRL Press, Washington, D.C. (1985), which references are herein incorporated by reference. Techniques such as, or similar to, those described above have successfully enabled the cloning of genes for human aldehyde dehydrogenase (Hsu, L. C., et al., *Proc. Natl. Acad. Sci. USA* 82:3771–3775 (1985)), fibronectin (Suzuki, S., et al., *Eur. Mol. Biol. Organ. J.* 4:2519–2524 (1985)), the human estrogen, receptor gene (Walter, P., et al., *Proc. Natl. Acad. Sci. USA* 82:7889–7893 (1985)), tissue-type plasminogen activator (Pennica, D., et al., *Nature* 301;214–221 (1983)) and human placental alkaline phosphatase complementary DNA (Kam, W., et al., *Proc. Natl. Acad. Sci. USA* 82:8715–8719 (1985)).

In an alternative way of cloning a human viral receptor gene, a library of expression vectors can be prepared by cloning generic DNA or, more preferably, preparing CDNA, from a cell capable of expressing a human receptor or CVR polypeptide, into an expression vector. The library is then screened for members capable of expressing a protein which binds to anti-human mammalian viral receptor, antibody, and which has a nucleotide sequence that is capable of encoding polypeptides that have the homologous amino acid sequences as a human viral receptor, such as H13 (SEQ ID NO:8).

A nucleic acid sequence encoding a putative human viral receptor or fragment thereof, may then be recombined with vector DNA in accordance with conventional techniques, including blunt-ended or staggered-ended termini for ligation, restriction enzyme digestion to provide appropriate termini filling in of cohesive ends as appropriate, alkaline phosphatase treatment to avoid undesirable joining, and ligation with appropriate ligase and expressed in an appropriate host cell. Techniques for such manipulations are disclosed, e.g., by Sambrook, J. et al., supra, Colligan, infra, and are well known in the art.

Cloning Amphotropic Viral Receptors. Virtually all gene therapy protocols conducted to date in humans have used amphotropic vectors derived from mice. Amphotropic retroviruses are capable of infecting cells of many mammalian species, including mouse, rat, rabbit, guinea pig, cat, dog, and human cells, but importantly, not hamster (Hartley and Rowe *J. Virol* 19:19–25 (1976); Rasheed et al. *J. Virol* 19:13–18 (1976).) Our approach to clone an amphotropic virus receptor gene is based on the method used to clone the receptors for Gibbon ape leukemia virus and mouse ecotropic virus (E-MLV). The approach relies on the fact that human cells can be infected by A-MLV but hamster cells cannot. The inability to infect hamster cells is discovered to result from their lack of a suitable receptor. DNA containing the human gene can thus be transfected into hamster cells, rendering them infectable by a A-MLV carrying the neomycin resistant gene (neo$^R$), followed by isolation of the cells expressing the A-MLV receptor by selection in G418 containing media. The receptor gene then become accessible to cloning after two to three cycles of transfection and selection.

For example, the chinese hamster ovary cell line, CHO-K1, which is initially resistant to amphotropic murine leukemia retrovirus, may be transfected with a human CDNA library. The transfected cells are then infected with the amphotropic retroviral vector bearing neomycin resistance gene. Infected cells are selected with neomycin analog, G418, and cloned. The existence of transfected genes in the genomic DNA of cloned cells can then be confirmed by Southern blotting and hybridization method and the genes specifically amplified by PCR method. Having followed the above procedure, the amplified genes were cloned and their possible functioning as the receptor for amphotropic retrovirus was investigated, as described herein.

Only two kinds of repetitive sequences are available so far for detecting human genomic DNA, which weakly cross-hybridize with hamster's genomic DNA. This problem was solved in the present invention by transfection with human CDNA library and by the usage of CMV promoter sequence as the probe in Southern blotting and hybridization method, in which the existence of rare restriction enzyme recognition site in the CMV vector's sequence made it possible to reduce background and selectively detect the presence of human sequences.

Furthermore, the use of such a well characterized vector made it possible to amplify the transferred human CDNAS specifically and also made it easy to confirm that the PCR products were derived from the transferred human CDNA library. The isolated clones were sequenced according to known method steps (se Ausubel, infra, and Sambrook, infra). The discovered amphotrophic viral receptor clones were then put into hamster cells and shown to render these cells perceptible to infection by amphotropic virus', thus confirming that a clone obtained was an amphotropic virus receptor. Accordingly, the teachings provided herein routinely provide cloning and expression of human or other mammalian amphotropic receptors.

Expression of Human Viral Receptors, Mammalian Receptors and/or CVR Polypeptides Such viral receptors of the present invention can be recombinantly expressed in eukaryotic or prokaryotic hosts, without undue experimentation, based on the teaching and guidance presented here. See. e.g., Ausubel, infra; Sambrook, infra.

Eukaryotic hosts may include yeast, insects, fungi, and mammalian cells either in vivo, or in tissue culture. Mammalian cells provide post-translational modifications to protein molecules including correct folding or glycosylation at correct sites. Mammalian cells which may be useful as hosts include cells of fibroblast origin such as, but not limited to, NIH 3T3, VERO or CHO, or cells of lymphoid origin, such as, but not limited to, the hybridoma SP2/O-Ag14 or the murine myeloma P3-X63AgB, hamster cells lines (e.g., CHO-K1 and progenitors, e.g., CHO-DUXB11, and their derivatives. Preferred mammalian cells are cells which are intended to replace the function of the genetically deficient cells in vivo. Bone marrow stem cells are preferred for gene therapy of disorders of the hemopoietic or immune system.

For a mammalian cell host, many possible vector systems are available for the expression of a human viral receptor or CVR polypeptide. A wide variety of transcriptional and translational regulatory sequences may be employed, depending upon the nature of the host. The transcriptional and translational regulatory signals may be derived from viral sources, such as, but not limited to, adenovirus, bovine papilloma virus, Simian virus, or the like, where the regulatory signals are associated with a particular gene which has a high level of expression. Alternatively, promoters from mammalian expression products, such as, but not limited to, actin, collagen, myosin, protein production. When live insects are to be used, silk moth caterpillars and baculovirus vectors are presently preferred hosts for large scale viral receptor polypeptide or CVR polypeptide production according to the invention. See, e.g., Ausubel, infra, Sambrook, infra.

If so desired, the expressed CVR polypeptide or human receptor polypeptide may be isolated and purified in accordance with conventional method steps, such as extraction, precipitation, chromatography, affinity chromatography, electrophoresis, or the like. For example, the cells may be collected by centrifugation, or with suitable buffers, lysed, and the protein isolated by column chromatography, for example, on DEAE-celluose, phosphocellulose, polyribocytidylic acid-agarose, hydroxyapatite or by electrophoresis or immuno-precipitation. Alternatively, viral receptors or CVR polypeptides may be isolated by the use of specific antibodies, such as, but not limited to, an anti-CVR polypeptide or anti-human viral receptor antibody that still reacts with the protein containing ERR-derived amino acid substitutions. Such antibodies may be obtained by known method steps.

Furthermore, manipulation of the genetic constructs of the present invention allow the grafting of a particular virus-binding domain onto the transmembrane and intracytoplasmic portions of a CVR polypeptide or human viral receptor polypeptide, or grafting the retrovirus receptor binding domain of a CVR polypeptide or human viral receptor polypeptide onto the transmembrane and intracytoplasmic portions of another molecule, resulting in yet another type of chimeric molecule.

Providing Chimeric Receptor Cells or Tissues

The present invention also provides methods for rendering a human or other eukaryotic cell or tissue infectable by a non-human specific virus, which cell or tissue is susceptible to binding by an env binding domain of the non-human virus. Such a cell is preferably a chimeric receptor cell associated with a CVR polypeptide.

In another embodiment, the present invention includes a modified chimeric receptor cell or tissue produced by a herein-described method, wherein the eukaryotic cell or tissue is selected from, but not limited to mammalian, insect, bird or yeast origin. It is preferred that the mammalian cell or tissue is of human, primate, hamster, rabbit, rodent, cow, pig, sheep, horse, goat, dog or cat origin, but any other mammalian cell may be used.

The method may optionally first comprise transforming, in vitro, in vivo or in situ, a eukaryotic cell or tissue with an expressible nucleic acid encoding a CVR polypeptide to produce a recombinant chimeric receptor chimeric or tissue which is capable of expressing a CVR polypeptide capable of binding an extracellular viral env binding domain of a virus having a host cell range that does not include the cell without the CVR polypeptide.

Standard reference works setting forth the general principles of recombinant DNA technology include Watson, J. D. et al., *Molecular Biology of the Gene,* Volumes I and II, The Benjamin/Cummings Publishing Company, Inc., publisher, Menlo Park, Calif. (1987); Darnell, J. E. et al., *Molecular Cell Biology,* Scientific American Books, Inc., publisher, New York, N.Y. (1986); Lewin, B. M., *Genes II,* John Wiley & Sons, publishers, New York, N.Y. (1985); Old, R. W., et al., *Principles of Gene Manipulations: An Introduction to Genetic Engineering,* 2d edition, University of California Press, publisher, Berkley, Calif. (1981); Sambrook, J. et al., *Molecular Cloning: A Laboratory Manual,* Cold Spring Harbor Laboratory, Second Edition, Cold Spring Harbor, N.Y. (1989); and Ausubel et al *Current Protocols in Molecular Biology,* Wiley Interscience, N.Y., (1987, 1993). These references are herein entirely incorporated by reference.

It is preferred in such a method that the in vivo transforming is carried out by at least one selected from: injection of the mutant nucleic acid into the tissue or cell; retroviral infection using a recombinant retrovirus comprising the mutant nucleic acid under control of at least one tissue specific regulatory sequence specific for the tissue or cell; liposome delivery of the mutant nucleic acid to the tissue or cell; antibody delivery of the mutant nucleic acid to the tissue or cell; or contacting a cell or tissue specific antibody conjugated to the mutant nucleic acid to the tissue or cell, according to known method steps.

It is also preferred in such a method that the in situ or in vitro transforming be carried out by one selected from: injection of the mutant nucleic acid into the tissue or cell; retroviral infection using a recombinant retrovirus comprising the mutant nucleic acid in expressible form; liposome delivery of the mutant nucleic acid, antibody delivery of the mutant nucleic acid; transection of the tissue or cell with the mutant nucleic acid; or contacting the cell or tissue specific antibody conjugated to the mutant nucleic acid to the tissue or cell, according to known methods steps. It is additionally preferred that the virus is a murine retrovirus.

Delivery Vectors. A delivery vector of the present invention may be, but is not limited to, a viral vector, a liposome, or a conjugate of the env binding domain associated with diagnostic or therapeutic agent.

The delivery vector may comprise any diagnostic or therapeutic agent which has a therapeutic or diagnostic effect on the target cell. The target cell specificity of the delivery vector is thus provided by use of a CVR polypeptide of the present invention and/or by the use of a target cell receptor ligand in the delivery vector.

The delivery vector may further comprise a complex fusion protein, a liposome, an antibody or fragment, a glycoprotein, a peptide and the like, which is capable of specific binding to a target cell via target cell associated CVR polypeptide, a target cell specific receptor, or an CVR polypeptide ligand or the delivery vector.

Alternatively or additionally, the delivery vector may comprise a viral vector in which the env domain or encoding nucleic acid has been replaced by a domain capable of binding to the target cell or as a chimeric cell, such as, but not limited to, a target cell receptor ligand.

The delivery vector may also be a recombinant viral vector comprising at least one binding domain selected from the group consisting of env binding domain, an antibody or fragment, a chimeric binding site antibody or fragment, a second env binding domain, a target cell or specific ligand, a receptor which binds a target cell ligand, an anti-idiotypic antibody, a liposome or other component which is specific for the target cell. A CVR polypeptide may be already associated with the target cell, or the delivery vector may bind the target cell via a ligand to a target cell receptor or vice versa.

According to the present invention, it is possible to provide target cell specific delivery vectors as viral vectors by modifying the receptor attachment site of a virus, as the binding domain or env binding domain, so that the binding domain will not bind to its natural receptor, and/or bind to a different receptor, based on knowledge of receptor choice determinants in envelope glycoproteins or viruses (such as, but not limited to, murine leukemia viruses). See, e.g., Battini et al *J. Virology* 66(3):1468–1475 (1992). Alternatively or additionally, the delivery vector binding domain can be replaced by genetic engineering, analogous to replacing the env with an EPO receptor, as by Longmore et al., *Cell,* 67:1089–1102 (1991). In one non-limiting example, a CVR polypeptide is specifically delivered to a target cell having viral receptors of a first viral host cell range, by association with a target cell specific vector, such as an antibody, liposome or target cell specific receptor ligand, such that the CVR polypeptide is associated with the target cell for a sufficient time to allow treatment or diagnosis using a delivery vector comprising a therapeutic agent or diagnostic agent with or in associated with the receptor binding or env domain of a second virus having a different second viral host cell range, which delivery vector is capable of binding the CVR polypeptide associated with the target cell. Thus, the therapeutic or diagnostic agent, such as a therapeutic or diagnostic nucleic acid, protein, drug, compound composition and the like, is delivered preferentially to the target cell, e.g., where the nucleic acid is incorporated into the chromosome of the target cell, to the exclusion of the non-target cells.

The present invention is thus intended to provide delivery vectors, containing one or more therapeutic and/or diagnostic agents, including vectors suitable for gene therapy, having an improved measure of safety compared to related art approaches.

Diagnostic and/or Therapeutic Agents

The diagnostic or therapeutic agent may be, but is not limited to, at least one selected from a nucleic acid, a compound, a protein, an element, a lipid, an antibody, a saccharide, an isotope, a carbohydrate, an imaging agent, a lipoprotein, a glycoprotein, an enzyme, a detectable probe, and antibody or fragment thereof, or any combination thereof, which may be detectably labeled as for labeling antibodies, as described herein. Such labels include, but are not limited to, enzymatic labels, radioisotope or radioactive compounds or elements, fluorescent compounds or metals, chemiluminescent compounds and bioluminescent compounds. Alternatively, any other known diagnostic or therapeutic agent can be used in a method of the present invention.

A therapeutic agent used in the present invention may have a therapeutic effect on the target cell as a chimeric receptor cell, the effect selected from, but not limited to: correcting a defective gene or protein, a drug action, a toxic effect, a growth stimulating effect, a growth inhibiting effect, a metabolic effect, a catabolic affect, an anabolic effect, an antiviral effect, an antibacterial effect, a hormonal effect, a neurohumoral effect, a cell differentiation stimulatory effect, a cell differentiation inhibitory effect, a neuromodulatory effect, an antineoplastic effect, an anti-tumor effect, an insulin stimulating or inhibiting effect, a bone marrow stimulating effect, a pluripotent stem cell stimulating effect, an immune system stimulating effect, and any other known therapeutic effects that may be provided by a therapeutic agent delivered to a chimeric receptor cell via a delivery vector according to the present invention.

A therapeutic nucleic acid as a therapeutic agent may have, but is not limited to, at least one of the following therapeutic effects on a chimeric receptor cell: inhibiting transcription of a DNA sequence; inhibiting translation of an RNA sequence; inhibiting reverse transcription of an RNA or DNA sequence; inhibiting a post-translational modification of a protein; inducing transcription of a DNA sequence; inducing translation of an RNA sequence; inducing reverse transcription of an RNA or DNA sequence; inducing a post-translational modification of a protein; transcription of the nucleic acid as an RNA; translation of the nucleic acid as a protein or enzyme; and incorporating the nucleic acid into a chromosome of a chimeric receptor cell for constitutive or transient expression of the therapeutic nucleic acid.

Therapeutic effects of therapeutic nucleic acids may include, but are not limited to: turning off a defective gene or processing the expression thereof, such as antisense RNA or DNA; inhibiting viral replication or synthesis; gene therapy as expressing a heterologous nucleic acid encoding a therapeutic protein or correcting a defective protein; modifying a defective or underexpression of an RNA such as an hnRNA, an mRNA, a tRNA, or an rRNA; encoding a toxin in pathological cells; encoding a drug or prodrug, or an enzyme that generates a compound as a drug or prodrug in pathological or normal cells expressing the chimeric receptor; encoding a thymidine kinase varicella-zoster virus thymidine kinase (VZV TK) (see, e.g., Huber et al *Proc Nat'l Acad. Sci. USA* 88:8039–8042 (1992), the entire contents, including the cited references, are entirely incorporated by reference) in pathogenic cells, such as neoplastic cells to directly or indirectly kill such pathogenic cells; and any other known therapeutic effects. Mutant nucleic acids such as those described above may thus be used in gene therapy.

A therapeutic nucleic acid of the present invention which encodes, or provides the therapeutic effect any known toxin, prodrug or drug gene for delivery to pathogenic cells may also include genes under the control of a tissue specific transcriptional regulatory sequence (TRSs) specific for pathogenic cells, such as neoplastic cells, including α-fetoprotein TRS or liver-associated albumin TRS (see, e.g., Dynan and Tjian *Nature* (London) 316:774–778 (1985)). Such TRSs would further limit the expression of the cell killing toxin, drug or prodrug in the target cell as a cancer cell expressing a CVR polypeptide of the present invention.

A further example of a therapeutic nucleic acid of the present invention which is delivered and expressed in a chimeric receptor cell, is a therapeutic nucleic acid encoding a thymidine kinase which selectively kills eukaryotic dividing cells, such as brain tumor cells which brain cells surrounding the tumor cells are not dividing. Accordingly, a brain tumor could be injected, transfected or viral vector transformed in vivo with a CVR polypeptide encoding nucleic acid of the present invention, followed by therapeutic treatment of the chimeric receptor brain tumor cells with a recombinant ecotropic retrovirus encoding a thymidine kinase, such that the brain tumor cells would be selectively killed by expression of the thymidine kinase. See, e.g., F. Anderson et al, *Science* June, 1992, Culver, *Science,* 256:1550–1152, 1992.

Pharmaceutical Compositions. Pharmaceutical compositions comprising proteins, peptides, liposomes, antibodies or other diagnostic or therapeutic agent of the present invention, such as comprising at least one CVR polypeptide, or delivery vector binding domain specific for a target cell, include all compositions wherein at least one diagnostic/therapeutic agent is contained in an amount effective to achieve its intended purpose. In addition, pharmaceutical compositions containing at least one therapeutic agent may contain suitable pharmaceutically acceptable carriers comprising excipients and auxiliaries which facilitate processing of the active compounds into preparations which can be used pharmaceutically.

Pharmaceutical compositions include suitable solutions for administration by injection or orally, and contain from about 0.001 to 0.99 percent, preferably from about 20 to 75 percent of active component (i.e., the therapeutic together with the excipient. Pharmaceutical compositions for oral administration include tablets and capsules. Compositions which can be administered rectally include suppositories.

Therapeutic carriers for the active ingredient may be either in sprayable or nonsprayable form. Non-sprayable forms can be semi-solid or solid forms comprising a carrier conducive to topical application and having a dynamic viscosity preferably greater than that of water. Suitable formulations include, but are not limited to, solutions, suspensions, emulsions, creams, ointments, powders, liniments, salves, and the like. If desired, these may be sterilized and/or mixed with auxiliary agents, e.g., preservatives, stabilizers, wetting agents, buffers, or salts for influencing osmotic pressure and the like. Preferred vehicles for non-sprayable topical preparations may include ointment bases, e.g., polyethylene glycol-1000 (PEG-1000); conventional creams such as HEB cream; gels; as well as petroleum jelly and the like.

Also suitable for systemic or topical application, in particular to the mucus membranes and lungs, are sprayable aerosol preparations wherein the active ingredient, preferably in combination with a solid or liquid inert carrier material. The aerosol preparations can contain solvents, buffers, surfactants, perfumes, and/or antioxidants in addition to the proteins or peptides of the present invention. For aerosol administration, the therapeutic agents in accordance with the present invention may be packaged in a squeeze bottle, or in a pressurized container with an appropriate system of valves and actuators. Preferably, metered valves are used with the valve chamber being recharged between actuation or dose, all as is known in the art.

Therapeutic/diagnostic administration of a diagnostic/therapeutic agent of the present invention may be administered by any means that achieve its intended purpose, for example, for gene therapy, for diagnostic labeling of tissues, or to treat local infection or to treat systemic infection in a subject who has, or is susceptible to, such infection.

For example, administration may be by various parenteral routes such as subcutaneous, intravenous, intradermal, intramuscular, intraperitoneal, intranasal, intracranial, transdermal, or buccal routes. Alternatively, or concurrently, administration may be by the oral route. Parenteral administration can be by bolus injection or by gradual perfusion over time.

An additional mode of using of a diagnostic/therapeutic agent of the present invention is by topical application. A diagnostic/therapeutic agent of the present invention may be incorporated into topically applied vehicles such as salves or ointments.

For topical applications, it is preferred to administer an effective amount of a diagnostic/therapeutic agent according to the present invention to target area, e.g., skin surfaces, mucous membranes, etc. This amount will generally range from about 0.0001 mg to about 1 g per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base, the latter being preferably PEG-1000.

A typical regimen for treatment or prophylaxis comprise administration of an effective amount over a period of one or several days, up to and including between one week and about six months.

It is understood that the dosage of a diagnostic/therapeutic agent of the present invention administered in vivo or in vitro will be dependent upon the age, sex, health, and weight of the recipient, kind of concurrent treatment, if any, frequency of treatment, and the nature of the diagnostic/therapeutic effect desired. The ranges of effective doses provided herein are not intended to be limiting and represent preferred dose ranges. However, the most preferred dosage will be tailored to the individual subject, as is understood and determinable by one skilled in the relevant arts.

The total dose required for each treatment may be administered by multiple doses or in a single dose. The diagnostic/therapeutic agent may be administered alone or in conjunction with other diagnostics and/or therapeutics directed to the pathology, or directed or other symptoms of the pathology.

Effective amounts of a diagnostic/therapeutic agent of the present invention are from about 0.001 µg to about 100 mg/kg body weight, and preferably from about 1 µg to about 50 mg/kg body weight.

Diagnostic Assays. The present invention also provides methods for evaluating the presence and the level of normal or pathologic viral receptors or CVR polypeptides or encoding nucleic acid in a subject. Absence, or more typically, low expression of a viral receptor or presence of a mutant viral receptor in an individual may serve as an important predictor of resistance to viral infection and thus to a viral related pathology, e.g., cancer, AIDS, and the like. Alternatively, over-expression of a viral receptor, may serve as an important predictor of enhanced susceptibility to viral infection.

In addition, viral receptor MRNA expression may be increased in virally-induced tumor or cancer cell lines, indicating that the level of MRNA or receptor protein expression may serve as a useful indicator of a viral infection not otherwise detectable. Therefore, by providing a means to measure the quantity of viral receptor MRNA (as described herein) or protein (using an immunoassay as described herein), the present invention provides a means for detecting a virally-infected or virally-transformed cell in a subject, such as, but not limited to, by a retrovirus.

Oligonucleotide probes encoding various portions of a CVR polypeptide or human viral receptor polypeptide encoding nucleic acid sequence can be used in this invention to test cells from a subject for the presence a CVR polypeptide, viral receptor polypeptide, or encoding DNA or MRNA. A preferred probe would be one directed to the nucleic acid sequence encoding at least 12 and preferably at least 18 nucleotides of a CVR polypeptide or viral receptor polypeptide sequence. Qualitative or quantitative assays can be performed using such probes. For example, Northern analysis (as described herein or known in the art) is used to measure expression of a CVR polypeptide or viral receptor MRNA in a cell or tissue preparation.

Such methods can be used even with very small amounts of nucleic acid obtained from an individual, e.g., by use of selective amplification techniques. Recombinant nucleic acid methodologies capable of amplifying purified nucleic acid fragments have long been recognized. Typically, such methodologies involve the introduction of the nucleic acid fragment into a DNA or RNA vector, the clonal amplification of the vector, and the recovery of the amplified nucleic acid fragment.

Methods of amplification of RNA or DNA are well known in the art and can be used according to the present invention without undue experimentation, based on the teaching and guidance presented herein. Known methods of DNA or RNA amplification include, but are not limited to polymerase chain reaction (PCR) and related amplification processes (see, e.g., U.S. Pat. Nos. 4,683,195, 4,683,202, 4,800,159, 4,965,188, to Mullis et al.; 4,795,699 and 4,921,794 to Tabor et al; 5,142,033 to Innis; 5,122,464 to Wilson et al.; 5091,310 to Innis; 5,066,584 to Gyllensten et al; 4,889,818 to Gelfand et al; 4,994,370 To Silver et al; 4,766,067 to Biswas; 4,656,134 to Ringold) and RNA mediated amplification which uses anti-sense RNA to the target sequence as a template for double stranded DNA synthesis (U.S. Pat. No. 5,130,238 to Malek et al, with the tradename NASBA), the entire contents of which patents are herein entirely incorporated by reference.

Briefly, as a non-limiting example, PCR provides a method for selectively increasing the concentration of a particular sequence even when that sequence has not been previously purified and is present only in a single copy in a sample. The method can be used to amplify either single- or double-stranded DNA or RNA. The method involves use of two oligonucleotide primers to serve as primers containing the corresponding 5' ends of the complimentary strands of double stranded DNA corresponding to the target nucleic acid sequence to be amplified.

The reaction provides for the binding of the primers to either the target encoding strand or the corresponding complimentary strand, from which the bound primers provide a double stranded template to synthesize a copy of the target and complimentary strands. Once the target and complimentary strands are synthesized as the corresponding double stranded DNA (dsDNA), the reaction mixture is then heated to denature the double stranded DNA, from for which new primers can bind and provide new templates for a further round of double stranded synthesis of the target and complimentary strands. The above cycle is repeated many times as a denaturing reaction, a primer binding reaction and dsDNA reactions, to provide thousands, up to a million copies or more, of the target sequence. In the case of RNA amplification, the resulting amplified dsDNA is then used as a template for RNA synthesis from the coding strand of the amplified target dsDNA.

Therapeutic and Diagnostic Methods Involving Chimeric receptor and/or viral receptor polypeptides and/or Chimeric Cells or Tissue Therapeutic methods are also provided according to the present invention wherein tissue or cells having at least one expressible CVR polypeptide encoding nucleic acid are subject to infection by a recombinant non-human specific retroviral vector that recognizes only cells expressing, or bound on their surface, a CVR polypeptide, and the retroviral vector cannot infect other human cells, due to the non-human specificity of the vector and the relative lack of ability to revert, mutate or recombine to provide replication competence.

According to the present invention, a CVR polypeptide can be selectively associated with a target cell or expressed on the target cell by allowing infection by a recombinant retrovirus having nucleic acid encoding the CVR polypeptide. This temporary and/or permanent association allows target cells, such as pathologic cells having a particular receptor, to selectively expose and/or express a CVR polypeptide (as well as progeny of such pathogenic cells in the case of constitutively expressed CVR polypeptide) making possible specific delivery of therapeutic agents to such target cells and/or their progeny, according to the present invention.

Thus, according to the present invention, a procedure for marking and/or treating specific target cells (and, optionally, their progeny, with recombinant, chromosomal expression of a CVR polypeptide) is provided, by temporarily or permanently associating a CVR polypeptide with a target cell specific cell surface molecule, such as, but not limited to, cell surface receptor, and then administering a recombinant retrovirus which binds the CVR polypeptide and infects the target cell. The infecting virus vector may carry any of a variety of therapeutic nucleic acids or therapeutic genes conferring one or more functions, optionally comprising nucleic acid encoding for a CVR polypeptide.

As another non-limiting example, the delivery vector can carry into the cell a CVR polypeptide encoding nucleic acid. Once the target cell is infected, the target cell has incorporated into its chromosomes or genomic DNA, the CVR polypeptide encoding DNA, such that subsequently the target cell and its progeny will express the CVR polypeptide on the target cell surface. By marking such target cells and their progeny with a CVR polypeptide according to the present invention, an animal subject suffering from the pathology can be treated using gene therapy, wherein the gene therapy vector specifically binds the CVR polypeptide and delivers a therapeutic or diagnostic agent to the target cell and its progeny. Using such methods of the present invention, specific pathologies may be treated with or without substantially reduced risk of non-specific retroviral vector infection and gene insertion in to the chromosome.

According to the present invention, a CVR polypeptide encoding nucleic acid may be combined with a coding sequence for a polypeptide that specifically binds a receptor specific for a particular type of target cell. The expression of such a nucleic acid in a suitable host provides a fusion protein in recoverable amounts, which after purification can be used for therapeutic administration. The pharmaceutically acceptable fusion protein may then be administered to a subject having a pathology such that the fusion protein will specifically bind target cells and will act as an viral receptor for a second viral binding domain specific for only the target cells. The subsequent administration of a delivery vector having a second viral binding domain, which has nucleic acid encoding any of a large variety of genes, may confer one or more functions on the infected cell and provide a therapeutic/diagnostic effect on the target.

As a further non-limiting example, human tumors may be treated using a CVR polypeptide as a fusion protein further containing an antibody fragment of an antibody specific for a human tumor cell surface receptor. Such a fusion protein in pharmaceutically acceptable form may be administered to an animal model or human subject to mark tumor cells for infection by a second viral binding domain contained in a delivery vector, further comprising a therapeutic/diagnostic agent made specific for the target cell by the CVR polypeptide. The fusion protein binds the tumor cells as the target cells and the CVR polypeptide is expressed in the target cell and its progeny. Once the tumor cells constitutively express a CVR polypeptide, then gene therapy can be safely used to deliver a therapeutic/diagnostic agent to the tumor cells as the target cells, substantially without infection into non-target cells. However, it is not necessary that the cell express the CVR polypeptide, receptor. As determinable by one skilled in the art without undue experimentation. It is also possible to administer the CVR polypeptide-tumor binding protein fusion protein and delivery vector simultaneously. This might be desirable for several reasons. A nonlimiting example would be the need to overcome rapid shedding of the chimeric receptor from the cell surface or a short plasma half-life of the fusion protein.

As a non-limiting sub-example, B3 antibody fragments specific for human tumor cells may be used to provide a fusion protein and gene therapy, wherein a specific pathologic cell specific antibody or binding protein is first expressed as fusion protein with a CVR polypeptide, shown to: (a) bind the pathologic cells and allow infection by a non-human specific virus having nucleic acid encoding a CVR polypeptide in vitro and in vivo, such that the DVR polypeptide is expressed on the surface of the virus infected pathologic cell, followed by (b) in vitro and in vivo killing of the virus infected target cell by at least one therapeutic agent associated with an env binding domain as the delivery vector that binds the CVR polypeptide. Animal model systems may be preferably used before clinical treatment of humans, according to known methods steps.

Selective introduction of a CVR polypeptide encoding nucleic acid into animal or human cells or tissues, which are to be infected by the recombinant non-target cell specific virus, such as, but not limited to, an ecotropic or amphotropic virus, may be accomplished according to known method steps. Non-limiting examples include in vitro transfection of human cells or tissues, such as bone marrow cells (as stem cells or stromal cells), white blood cells, and differentiated or undifferentiated granulocytes, monocytes, macrophages, lymphocytes, erythrocytes, megakaryocytes, cells of the central nervous system, and tissue cells, such as, but not limited to, nerve tissue, liver cells, kidney cells, muscle cells, heart cells or myocardial cells, atrial or venus cells or tissue, eye cells, connective tissue or cells, lung tissue or cells, spleen cells or tissue, endocrine tissue or cells, CSF, or cells of the central nervous system, with nucleic acid encoding a CVR polypeptide, followed by reintroduction into the human subject; or by direct injection of a nucleic acid encoding the CVR polypeptides into the tissue including the target cells in vivo or in situ, such as, but not limited to, muscle, heart, liver, kidney, brain, nerve, spleen, pancreas, testes, ovary, pituitary, hypothalamus, gall bladder, eyes, lung, bone marrow, etc.

Thus, according to one aspect of the present invention, a method is provided for transferring at least one therapeutic agent/diagnostic agent to a chimeric receptor cell or tissue. The method comprises providing a chimeric cell or tissue according to the present invention and contacting the chimeric receptor cell or tissue, in vitro, in vivo or in situ, with a delivery vector comprising a binding domain of a second virus having a host cell range not including the target cell, and at least one therapeutic or diagnostic agent, such that the delivery vector binds the chimeric cell and the therapeutic or diagnostic agent has a therapeutic or diagnostic effect specific to the chimeric receptor cell.

In a method of the present invention, it is also preferred that the delivery vector is a recombinant, non-human specific virus, such that binding of the non-human specific virus to the chimeric receptor cell or tissue results in infection of the modified receptor cell and the therapeutic effect of the therapeutic nucleic acid in the chimeric receptor cell. In another preferred embodiment, the delivery vector includes a complex fusion protein, or nucleic acid encoding therefor, comprising a non-human specific env binding domain bound by a linker to a therapeutic or diagnostic agent, such that the binding or contacting results in a desired therapeutic or diagnostic effect. In still another preferred embodiment, the delivery vector may further comprise a liposome, the liposome containing the env binding domain and the therapeutic agent, such that the env binding domain is capable of binding the chimeric receptor binding site of a chimeric receptor cell. In yet another preferred embodiment, the delivery vector is the virus itself, in which the env domain has been replaced by a domain capable of binding to existing reception, antibodies, antigens, etc. on the surface of cells or tissues.

In another preferred embodiment, the contacting of the delivery vector to the chimeric receptor cell or tissue may result in the chimeric receptor cell or tissue expressing a therapeutically effective amount of the expression product of a therapeutic nucleic acid.

In another preferred embodiment, the therapeutic nucleic acid encodes a toxin which acts to selectively kill the chimeric receptor containing cell or tissue. The pathologic cell may be a cancer cell. In another embodiment, the therapeutic nucleic acid may further encode a growth factor selected from epidermal growth factor, interleukin-2, interleukin-4, interleukin-6, tissue growth factor-α, insulin growth factor-1, or fibroblast growth factor.

Toxin purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella* cytotoxin, *Aeromonoas* enteroxotins, toxic shock syndrome toxin-1 (TSST-1), Staphylococcal enterotoxin A (SEA), B (SEB), or C (SEC), Streptococcal entertoxins and the like. Such bacteria include, but are not limited to, strains of a species of entertoxigenic *E. coli* (ETEC), enterohemorrhagic *E. coli* (e.g., strains of serotype 0157:H7), Staphylococcus species (e.g., *Staphylococcus aureus, Staphylococcus pyogenes*), *Shigella* species (e.g., *Shigella bodyii,* and *Shigella sonnei*), *Salmonella* species (e.g., *Salmonella typhi, Salmonella chlorea-suis, Salmonella enteritidis*), *Clostridium* species (e.g., *Clostridium perfringens, Clostridium dificile, Clostridium botulinum*), *Camphlobacter* species (e.g., *Camphlobacter jejuni, Camphlobacter fetus*), *Heliobacter* species, (e.g., *Heliobacter pylori*), *Aeromonas* species (e.g., *Aeromonas sobria, Aeromonas hydrophila, Aeromonas caviae*), *Pleisomonas shigelloides, Yersina enterocolitica, Vibrios* species (e.g., *Vibrios chloerae, Vibrios parahemolyticus*), *Klebsiella* species, *Pseudomonas aeruginosa,* and *Streptococci.* See, e.g., Stein, ed., *INTERNAL MEDICINE,* 3rd ed., pp. 1–13, Little, Brown and Co., Boston, (1990); Evans et al., eds *Bacterial Infections of Humans: Epideniology and Control,* 2d. Ed., pp. 239 . 254, Plenum Medical Book Co., New York (1991); Mandell et al., *Principles and Practice of Infectious Diseases,* 3d. Ed., Churchill Livingstone, New York (1990); Berkow et al, eds., *The Merck Manual,* 16th edition, Merck and Co., Rahway, N.J., 1992; Wood et al., *FEMS Microbiology Immunology,* 76:121–134 (1991); Marrack et al, *Science,* 248:705–711 (1990), the contents of which references are incorporated entirely herein by reference.

The therapeutic nucleic acid may encode at least one member selected from a single chain ribosome inhibitory protein acting to block expression of an abnormal protein in the chimeric receptor cell or tissue; a cytokine; or a growth factor.

Cytokines that are produced by lymphocytes are termed lymphokines, whereas peptides produced by monocytes or macrophages are given the term monokines. Thus, the terms cytokines, lymphokines, and interleukins may be used interchangeably to designate those peptide molecules that modulate host responses to foreign antigens or host injury by regulating the growth, mobility and differentiation of leukocytes and other cells.

Known cytokines include interleukins (IL) IL-1 (also endogenous pyrogen (EP), lymphocyte activating factor (LAF), mononuclear cell factor, catabolic, osteoclast activating factor and hematopoietic 1), IL-2 (also T cell growth factor (TCGF)), IL-3 (multicolony stimulating factor (M-CSF), P-cell stimulating factor, WEHI-3B factor, mast-cell growth factor and histamine-producing factor), IL-4 (B-cell growth factor (BCGF), B-cell stimulatory factor-1 (BSF-1), IL-5 (T-cell replacing factor (TRF), B-cell growth factor II (BCGF-II) (BCGF-II), eosinophil differentiation factor (EDF), IL-6 ($\beta_2$ interferon (IFN-$\beta_2$), B-cell stimulating factor 2 (BSF-2), 26-kDa protein, hybridoma/plasmacytoma growth factor (HPGF or IL-HP-2), hepatocyte stimulating factor (HSF), and T-cell activating factor (TAF)), IL-7, IL-8 (neutrophil activating protein 1 (NAP-1), IL-10 (also cytokine synthesis inhibitory factor (CSIF);

tissue necrosis factors (TNF) TNFα (also lymphotoxin (LT) and TNFβ (also macrophage derived TNF); interferons (IFN) IFNα and IFNβ (also type I- IFN) and IFNγ (also type II IFN) and tissue growth factor (TGF) β.

Cytokines modulate target cells by interacting with cytokine receptors on the target cell. Principal cell sources of cytokines include T lymphocytes, B lymphocytes, macrophages, stromal cells, monocytes, leukocytes, and platelets. While cytokine specific receptors are specific for a given cytokine, cytokine receptors are grouped into families based on shared features. The first group of cytokine receptors is the hemopoietin group which include immune system cells that bind IL-2, IL-3, IL-4, IL-6 and IL-7. A second receptor family is the TNF receptor family which bind both TNFα and TNFβ. A third family is the immunoglobulin (Ig) superfamily receptor family, which contains an Ig sequence like motif and includes human IL-1 and IL-6 receptors. See, e.g., Dawson, In *Lymphokines and Interleukins* (Dawson, ed.) CRC Press, Boca Raton, Fla. (1991); Mosmann et al, *Immunol. Rev.* 123: 209–229 (1991); Mosmann et al, *Immunol. Today* 12:A59–A69 (1991); Sherry et al, *Curr. Opinion Immunol.* 3:56–60 (1991); Paul, *Blood* 77:1859–1870 (1991); Dower et al, *J. Clin. Immunol.* 10:289–299 (1990).

According to another aspect of the present invention, a cytotoxic or a chemotherapeutic agent may be attached directly to a delivery vector having an env binding domain or to an antibody or fragment, or a growth factor, that preferentially binds pathologic cells as target cells. The targets for this type of therapy can also be growth factor receptors, differentiation antigens, or other less characterized cell surface antigens specifically associated with other pathologic cells. It is now established that many cancers overproduce growth factor receptors which can function as oncogenies or in an autocrine way to promote the growth of the cancer cells (Pastan and Fitzgerald, 1991; Velu et al, 1987; Kawabi et al, 1988; Hellstrom & Hellstrom, 1989). For example, the epidermal growth factor receptor is present in large amounts (up to $3 \times 10^6$ receptors per cell) in many squamous cell and epidermoid carcinomas, glioblastomas, and some metastatic ovarian and bladder cancer (Hender et al, 1984; Jones et al, 1990; Lau et al, 1988). By contrast, normal cells can contain a magnitude less receptors per cell (Dunn et al, 1986). In another example the interleukin-2 (IL-2) receptor is present in substantially higher numbers on the cells of patients with adult T cell leukemia (ATL; $3 \times 10^4$ receptors per cell) than in normal T cells.

Other differentiation antigens that occur on normal cells, such as, but not limited to, B lymphocytes, are often also present on tumor cells. Because such antigens are not present on the stem cells that produce B cells, any mature B cells that are killed by targeted therapy will be replaced from the stem cell population from the stem cell population, whereas the cancer cells will not be replaced (Ghetie et al, 1988). Finally, there are antigens preferentially expressed on cancer cells whose functions are not yet understood. Some of these, such as carcinoembryonic antigens (CEA) (Muraro et al, 1985), are fetal antigens, which are either not present or only present in small amounts on normal adult tissues. This group also contains antigens of unknown origin that are only defined by their reactivity with a monoclonal antibody (Fraenkel et al, 1985; Varki et al, 1984; Willingham et al, 1987).

Other non-limiting examples of tumor and cancer specific receptors are Garcia de Palazzo, I. E. et al., *Cancer Res.* 53(14):3217–3220 (1993) as a type III Epidermal growth factor receptor (EGFR) deletion mutant which is expressed in mon-small cell lung cancer (NSCLC) and Noble, P. J. et al., *J. Neurochem.* 61(2);752–755 (1993), A specific GABAA receptor subunit expressed in a human neuroblastoma IMR-32 cell line.

Single-chain antigen-binding proteins which may be used as components of therapeutic or diagnostic delivery vectors of the present invention have numerous advantages in clinical applications because of their small size. These proteins are cleared from serum faster than monoclonal antibodies or Fab fragments. Because Fv, F(ab')$_2$ or Fab lack the Fc portion of an antibody, which is recognized by cell receptors, they have a lower background for use in imaging applications and they are less immunogenic. Such Ab fragments are also expected to penetrate the microcirculation surrounding solid tumors better than monoclonal antibodies.

In such a therapeutic delivery vector, the therapeutic agent can be a toxin or toxin fragment or domain; such as a purified or recombinant toxin or toxin fragment comprising at least one functional cytotoxic domain. The toxin may be selected from any suitable toxin, e.g., as presented herein and/or as would be available to one skilled in the art.

Obtaining a safer vector for in vivo gene therapy.

The use of different strategies can be used to increase the margin or safety in vivo gene therapy treatments provided according to the present invention. These strategies, e.g., may include the use of different packaging cell lines; the use of ecotropic, rather than amphotropic-based vectors, and providing means to target retroviral vectors to the desired cell population in vivo.

Use of different packaging cell lines. Concerns with the safety of existing amphotropic-virus based vectors has provided an incentive to discover a novel system for the production of high titered ecotropic retrovirus vectors which are now discovered and provided by the present invention. This strategy relies on the fact that human cells cannot be infected by non-human ecotropic virus, as presented herein, or by hamster leukemia virus. (Stenback et al., *Proc. Soc. Exp. Biol. Med.* 122:1219–1223, 1966). Hamster leukemia virus has been reported (Lieber et al., *Science* 182:56–58 91973) to infect only hamster cells, as attempts to infect mouse, rat, cat, monkey and human cells have failed. Replicating murine ecotropic viruses in hamster cells can also be used according to the present invention. This has been achieved by transfecting the murine, or modified human ecotropic receptors into these minster cells, followed by infection. This strategy takes further advantage of the natural resistance of these cells to replicate amphotropic viruses, and to achieve higher titers of ecotropic expression by the repeated amplification of murine ecotropic viral sequences in these cells.

The so called "ping-pong" strategy of Bestwick et al. (*Proc. Natl. Acad. Sci USA,* 85:5404–5408, 1988), is substantially modified in the present invention, where two retrovirus are used, neither of which can normally replicate in human cells. A chinese hamster cell line expressing Ψ-HaLV and A) is used to provide helper virus, and co-cultivated with a second chinese hamster cell line expressing Ψ-ecotropic MuLV (cell line B), but not expressing the murine ecotropic virus receptor. In this manner, virus propagated in cell line A is able to infect cell line B through the HaLV receptor. Virus replicated in cell line B now has the murine ecotropic viral receptor, and is able to infect cell line A. This process is expected to continue until a theoretical maximum number of particle production is achieved (about $10^9$ to $10^{10}$ plaque forming units (PFU)) (see, e.g., Bodine et al. *Proc. Natl. Acad. Sci. USA* 87:3738–3742, 1990). As discussed herein, it has been shown that amplification of retroviral sequences in mixed packaging line co-cultures is associated with an increased copy number over time in tissue culture (Hesorffer et al. *Hematology/ Oncology Clinic of North America* 5:423–432, 1991). Further, this approach is preferred because it appears that retroviral vector DNA is expressed relatively poorly when it is transfected into cells compared to the levels obtained after proviral integration (Bestwick et al., *Proc. Natl. Acad. Sci USA* 85:5404–5408, 1988; Huang and Gilboa *J. Virol* 50.417–424, 1984).

Following this approach, a chinese hamster cell line is provided containing multiple copies of ecotropic virus sequences integrated into the infected cell's genome, and producing at least about $10^7$–$10^{10}$, preferably about $10^9$ to $10^{10}$ PFV, with no particles, recombinant or otherwise, capable of infecting human cells, unless their virus receptors are modified according to the present invention. To insure that this result is obtained, appropriate viral infectivity assays are performed with a variety of human and murine cells lines, normally used to detect viral infectivity. This approach is expected to yield a far safer packaging line for in vivo, in situ, or ex vivo gene therapy than previously available.

HaLV can be cloned and a deletion in its packaging signal produced. The removal of the packaging signal is obtainable by known method steps. Next, transfection and stable expression of a murine ecotropic virus receptor into a CHO hamster cell can be provided according to known method steps, e.g., as described in Yoshimoto et al. (1993). Optionally, a cloned helper virus can be introduced into these cells as split genomes for added safety. In the case of the murine ecotropic virus helper, plasmids pgag-polgpt and penv, e.g., as derived from the 3PO plasmid representing the ecotropic Moloney murine leukemia virus with a 134 base pair deletion of the Ψ packaging sequences, are readily obtained from commercial sources or published investigators as presented herein. Such plasmids have been successfully used to generate PCLs with somewhat greater safety than those using unsplit helper virus genomes.

To clone HaLV, known procedures are used, e.g., the procedure of Anderson et al. (1991), similar to cloning defective retrovirus particles from a recombinant Chinese Hamster ovary cell line. For example, such clones include the pCHOC.ML10 sequence identified by Anderson or endogenous, polytropic murine leukemia virus (MuLV) isolate, MX27 (Stoye and Coffin, 1987). The later probe consists of a 12.3 kb mouse genomic fragment encompassing a complete 9.3 kb provirus genome. Hamster C-type related sequences can be isolated from a randomly primed CDNA library of particle RNA in lgt10. If the later probe is used, low stringency hybridization can be to identify plaques of interest. Extracellular particles can then be prepared from culture fluid recombinant CHO cell subclone, e.g., 3-3000-44 (Lasky et al., 1986). This subclone was derived from dihydrofolate reductase (dhrf)-deficient CHO-DuxB11 cells (Simonsen and Levinson, 1983; Urlab and Chasin, 1980) following transection with an expression vector containing the genes for murine dhfr and recombinant envelope glycoprotein (gp120) of human immunodeficiency virus type 1 (HIV-1). The CHO-K1 cell line (progenitor of CHO-DUXB11 line) was originally derived from an ovarian biopsy of an adult Chinese Hamster (Puck et al. 1958) and is readily available from commercial sources such as the American Type Culture Collection (ATCC). Alternatively, repair of the hamster sequence with an equivalent portion of the murine ecotropic virus can be used. Virus particles are expected to be so produced. Since the pCHOC.ML10 sequence is said to contain multiple interruptions of potential coding sequences in all three reading frames of the endonuclease gene, if the clone does not encode an intact endonuclease, the endonuclease region can be replaced with that of a homologous retrovirus genome, such as from ecotropic MuLV. The HaLV surface envelope proteins can then be appropriately expressed so that the particles can infect other hamster cells; all other HaLV genes are not essential (LTRs possibly excluded), and replaceable by homologous MuLV sequences. To delete the Ψ region of the clone HaLV, e.g., the methodology of Mann et al. can be used (*Cell* 33:153–159 (1983)).

As a non-limiting example, the use of a CVR polypeptide of the present invention for gene delivery is expected to lower the potential incidence of cancer and related diseases during gene therapy, due to the lack of non-target cell association of a delivery vector according to the present invention, relative to, e.g., the use of an amphotropic viral vector.

There are thus several advantages to therapeutic methods of the present invention. First, any recombinant viruses that may arise will not be able to infect human cells, as murine ecotropic viruses cannot replicate in these cells. Furthermore, the gene therapist will be able to limit with ecquisite specificity the infection only to those target cells desired to be infected. Potential random insertions of viruses all over the human genome in various types of organs will not be expected or shown to occur, as would be expected whenever human infectable amphotropic-retroviruses-based vectors are used. In addition, because methods of the present invention use a human viral receptor protein which is minimally modified, the possibility of rejection of the infected human cells by the immune system is substantially reduced or eliminated.

A preferred aspect of the present invention, particularly for in vivo methods, is the method of treating an animal using a delivery vector which permits specific targeting of cells to be infected by recombinant, non-human specific ecotropic viruses which provide a therapeutic effect on a target cell. Non-limiting examples of such an agent include a fusion protein encompassing the $V_H$ and $V_L$ regions of a specific antibody to a cell surface molecule (such as, but not limited to, an MHC Class 1 antigen) joined with an appropriate linker peptide and the mouse ecotropic virus receptor or the modified human ecotropic receptor. Alternatively a ligand for a membrane receptor (such as, but not limited to, the epidermal growth factor receptor) can be used which is fused to the mouse ecotropic virus receptor or the modified human virus ecotropic receptor. The design will be flexible enough so that its specificity can be modified with relative ease.

Antibodies. This invention is also directed to an antibody specific for an epitope of a CVR polypeptide or human viral receptor polypeptide. An antibody of the present invention may be used to prevent or treat retorvirus infection, to detect the presence of, or measure the quantity or concentration of, a CVR polypeptide or human viral receptor polypeptide in a cell or tissue extract, or a biological fluid. See, generally, Coligan, supra, and harlow, infra.

The term "antibody" is meant to include polyclonal antibodies, monoclonal antibodies (mAbs), chimeric antibodies, anti-idiotypic (anti-Id) antibodies, and fragments thereof, provided by any known method steps, such as by hybridomas, recombinant techniques or chemical synthesis. See, e.g., Lane, infra, Ausubel, infra, Sambrook, infra, and Colligan, Infra.

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as, but not limited to, amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies which may be evoked by other antigens.

Polyclonal antibodies are heterogenous populations of antibody molecules derived from the sera of animals immunized with an antigen.

Monoclonal antibodies are a substantially homogenous population of antibodies to specific antigens which bind a specific epitope on the antigen. Mabs may be obtained by methods known to those skilled in the art. See, for example Kohler and Milstein, *Nature* 256:495–497 (1975) and U.S. Pat. No. 4,376,110, see, e.g., Ausubel et al. eds. *Current Protocols in Molecular Biology,* Greene Publishing Associates and Wiley Interscience, N.Y., (1987, 1992); and Harlow and Lane, *Antibodies: A Laboratory Manual,* Cold Spring Harbor Laboratory (1988); Coligan et al, eds., *Current Protocols in Immunology,* Green Publishing Associates and Wiley Wiley Interscience, N.Y. (1992, 1993). Such antibodies may be of any immunoglobulin class such as IgG, IgM, IgE, IgA, or any subclass thereof. A hybridoma producing a Mab of this invention may be cultivated in vitro or in vivo. Production of high titers of Mabs in vivo production makes this the presently preferred method of production. Briefly, cells from the individual hybridomas are injected intraperitoneally into mice to produce ascites fluid containing high concentrations of the desired mAbs. Mabs of isotype IgM or IgG may be purified from such as, but not limited to cites fluids, or from culture supernatant, using column chromatography methods or other methods steps known in the art.

Chimeric antibodies are molecules different portions of which are derived from different animal species, such as those having a variable region derived from a murine mAb and a human immunoglobulin constant region. Chimeric antibodies and methods for their production are known in the art (see, for example, Neuberger et al., *Nature* 314:268–270 (1985); Sun et al., *Proc. Natl. Acad. Sci. USA* 84:214–218 (1987); Better et al., *Science* 240:1041–1043 (1988); Better, M. D. International Patent Publication WO 9107494, Lane, infra; Colligan, infra, which references are hereby entirely incorporated by reference).

An anti-idiotypic (anti-id) antibody is an antibody which recognizes unique determinants generally associated with the antigen-binding site of an antibody. An Id antibody can be prepared by immunizing an animal of the same species and genetic type (e.g. mouse strain) as the source of the Mab with the Mab to which an anti-Id is being prepared. The immunized animal will recognize and respond to the idiotypic determinants of the immunizing antibody by producing an antibody to these idiotypic determinants (the anti-Id antibody).

The anti-Id antibody may also be used as an "immunogen" to induce an immune response in yet another animal, producing a so-called anti-anti-Id antibody. The anti-anti-Id may bear structural similarity to the original Mab which induced the anti-Id. Thus, by using antibodies to the idiotypic determinants of a Mab, it is possible to identify other clones expressing antibodies of identical specificity.

Accordingly, mAbs generated against a CVR polypeptide or human viral receptor polypeptide of the present invention may be used to induce anti-Id antibodies in suitable animals, such as, but not limited to, BALB/c mice. Spleen cells from such immunized mice are used to produce anti-Id hybridomas secreting anti-Id mAbs. Further, the anti-Id Mabs can be coupled to a carrier such as, but not limited to, keyhole limpet hemocyanin (KLH) and used to immunize additional BALB/c mice. Sera from these mice will contain anti-anti-Id antibodies that have the binding properties of the original Mab specific for an a CVR polypeptide or human viral receptor polypeptide epitope.

The anti-Id mAbs thus have their own idiotypic epitopes or "idiotopes" structurally similar to the epitope being evaluated, such as an epitope of a CVR polypeptide or human viral receptor polypeptide.

Such an anti-Id Abs can be used also as binding domains for delivery vectors of the present invention.

The term "antibody", as presented above, is also meant to include both intact molecules as well as fragments thereof, such as, but not limited to, for example, Fv, Fab and F(ab')$_2$, which are capable of binding antigen. Fv, Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)).

Antibody Diagnostic Assays

It will be appreciated that Fv, Fab and F(ab')$_2$ and other fragments of the antibodies useful in the present invention may be used for the detection and quantitation of a CVR polypeptide or human viral receptor polypeptide according to the methods disclosed herein for intact antibody molecules. Such fragments are typically produced by proteolytic cleavage, using enzymes such as, but not limited to, papain (e.g., to produce Fab fragments) or pepsin (to produce F(ab')$_2$ fragments) or by genetic manipulation, such as, but not limited to, for the construction of Fv fuurion proteins.

The antibodies, or fragments of antibodies, of the present invention may be used to quantitatively or qualitatively detect the presence of cells which express a CVR polypeptide or human viral receptor polypeptide on their surface or intracellularly. This can be accomplished by immunofluorescence techniques employing a fluorescently labeled antibody (see below) coupled with light macroscopic, flow cytometric, or fluorometric detection.

The antibodies of the present invention may be employed histologically, as in immunofluorescence or immunoelectron microscopy, for in situ detection of a CVR polypeptide or human viral receptor polypeptide. Through the use of such a procedure, it is possible to determine not only the presence of a CVR polypeptide or human viral receptor polypeptide, but also its distribution on the examined tissue.

Additionally, the antibody of the present invention can be used to detect the presence of soluble a CVR polypeptide or human viral receptor polypeptides in a biological sample, such as, but not limited to, a means to monitor the presence and quantity of a CVR polypeptide or human viral receptor polypeptide used therapeutically.

Such immunoassays for a CVR polypeptide or human viral receptor polypeptide typically comprise incubating a biological sample, such as a biological fluid, a tissue extract, freshly harvested cells such as lymphocytes or leukocytes, or cells which have been incubated in tissue culture, in the presence of a detectably labeled antibody capable of identifying H13 protein, and detecting the antibody by any of a number of method steps known in the related arts.

The biological sample may be treated with a solid phase support or carrier (which terms are used interchangeably herein) such as nitrocellulose, or other solid support which is capable of immobilizing cells, cell particles or soluble proteins. The support may then be washed with suitable buffers followed by treatment with the detectably labeled CVR polypeptide- or human viral receptor polypeptide-specific antibody. The solid phase support may then be washed with the buffer a second time to remove unbound antibody. The amount of bound label on said solid support may then be detected by conventional means.

B "solid phase support" or "carrier" is intended any support capable of binding antigen or antibodies. Well-known supports, or carriers, include glass, polystyrene, polypropylene, polyethylene, dextran, nylon, amylases, natural and modified celluloses, polyacrylamides, and magnetite.

The binding activity of a given lot of anti-CVR polypeptide-or anti-human viral receptor polypeptide antibody may be determined according to well-known methods. Those skilled in the art will be able to determine operative and optimal assay conditions for each determination by employing routine experimentation.

One of the ways in which the CVR polypeptide- or human viral receptor polypeptide-specific antibody can be detectably labeled is by linking the same to an enzyme and use in an enzyme immunoassay (EIA) according to known methods steps.

Detection may be accomplished using any of a variety of other known immunoassays, see, e.g., *Laboratory Techniques and Biochemistry in Molecular Biology,* Work, et al., North Holland Publishing Company, New York (1978); Lane, infra, Colligan, infra, Ausubel, infra, Sambrook, infra, each incorporated entirely herein by reference.

It is also possible to label the antibody with a fluorescent compound or by using fluorescence emitting metals such as $^{135}$Eu, or others of the lanthanide series. These metals can be attached to the antibody using such metal chelating groups as diethylenetriaminepentaacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemilumine- scent reaction. The presence of a bioluminescent protein is determined by detecting the presence of luminescence. Important bioluminescent compounds for purposes of labeling are luciferin, luciferase and aequorin.

The antibody molecules of the present invention may be adapted for utilization in an immunometric assay, also known as a "two-site" or "sandwich" assay.

Typical, and preferred, immunometric assays include "forward" assays in which the antibody bound to the solid phase is first contacted with the sample being tested to "extract" the antigen from the sample by formation of a binary solid phase antibody-antigen complex. After a suitable incubation period, the solid support is washed to remove the residue of the fluid sample, including unreacted antigen, if any, and then contacted with the solution containing an unknown quantity of labeled antibody (which functions as a "receptor molecule"). After a second incubation period to permit the labeled antibody to complex with the antigen bound to the solid support through the unlabeled antibody, the solid support is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

Tansgenic and Chimeric Non-Human Mammals

The present invention is also directed to a transgenic non-human eukaryotic animal (preferably a rodent, such as, but not limited to, a mouse) the germ cells and/or somatic cells of which contain genomic DNA according to the present invention which codes for a CVR polypeptide or viral receptor polypeptide capable as serving as a viral receptor. The nucleic acid encoding a CVR polypeptide or viral receptor polypeptide is introduced into the animal to be made transgenic, or an ancestor of the animal, at an embryonic stage, preferably at the one-cell, or fertilized oocyte stage, and generally not later than about the 8-cell stage. The term "transgene," as used herein, means a gene which is incorporated into the genome of the animal and is expressed in the animal, resulting in the presence of protein in the transgenic animal.

There are several means by which such a gene can be introduced into the genome of the animal embryo so as to be chromosomally incorporated and expressed according to known methods.

Chimeric non-human mammals in which fewer than all of the somatic and germ cells contain nucleic acid encoding a CVR polypeptide or viral receptor polypeptide are also provided by the present invention. Such animals are produced when fewer than all of the cells of the morula are transfected in the process of producing the transgenic mammal.

Chimeric non-human mammals having human cells or tissue engrafted therein are also encompassed by the present invention. Such chimeras can be used for testing expression of CVR polypeptides or viral receptors in human tissue and/or for testing the effectiveness of therapeutic and/or diagnostic agents associated with delivery vectors which preferentially bind to a CVR polypeptide or viral receptors of the present invention. Methods for providing chimeric non-human mammals are provided, e.g., in U.S. Ser. Nos. 07/508,225, 07/518,748, 07/529,217, 07/562,746, 07/596, 518, 07/574,748, 07/575,962, 07/207,273, 07/241,590 and 07/137,173, which are entirely incorporated herein by reference, for their description of how to engraft human cells or tissue into non-human mammals.

The techniques described in Leder, U.S. Pat. No. 4,736,866 (hereby entirely incorporated by reference) for producing transgenic non-human mammals may be used for the production of the transgenic non-human mammal of the present invention. The various techniques described in Palmiter, R. et al., *Ann. Rev. Genet.* 20:465–99 (1986), the entire contents of which are hereby incorporated by reference, may also be used.

The animals carrying a nucleic acid encoding a CVR polypeptide or viral receptor can be used to test compounds or other treatment modalities which may prevent, suppress or cure a human retrovirus infection or a disease resulting from such infection for those retroviruses which infect the cells using the a CVR polypeptide or viral receptor as a receptor. These tests can be extremely sensitive because of the ability to adjust the virus dose given to the transgenic or chimer non- human animals of this invention. Such animals can also serve as a model for testing of diagnostic methods for the same human pathologies or diseases. Such pathologies or diseases include, but are not limited to AIDS, HTLV-induced leukemia, tumors, cancer, viral infections and the like. Transgenic or chimeric animals according to the present invention can also be used as a source of cells for cell culture.

Having now generally described the invention, the same will be more readily understood through reference to the following example which is provided by way of illustration, and is not intended to be limiting of the present invention.

EXAMPLE I

General Materials and Methods Cell Lines

The following cell lines were used in the studies described below: CCL120 (ATCC# CCL120), a human B lymphoblastoid cell line; CCL110 (CEM, ATCC# CCL119), a human T lymphoblastoid cell line; SupT1, a human non-Hodgkin's T lymphoma cell line; H9, a single cell clone derived from HUT78, a human cutaneous T cell lymphoma cell line; MOLT4 (ATCC# CRL1582), a human acute lymphoblastic leukemia cell line; HOS (ATCC# CRL1543), a human osteosarcoma cell line; HeLa (ATCC# CCL2), a human epithelioid carcinoma cell line; CHO-K1 (ATCC #61), a Chinese hamster ovary cell line; B10T6R, a radiation-induced thymoma of B10.T(6R) mice; and RL12, a radiation-induced thymoma of C57BL/6Ka mice.

Screening

Human CEM and HUT 78 T-cell CDNA library (lambda gtll) was obtained from Clontech Laboratories Inc. (Palo Alto, Calif.). The human lymphocyte cosmid library (pWE15) was obtained from Stratagene (LaJolla, Calif.). The libraries were screened by the method of Maniatis et al. (Maniatis, T. et al. *Cell* 15:887–701 (1978)). The BamHl-EcoRI fragment, containing the entire open reading frame of ERR cDNA (pJET) was provided by Drs. Albritton and Cunningham (Harvard Medical School, Boston, Mass.). This DNA was labelled with $^{32}$P by nick translation to a specific activity of about $2\times10^6$ cpm/µg and used as a hybridization probe.

Southern Blot Analysis

High relative mass DNA was prepared from cells as described by Blin, N. et al. (*Nucl. Acids Res.* 3:2303–2308 (1976)) and modified by Pampeno and Meruelo (Pampeno, C. L. et al. *J. Virol.* 58:296–306 (1986)). Restriction endonuclease digestion, agarose gel electrophoresis, transfer to nitrocellulose (Schleicher & Schuell, Inc., Keene, N.H.), hybridization and washing was as described (Pampeno, C. L. et al. supra: Brown, G. D. et al. *Immunogenetics* 27:239–251 (1988)).

Northern Blot Analysis

Total cellular RNA was isolated from cells by the acid guanidinium thiocyanate-phenol-chloroform method (Chomczynski, P. et al. *Anal. Biochem.* 162:156–159 (1987)). The DNA was electrophoresed in 1% formaldehyde agarose gels and transferred to Nytran filters (Schleicher & Schuell, Inc., Keene, N.H.). The hybridization and washing was performed according to Amari, N. M. B. et al. (*Mol. Cell. Biol.* 7:4159–4168 (1987)).

DNA Sequence Analysis cDNA clones from positive phages were recloned into the EcoRI site of plasmid vector pBluescript (Stratagene). Uni-directional deletions of the plasmids were constructed by using exonuelcease III and S1 nuclease, and sequenced by the dideoxy chain termination methods (Sanger, F. S. et al. *Proc. Natl. Acad. Sci. USA* 74:5463–5467 (1977)) with Sequenase reagents (U.S. Biochemical Corp., Cleveland, Ohio). Restriction maps of positive cosmid inserts were determined using T3 or T7 promoter-specific oligonucleotides to probe partially digested cosmid DNA as described elsewhere (Evans, G. A. et al., *Meth. Enzymol.* 152:604–610 (1987)). EcoRI-EcoRI or EcoRI-HindIII fragments in the cosmids were subcloned into Pbluescript or pSport 1 (GIBCO BRL, Gaithersburg, M.D.). The exons and exon-intron junctions were sequenced using synthetic oligonucleotides as primers. Sequences were compiled and analyzed using the Genetics computer group sequence analysis software package (Devereux, J. et al., *Nucl. Acids Res.* 12:387–395 (1984)).

EXAMPLE II

DNA and Predicted Protein Sequence of H13

The complete nucleotide sequence of H13 (SEQ ID NO:7) including non-coding sequences at the 5' and 3' end of the coding sequence are shown in FIG. 1. This sequence includes the partial sequence originally obtained from clone 7-2 (SEQ ID NO:1); nucleotide 1–6 and 1099–1102 of SEQ ID NO:1 were originally incorrectly determined. FIG. 1 also shows the complete amino acid sequence predicted from the nucleotide sequence (SEQ ID NO:8). This sequence includes the originally described partial amino acid sequence (SEQ ID NO:2) with the exception of the N-terminal Pro-Gly and the C-terminal Pro, which were originally incorrectly predicted iron the nucleotide sequence.

The nucleotide sequence comparison between H13, and ERR is shown in FIG. 2 and the amino acid sequence comparison of H13, ERR and TEA is shown in FIG. 3.

The homology between the compared sequences is very high, for example 87.6% homology between H13 and ERR DNA, and 52.3% homology between H13 and TEA amino acids.

EXAMPLE III

Presence and Expression of the H13 Gene in Human Cells

Figure 6:
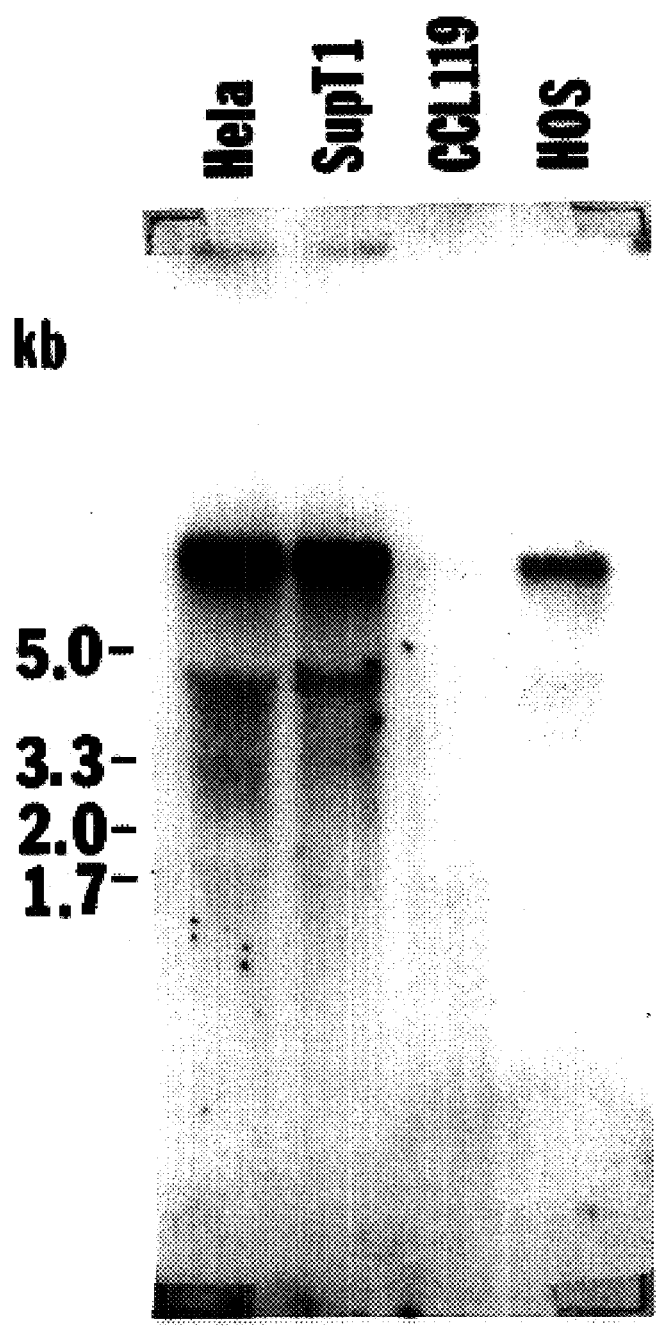
FIG. 6 shows an autoradiogram of H13 gene expression. RNA from the indicated human cell lines was hybridized with the H13 CDNA (SEQ ID NO:1).
Figure 7:
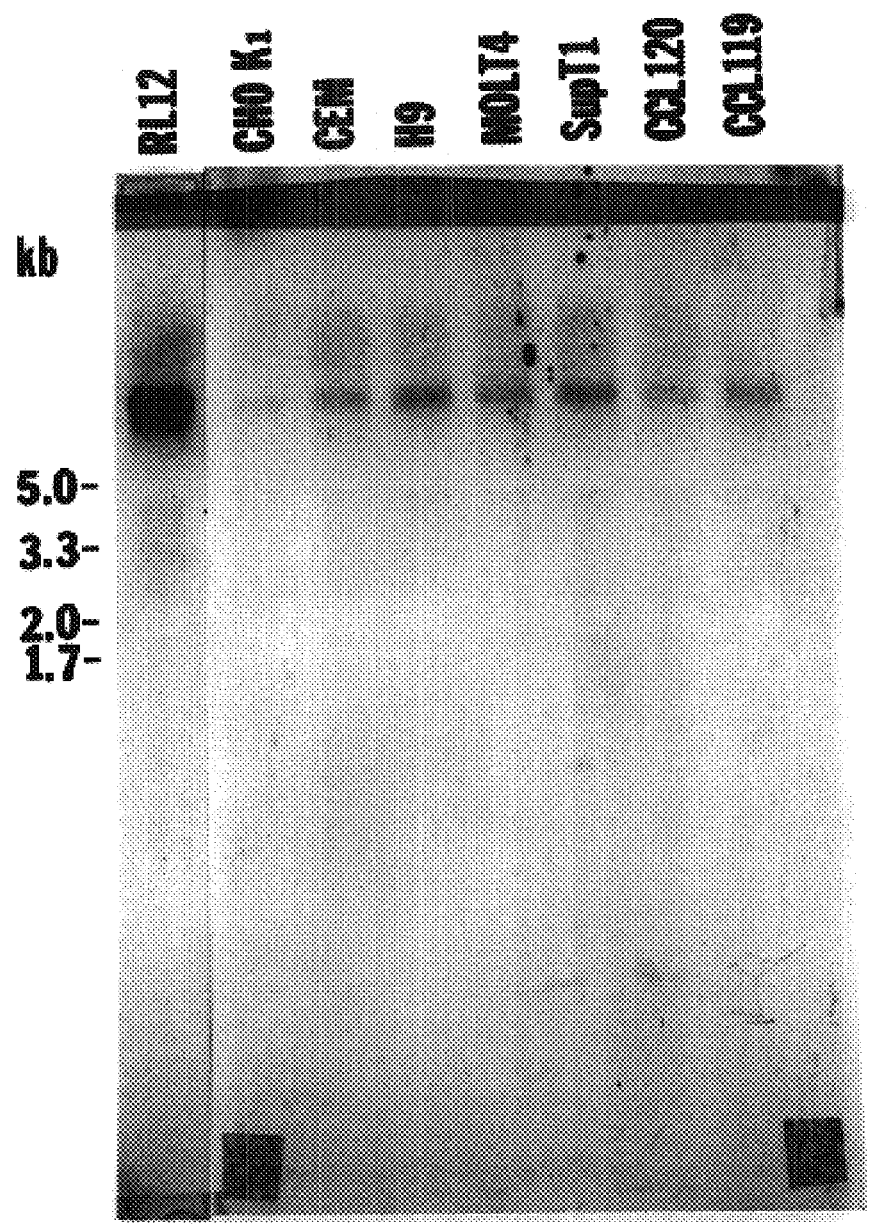
FIG. 7 shows an autoradiogram of the hybridization pattern of RNA of human (CEM, H9, MOLT4, SupT1, CCL120, CCL119), hamster (CHO K1) and mouse (RL12) origin, probed with the KpnI—KpnI fragment (390 bp) of murine ERR CDNA.

By Southern analysis of DNA taken from cells of various species, it was shown that DNA capable of hybridizing with a murine ERR cDNA probe (FIG. 4) and with the H13 cDNA (FIG. 5) was present in cells of 5 human cell lines, including CCL120, CCL119, SupT1, H-9 and MOLT-4, and also in hamster cells (CHO-K1) and murine cells (normal BALB/c mouse thymocytes). H13 gene expression was examined using Northern analysis, using the H13 cDNA probe. The probe detected a transcript of approximately 9 kb in RNA from HeLa, SupT1, HOS and CCL119 cells (FIG. 6). This RNA could also be detected using a murine ERR cDNA probe (FIG. 7).

EXAMPLE IV

Transection of Murine Retroviral Receptor cDNA into Hamster Cells

Murine retroviral receptor (ERR) cDNA was cotransfected into hamster CHO cells, which can not be infected by murine ecotropic retroviruses, with the selectable marker plasmid DNAP, pSV$_2$Neo, using calcium phosphate (Wigler, M. et al., *Cell* 14: 725–731 (1978)). The transfectant expressing the receptor gene was, then, infected by murine radiation leukemia virus (RadLV). Two weeks later after the infection the reverse transcriptase (RT) activity of the supernatant was measured (Stephenson, J. R. et al., *Virology* 48: 749–756 (1972)), and Northern Blot analysis was performed using-a viral probe after preparing its RNA.

Figure 8:
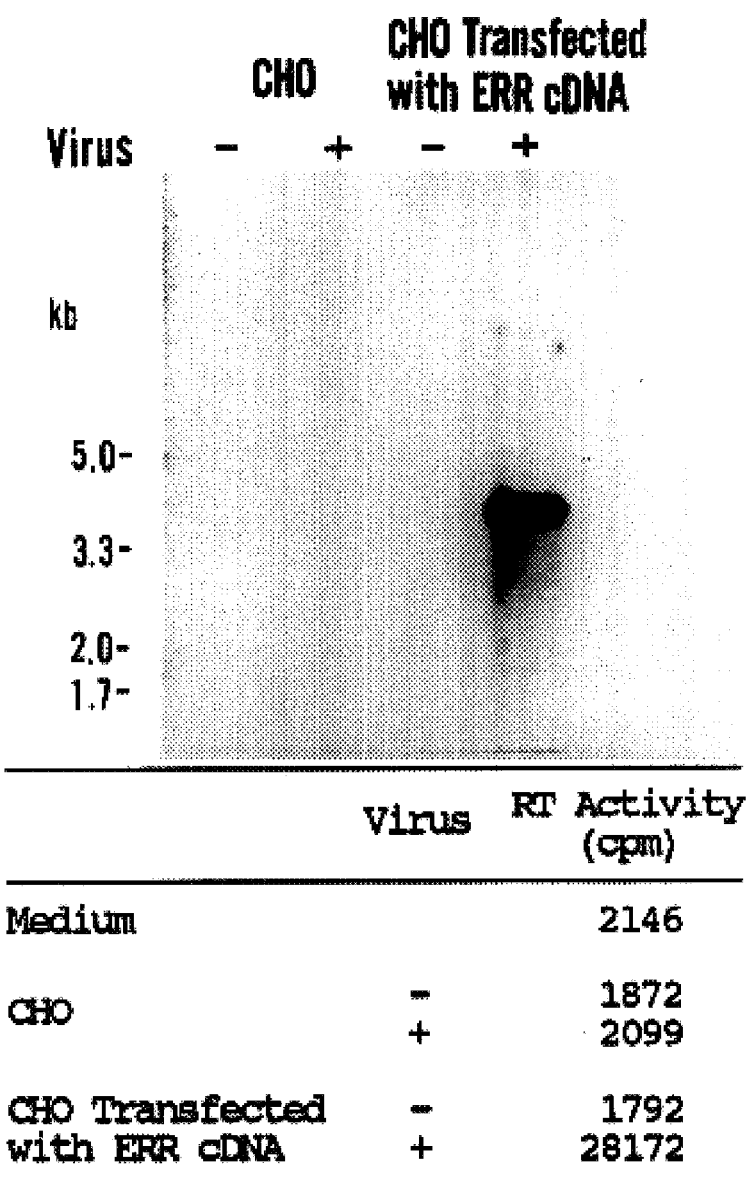
FIG. 8 shows a Northern Blot demonstrating the acquisition of susceptibility to infection with murine ecotropic retrovirus by transection of an infection resistant cell with ERR CDNA. After transection of ERR CDNA into hamster CHO K1 cells, the transfectants expressing the murine retroviral receptor gene were infected with murine radiation leukemia virus (RadLV). Two weeks later, Northern blot analysis was performed using a viral probe, and reverse transcriptase (RT) activity of the cell supernatant was measured.

As shown in FIG. 8, the RT activity detected in untransfected CHO cells which do not express the receptor gene was indistinguishable from the activity of tissue culture medium (background). This indicates that the cells were not infected by MuLV.

Following transection with the ERR cDNA, the RT activity of the transfected cell supernatant was much higher than background (FIG. 8).

The MuLV viral probe detected transcripts in RNA prepared from the transfectant, but not in RNA prepared from untransfected CHO cells. The results indicate that the cells transfected with the ERR cDNA can acquire the susceptibility to ecotropic murine leukemia virus.

EXAMPLE V

Preparation and Use of Antibodies to H-13

Figure 9:
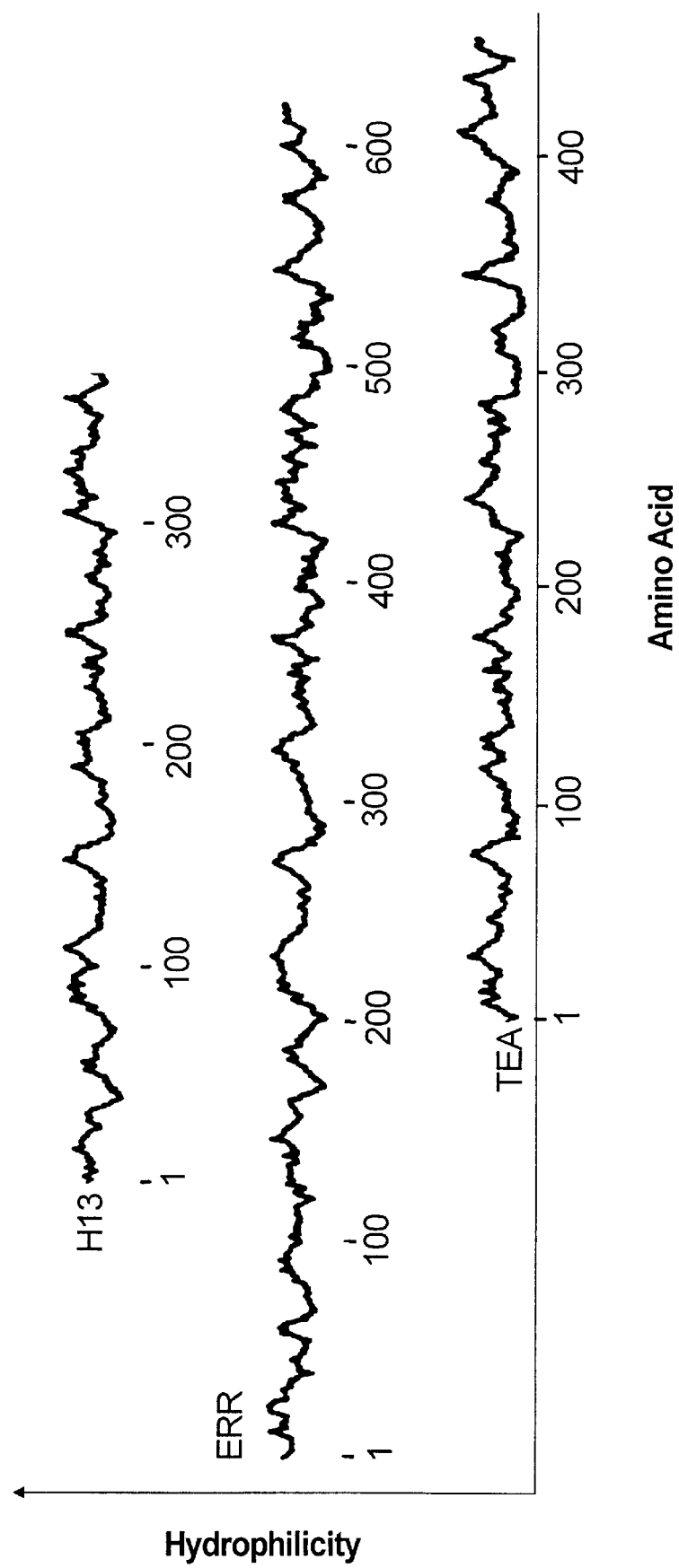
FIG. 9 shows hydropathy plots for H13, ERR and TEA predicted proteins. The vertical axis gives the hydropathicity values from the PEPTIDESTRUCTURE program (See, e.g., Jameson et al., *CABIOS* 4: 181–186 (1988)).
Figure 10:
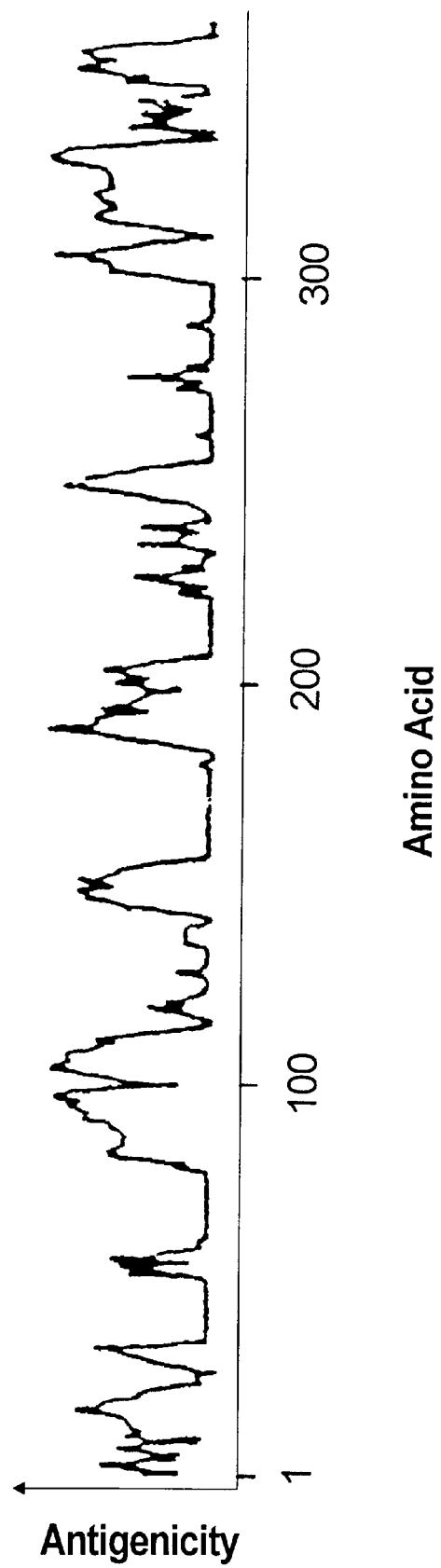
FIG. 10 shows a graph indicating antigenicity of H13 predicted protein, analyzed using the PEPTIDESTRUC-TURE™ program. One of the highly antigenic peptides (amino acid residues 309–367) was prepared using an AccI-EcoRI fragment, as shown in FIG. 14.

It is very difficult to make an H-13-containing fusion protein having the whole predicted protein (SEQ ID NO:2) since the predicted protein is highly hydrophobic, as shown in FIG. 9. In order to predict antigenic epitopes present in the protein, therefore, the computer analysis was carried out using the program of PEPTIDESTRUCTURE (Jameson et al., *CABIOS* 4: 181–186 (1988)). FIG. 10 shows the antigenicity profile of the H-13 protein sequence.

The DNA sequence encoding a highly antigenic portion (SEQ ID NO:2, amino acid residues 309–367) was prepared by cutting with the restriction enzymes AccI and EcoRI yielding a 180 bp AccI-EcoRI fragment. This fragment of H13 cDNA was ligated to the cloning sites of pGEX-2T plasmid vector (Pharmacia LKB Biotechnology), which can express antigens as fusion proteins with glutathione-S-transferase (GST), in the orientation that permit[s] the expression of the open reading frames (Smith, D. B. et al., *Gene* 67: 31–40 (1988)).

Figure 11:
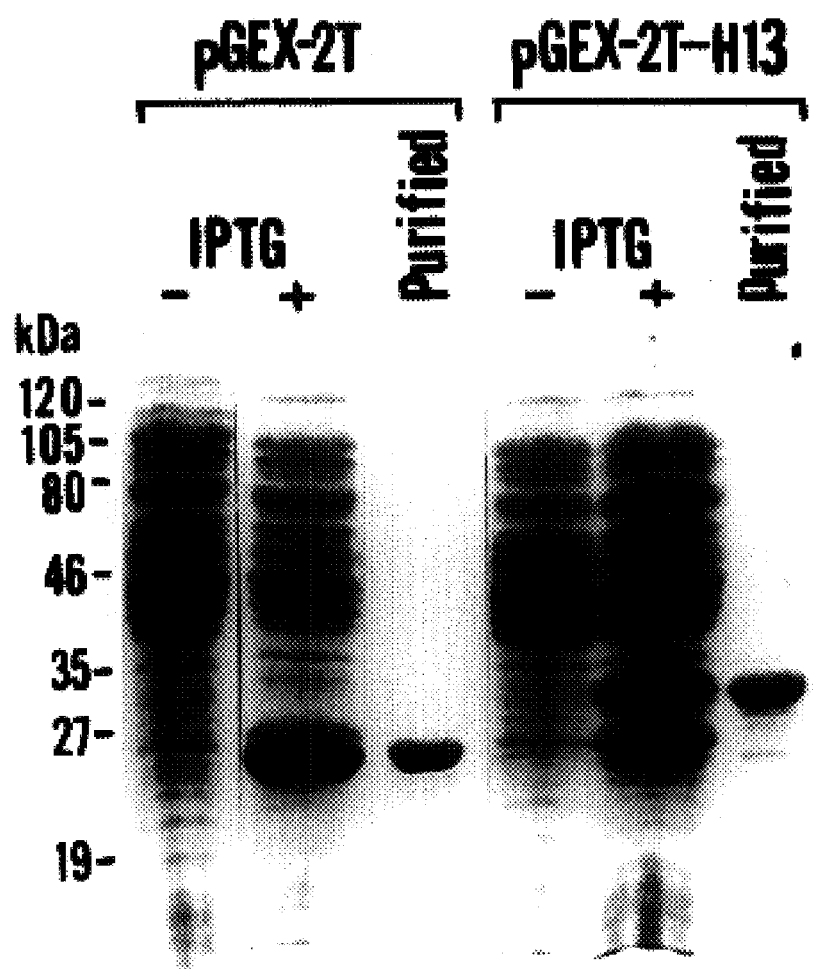
FIG. 11 shows an SDS-PAGE autoradiogram depicting the synthesis of a fusion protein including the H13 protein with glutathione-S-transferase (GST). The fusion protein was prepared by ligating the 180 bp AccI-EcoRI fragment of H13 CDNA to the plasmid pGEX-2T, which expresses antigens as fusion proteins, was induced by addition of isopropyl-beta-thiogalactopyranoside (IPTG), and was purified using glutathione-Sepharose chromatography.

The fusion protein was induced by addition of isopropyl-beta-thiogalactopyranoside (IPTG) to cultures, and was purified using glutathione Sepharose 4B chromatography (Pharmacia LKB Biotechnology) (see FIG. 11). The purified fusion protein injected intramuscularly and subcutaneously into rabbits with Freund's complete adjuvant to obtain antisera.

The antisera are shown to bind specifically to the H-13 protein and epitopic fragments thereof.

Membrane proteins from human cells are prepared according to standard techniques and are separated by polyacrylamide gel electrophoresis, an blotted onto nitrocellulose for Western Blot analysis. The H-13 specific antibodies are shown to bind to proteins on these blots.

EXAMPLE VI

Genetic Mapping of H13

Figure 12A:
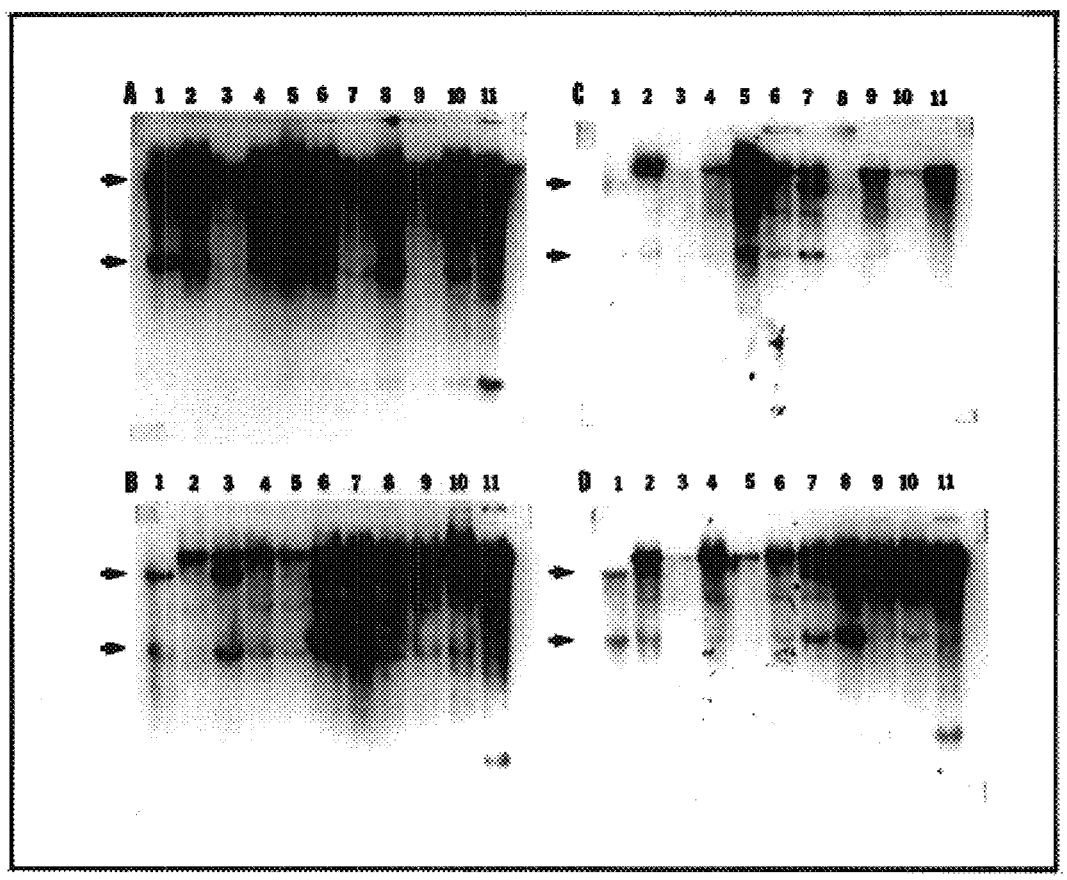
Figure 12B:
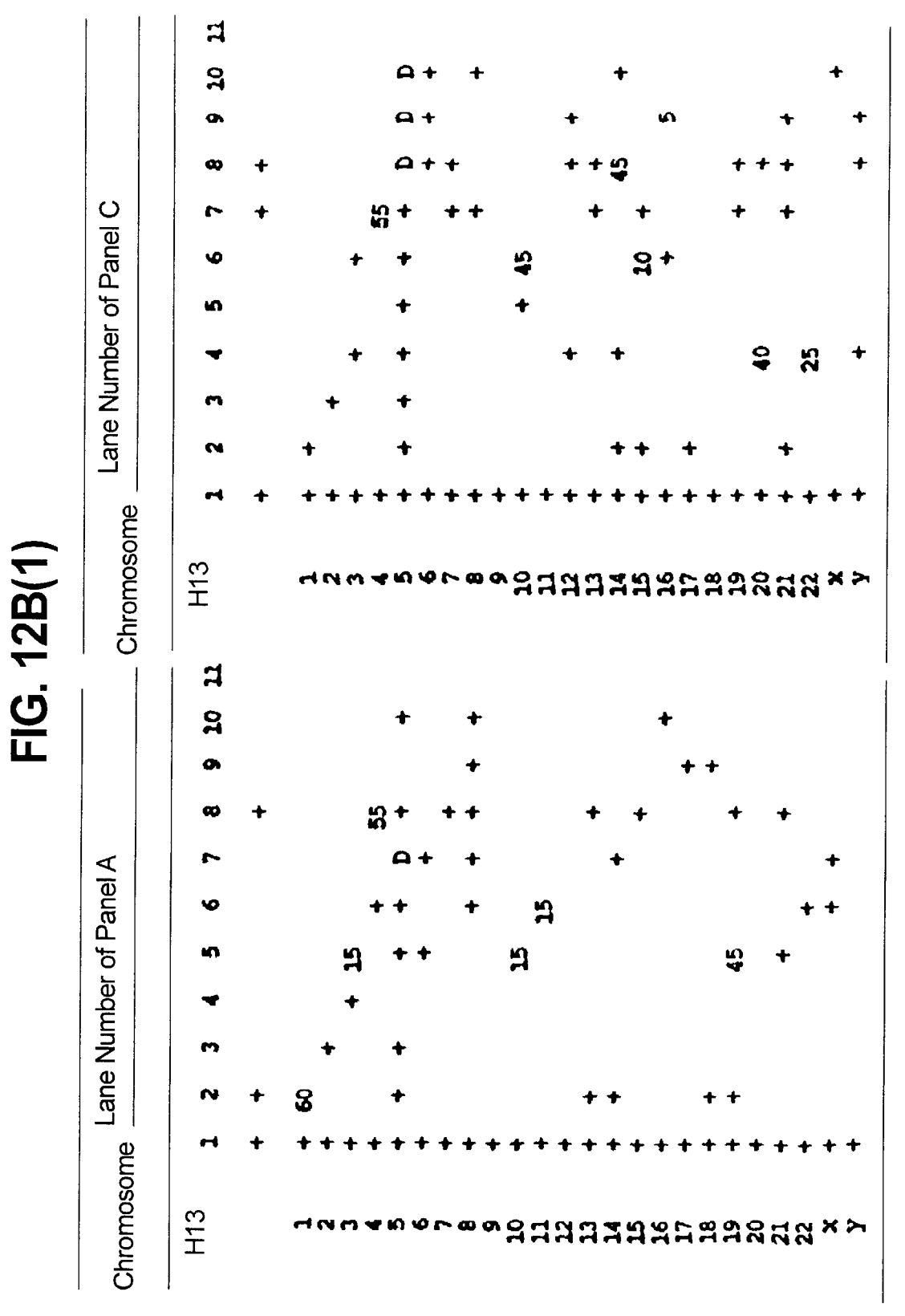

Chromosomal location of the H13 gene was determined using Chromosome Blots (Bios Corp., New Haven, Conn.) containing DNA from a panel of human-hamster somatic cell hybrids (Kouri, R. E. et al., *Cytogenet. Cell Genet.* 51:1025 (1989)). By comparison of which human chromosomes remained in the human-hamster hybrid cell and the expression of H13 CDNA, the H13 gene was mapped to human chromosome 13 (see FIG. 12). Human genes (or diseases caused by mutations therein ) linked to chromosome 13 include: retinoblastoma, osteosarcoma, Wilson's disease, Letterer-Siwe disease, Dubin-Johnson syndrome, clotting factor Vii and X, collagen IV α1 and α2 chains, X-ray sensitivity, lymphocyte cytosolic protein-1, carotid body tumor-1, propionyl CoA carboxylase (α subunit), etc.

EXAMPLE VII

A CVR Polypeptide Encoded by Chimeric H13/ERR DNA and Protein Molecules

Figure 13:
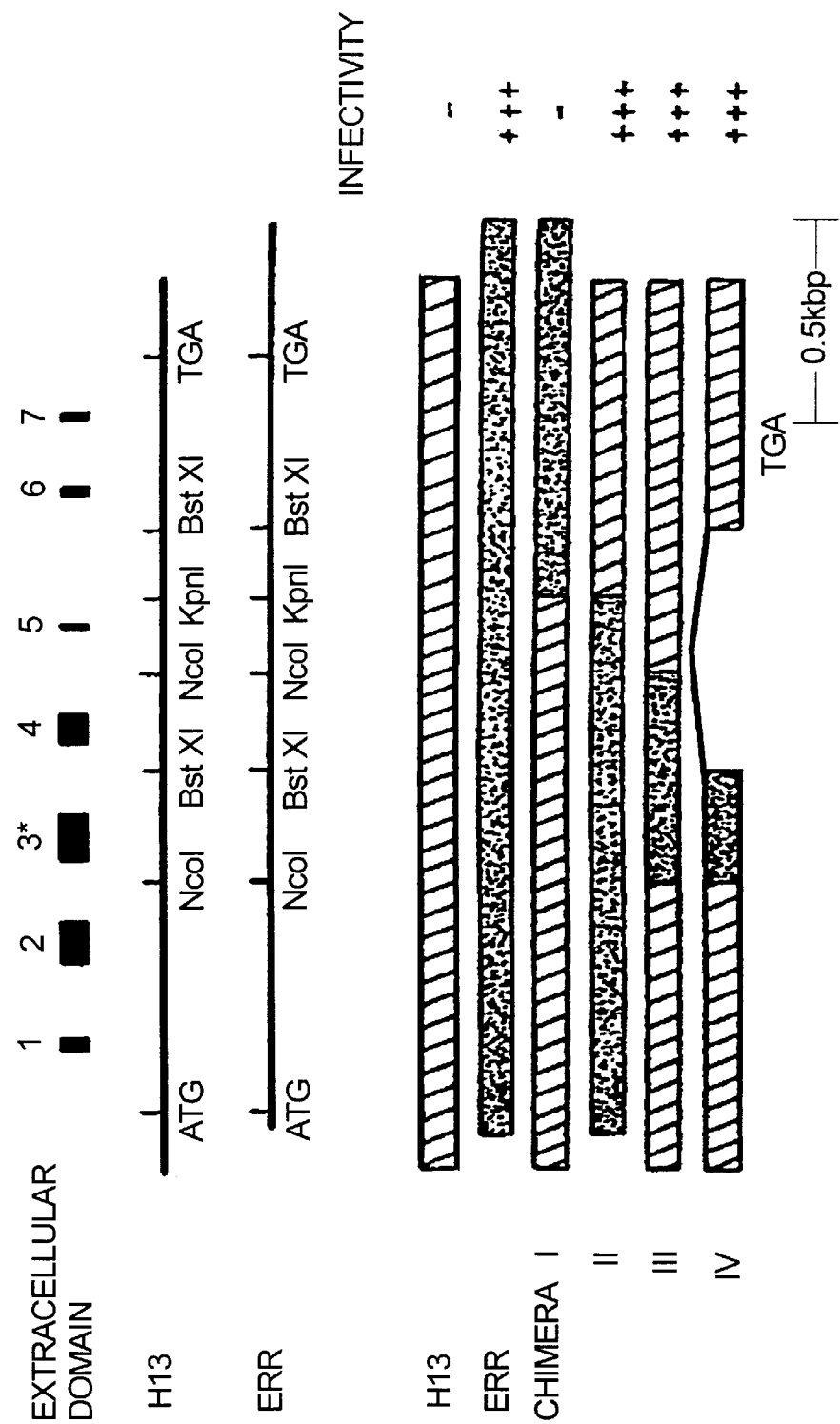
FIG. 13 is a schematic diagram of the genetic structure of the H13 and ERR genes, including four chimeric constructs there between. The infectivity of E-MuLV on human cells transfected with the various constructs is also indicated.
Figure 15:
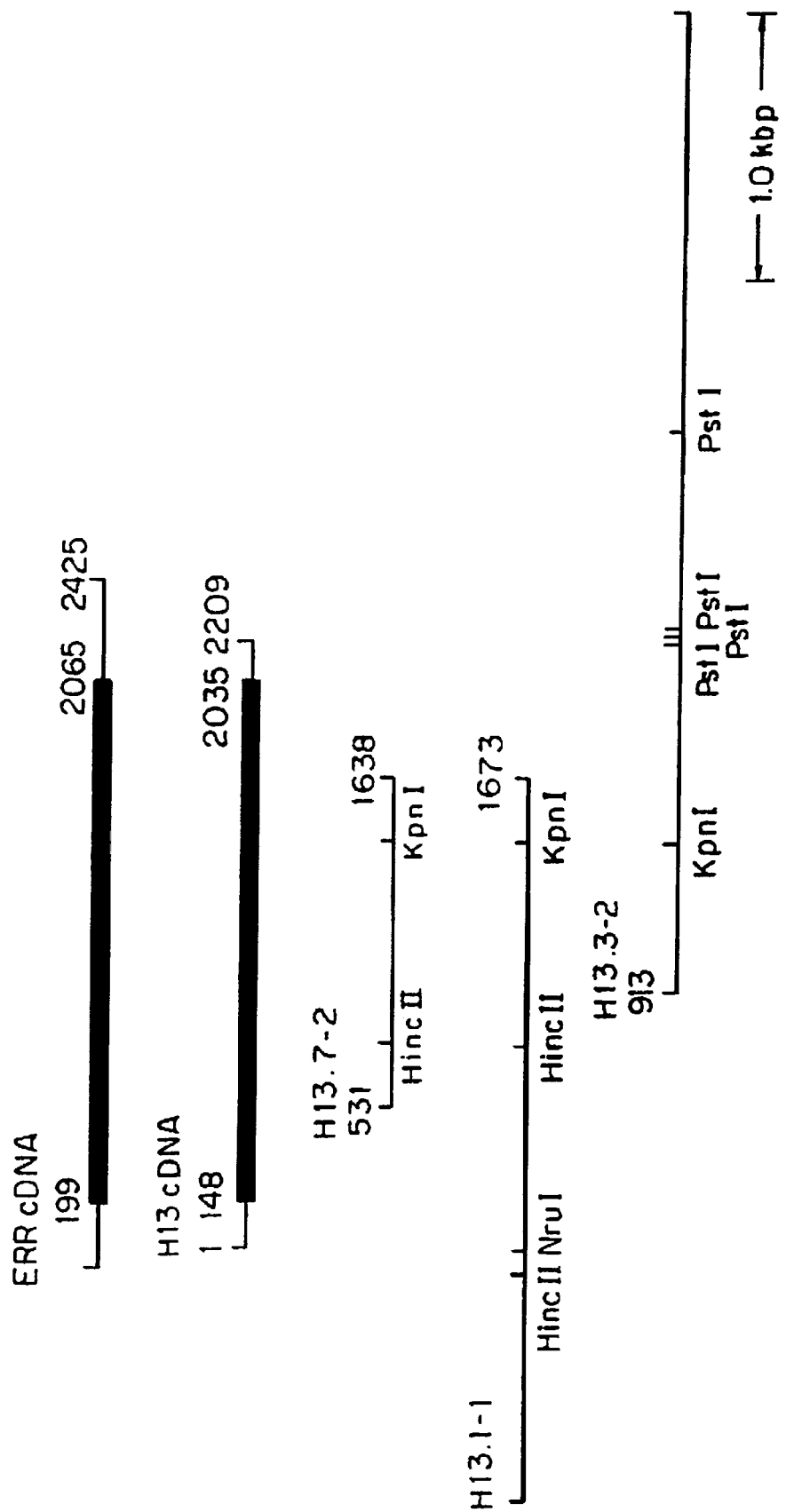
FIG. 15 shows a schematic illustration of several CDNA clones from which the H13 sequence was derived, and their general structure relationship to the murine ERR homolog. Clone 7–2 (H-13.7-2) represents a part of the complete H13 nucleic acid sequence; this was the first H13 clone sequenced, yielding SEQ ID NO:1 and SEQ ID NO:2. Clones 1-1 (H13.1-1) and 3-2 (H13.3-2) each contain parts of the H13 sequence. The combined sequencing of these three clones resulted in the full H13 nucleic acid and amino acid sequences (SEQ ID NO:7 and SEQ ID NO:8, respectively).

Several chimeric molecules between the mouse ERR sequence and the human H13 sequence were produced, and have been designated Chimera I–Chimera IV. Specifically, four regions in H13 cDNA were substituted based on the use of common restriction sites as shown in FIG. 13.

These DNA sequences were transiently transfected into Chinese hamster ovary (CHO) cell lines using pS$^1$5 or pCDM8 expression vectors.

Two days later, these transfectants were tested for their ability to support E-MuLV infection. Cells were infected with a recombinant Moloney E-MuLV designated 2BAG (Price, J. et al., *Proc. Natl. Acad. Sci. USA* 84:156–160 (1987)). This recombinant virus also contained β-galactosidase and neomycin phosphotransferase (neo$^R$) genes which provide a selectable marker and a detectable product. The cells were then grown under selective conditions in the presence of the ant biotic G418 at a concentration of 0.6 mg/ml to select neo$^R$-expressing transfectants. After two weeks, numbers of G418-resistant colonies were counted.

These results indicate that portion of the ERR gene essential for E-MuLV infection is located within NcoI-BstXI restriction sites, and included extracellular Domain 3. Extracellular Domain 3 (as shown in the upper line of FIG. 13) is the region of the receptor protein which is most diverse between the human and mouse sequences, as shown in FIG. 14. The sequences in FIG. 14 (derived from the sequences shown in FIGS. 1–3) were aligned using Genetics computer group sequence analysis software package (Devereux, J. et al, *Nucl. Acids Res.* 12:387–395 (1984)).

Next, oligonucleotide-directed mutagenesis was employed to produce chimeric molecules containing individual amino acid substitutions within extracellular domain 3. These were transfected above and the transfectant cells are tested for susceptibility to infection by E-MuLV as shown above.

The results of the above studies show that the human H13 molecule acquires ability to bind to E-MuLV by substituting the native amino acid sequence with between 1 and 4 amino acids from corresponding positions in the murine ERR protein.

EXAMPLE VIII

Figure 18:
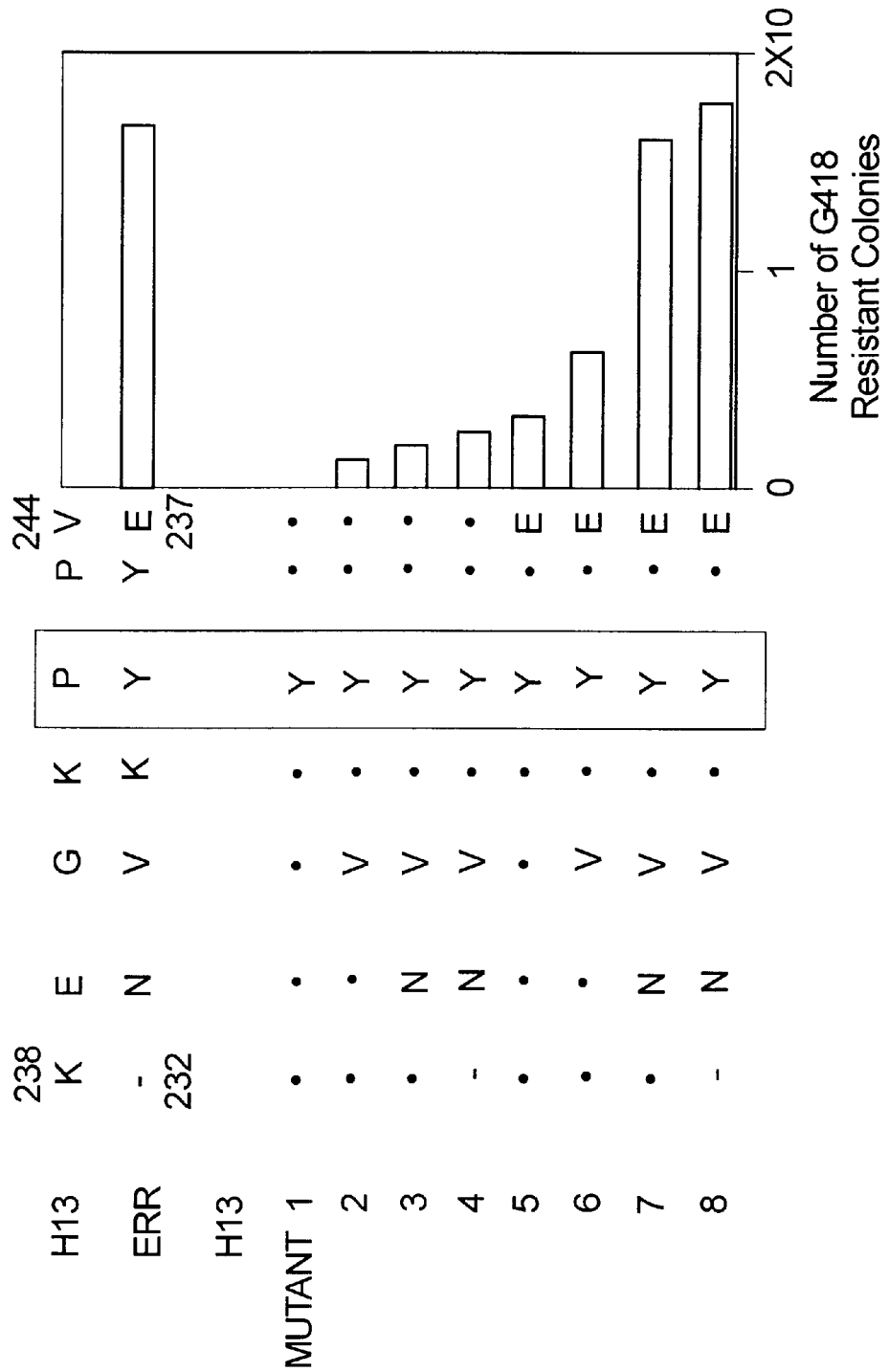
FIG. 18 shows results demonstrating the acquirement of ability of H13 function as a receptor for MuLV-E by mutation.

CVR Polypeptides as H13 Derivatives Capable of Providing Infectivity of Ecotropic Murine Leukemic Retrovirus Human H13 amino acid residues were substituted by murine ERR residues, as described in FIG. 18. Mouse-human chimeric receptor molecules were made by substitution using common restriction sites which clarified that the extracellular domains 3 and/or 4 contain the critical amino acid residues. Oligonucleotide-directed mutagenesis was then used to create 13 individual mutant ERR molecules containing one or two amino acids substitutions or insertions within these two extracellular domains. Substitution of at minimum two amino acids, Pro and Val, at the 242 and 244 amino acid residues in human H13 by the corresponding amino acid residues, Tyr and Glu, or substitution of Gly240 and Pro242 in human H13 with Val and Tyr, which correspond to Val233 and Tyr235 of ERR, such that the resulting mutant H13 has the ability to function as a murine ecotropic retroviral receptor. This mutant H13 will be useful in a gene therapy.

Figure 16:
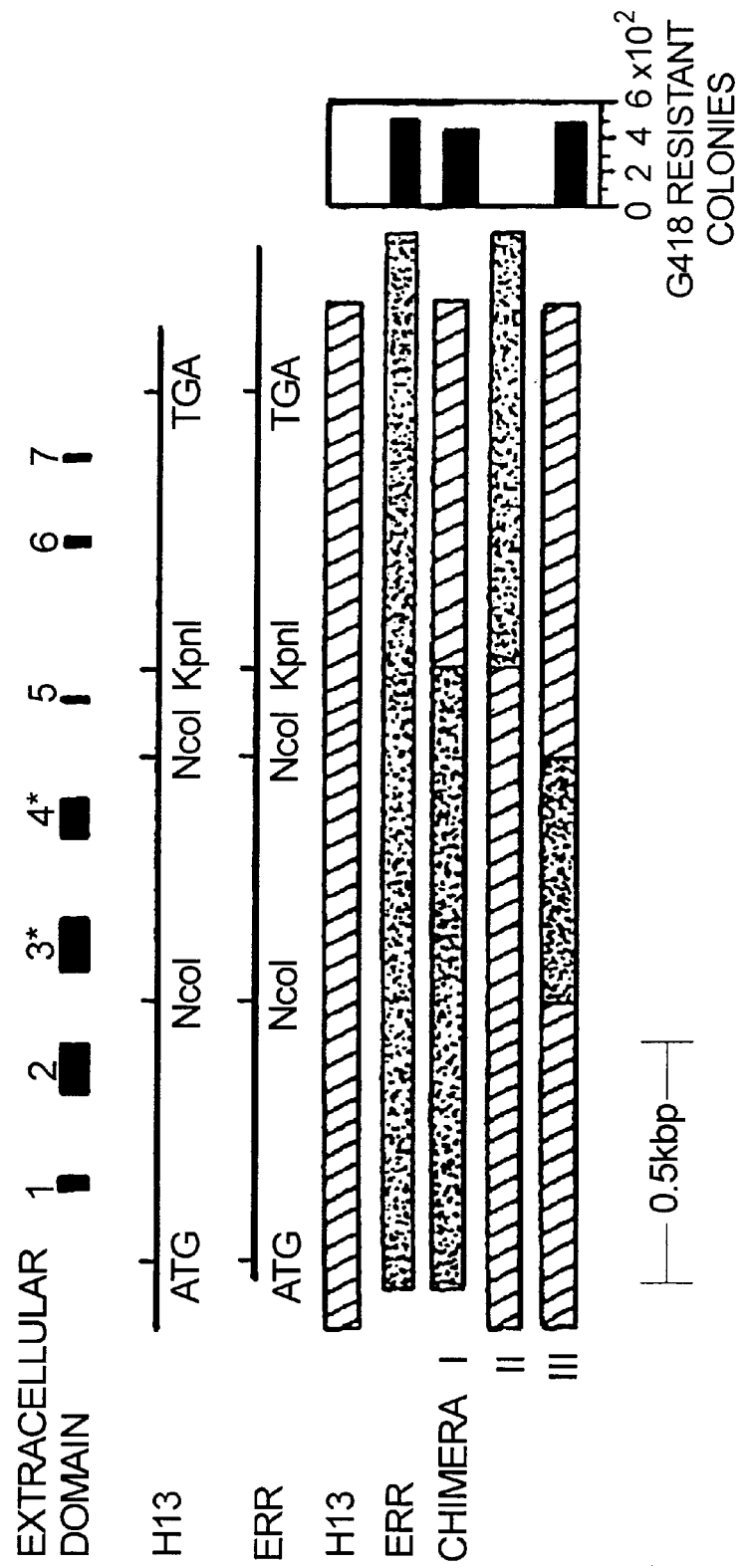
FIG. 16 shows a schematic illustration of extracellular domains 3 and 4, wherein (*) marks positions which contain important amino acids for infection by MuLV-E. Mouse-human chimeric receptor molecules (Chimera I-Ill) were prepared by substitution using common restriction sites in murine ERR and human H13, and their abilities to function as a receptor for MuLV-E was determined using the recombinant MuLV-E, ΨCRE/BAG virions (see, e.g., Price et al. *Proc. Natl. Acad. Sci. USA* 84: 154–160 (1987); Danos et al. *Proc. Natl. Acad. Sci. USA* 15: 6460–6464 (1988)). Black boxes on top of the figure indicate extracellular domains of ERR and H13 (see, e.g., Albritton et al. *Cell* 57: 659–666 (1989); Yoshimoto et al *Virology* 185: 10–17 (1991)), and shaded and striped bars indicate the nucleotide sequences of ERR and H13, respectively.

To compare the relative abilities of murine ERR and human H13 to function as a receptor for MuLV-E, Chinese hamster ovary (CHO-K1) cell lines were transiently transfected with a vector expressing either murine ERR or human H13 (see legend in FIG. 16). Two days later, these transfectants were infected with the recombinant MuLV-E, ψCRE/BAG virions, containing the *Escherichia coli* lacZ β1-galactosidase and Tn5 neo resistant genes (Price et al. *Proc. Nat'l. Acad. Sci. USA* 84:156–160 (1987); Danos et al. *Proc. Nat'l Acad. Sci. USA* 85:6460–6464 (1988)) and selected by G418. After 10–14 d numbers of G418-resistant colonies were counted (FIG. 16). No positive colonies were obtained with H13 transfectants while more than $10^3$ colonies were obtained with ERR transfectants. This indicates that H13 molecule without modification by substitution or deletion of amino acids lacks the ability to function as a receptor for MuLV-E.

To identify amino acid residues, modifications, as presented in FIG. 18, for MuLV-E infection, H13 modified proteins were prepared by substitution using the common and single restriction site, KpnI, and determined their abilities to function as a receptor for MuLV-E (FIG. 16). Approximately $10^3$ colonies were obtained with transfectants of Chimera I, whose first part is substituted by the corresponding region of ERR, while no colonies were obtained with transfectants of Chimera II, whose last part is substituted by the corresponding region of ERR. This indicates that the critical amino acid residues are located in the first part. To more narrowly define the essential region; Chimera III, whose NcoI-NcoI fragment is substituted by corresponding region of ERR, was made and its ability to function as the receptor was determined (FIG. 16). Approximately $10^3$ colonies were obtained, indicating that the critical region for the infection is located within the NcoI-NcoI restriction sites.

FIG. 17 shows the comparison of sequences of extracellular domains 3 and 4 in murine ERR and human H13, which are aligned using the Genetics computer group sequence analysis software package (Devereaux et al *Nucleic Acid Res*. 12:387–395 (1984)). Extracellular domain 3 is the most diverse region between murine ERR molecules (Mutants 1–11) containing one or two amino acid substitutions or insertions within these two domains (FIG. 17 and Table 2). For each substitution, amino acid residues of ERR were replaced with those found in equivalent position of H13 sequence. For each insertion amino acid residues of H13 were added into equivalent position of ERR sequence which aligned as shown in FIG. 17.

CHO-K1 cells expressing the mutant ERR proteins were tested for their abilities to function as a receptor for MULV-E. Surprisingly, no colonies were obtained with only Mutant 7 while approximately 500 colonies were obtained with the other mutants, indicating that of these 11 mutants only Mutant 7 abrogates the ability to function as the receptor (Table 2). Mutant 7 has two amino acid substitutions, Tyr (235 amino acid residue in ERR) to Pro (corresponding to amino acid residue 242 in H13) and Glu (corresponding to amino acid residue 244 in ERR) to Val (244 amino acid residue in H13). Therefore, Mutants 7A and B, which contain just one amino acid substitution (Mutant 7A: Tyr to Pro and Mutant 7B: Glu to Val), were prepared and tested for their abilities to function as the receptor. Although Mutant 7H has almost the same ability to function as the receptor as the intact ERR, Mutant 7A was found to almost completely abrogate the ability (Table 2). These results suggest that the Tyr located at 235 amino acid residue in ERR sequence is very important to function as a receptor protein for MuLV-E and substitution of this amino acid residue leads ERR to lose its ability to function as the receptor.

To determine whether the H13 molecule would acquire the ability to function as the receptor if certain amino acid residues in the H13 are substituted by the corresponding amino acid residues in ERR, eight mutants of H13 were made as shown in FIG. 18, and their abilities to function as the receptor were determined. The H13 mutants were created by the method of altered site-directed mutagenesis using a phagemid vector, pSELECT-1 (Promega), e.g., as presented in Lewis and Thompson, *Nucleic Acids Res.* 18:3439–3443 (1990). The mutagenesis is based on the use of single stranded DNA and two primers, one mutagenic and a second correction primer which corrects a defect in the vector to ampicillin resistance.

The insert of pSG5H13 was completely digested with BamHI and partially with EcoRI, and subcloned into the BamHI-EcoRI site of pSELECT-1 to obtain pSELECT-1 anti-sense H13. The insert of PSG5H13 Mutants 5 and e were excised with EcoRI and subcloned into the EcoRI site of pSELECT-1 to obtain pSELECT-1 antisense H13 Mutants 5 and 8. H13 mutants 1–3 and 5 were prepared using the pSELECT-1 antisense H13 as a template and oligonucleotides: AAAGAAGGGAAGTACGGRGRRGGRGG (SEQ ID NO:9) (H13 Mutant 1); ACACAAAAGAAGTGAAG-TACGGTGTTGGTGG (SEQ ID NO:10) (H13 Mutant 2); ATGACACAAAAAACGTGAAGTACGGTGTTGGTGG (SEQ ID NO:11) (H13 Mutant 3); and AAAGAAGG-GAAGTACGGTGAGGGTGGATTCATG (SEQ ID NO:12) (H13 Mutant 5). H13 Mutant 4 was prepared using pSELECT-1 antisense H13 Mutant 8 and oligonucleotide TGAAGTACGGTGTTGGTgGATTCATG (SEQ ID NO:13). H13 Mutants 6–8 were prepared using pSELECT-1 antisense H13 Mutant 5 and oligonucleotides ACACAAAA-GAAGTGAAGTACGGTGA (SEQ ID NO:14) (H13 Mutant 6); AATGACACAAAAAACGTGAAGTACG-GTGA (SEQ ID NO:15) (H13 Mutant 7); and AACAAT-GACACAAACGTGAAGTACGGTGAGGGTG-GATTCATG (SEQ ID NO:16) (H13 Mutant 8).

The ERR mutants were also created by the method of altered site-directed mutagenesis using a phagemid vector, pSELECT-1 (Promega), e.g., as presented in Lewis and Thompson, *Nucleic Acids Res.* 18:3439–3443 (1990). The mutagenesis is based on the use of single stranded DNA and two primers, one mutagenic and a second correction primer which corrects a defect in the vector to ampicillin resistance.

The insert of pSG5ERR was partially digested with BamHI and EcoRI, and subcloned to the BamHI and EcoRI sites in pSELECT-1 to obtain pSELECT-1 sense and antisense ERR. Single stranded DNA was prepared from pSELECT-1 sense (for preparation of Mutants 2 and 6) and antisense (for preparation of the other mutants) ERR and mutagenesis was carried out according to the manufacturer's directions (Promega). The correctly mutated clones were selected by directly sequencing using Sequenase (USB) and two ERR specific antisense oligonucleotides GGTGGCGT-GCAGTCAA (SEQ ID NO:17) for mutants 1–7 and TCAGCCATGGCATAGATA (SEQ ID NO:18) for Mutants 8–11) as primers. Mutated :inserts of the phagemids prepared by mini-preps were excised with EcoRI and subcloned into the EcoRI site of pSG5. The presence of mutations was confirmed by sequencing each plasmid using the same primers as used above. Each mutant was then transiently transfected into CHO-K1 cells by the method using Lipofectin reagent and their susceptibilities to infection by MuLV-E were determined as above for results shown in FIG. 16.

Accordingly, it was shown that mutant H13 polypeptides according to the present invention containing Tyr242 and at least one of Val 240 and Glu244 provide a mutant H13 receptor binding region that is functionally recognized by ecotropic murine retroviruses, such as, but not limited to, MuLV-E, such that expression of such a CVR polypeptide on the extracellular surface of a human cells allows binding and infection by a murine ecotropic retrovirus. Such a method can thus be used according to the present invention as a method for gene therapy in vitro, in vitro or in situ. Alternatively, such a method of the present invention can be used to introduce heterologous or exogenous genes into human cells or tissues using a murine ecotropic retroviral vector. Thus, the use of an H13 mutant according to the present invention provides a much safer means for gene therapy than the use of amphotropic retroviral vectors, which overcomes the problems of unintended infection of non-target cells by amphotropic retroviruses, as well as immunogenicity reduction for the use of relatively lower dosages of recombinant ecotropic virus.

In summary, the cloning of the human ecotropic retrovirus receptor and the realization that murine ecotropic viruses cannot normally infect human cells, excepting for the introduction of a molecular modification, sets the state for improving dramatically the safety of gene therapy involving retroviruses. In the first step the modified gene for the ecotropic: retroviral receptor will be delivered to target cells and expressed on the cell surface. The murine ecotropic-virus-vector would then be used to infect, stably integrate, direct the expression of the desired therapeutic gene. Zero to some time may elapse between the first step of the infection.

The ecotropic virus vector to be used will carry deletions of the structural genes and be propagated in "safe" packaging cell lines for added safety. The construction of novel packaging lines producing virus titers in the $10^8$ to $10^{10}$ particles/ml range is expected and devoid of recombinant viruses capable of infecting human cells. Furthermore, modification of the viral envelope glycoprotein will eliminate any determinants which would interfere with virus infectivity in vivo or diminish virus titers. The human ecotropic virus receptor homolog also is studied to determine its normal gene function and gain sufficient understanding of the protein to eliminate the likelihood that gene therapy protocols would affect its normal function in a deleterious manner.

EXAMPLE IX

Cloning of a Human Amphotropic Virus Receptor

The amphotropic receptor is cloned for development of gene therapy vectors. The receptor for amphotropic-MLV are cloned by a similar strategy to that used to clone the receptors for Gibbon ape leukemia virus and mouse ecotropic virus (E-MLV) according to known method steps (e.g., Brown et al, 1990; Anderson et al, 1991). The strategy relies on the fact that human cells can be infected by A-MLV but hamster cells cannot. The inability to infect hamster cells result from their lack of a suitable receptor, making possible the transection the human gene into hamster cells, rendering them infectable by A-MLV. Isolating these cells by infection with antibiotic-resistant recombinant viruses followed by selection of antibiotic containing media is then performed. The receptor gene is accessible to cloning by virtue of its association with human repetitive DNA. When the amphotropic receptor gene is cloned, its similarities and dissimilarities to the ecotropic virus receptor is studied in a variety of assays and by a variety of techniques (e.g., Yoshimoto et al, 1993).

Methods CHO cells are plated on the morning of transection. Sheared human genomic DNA (50 μg) and $pSV_{2gpt}$ DNA (1 μg) are coprecipitated with calcium phosphate by the method of Wigler et al. (1978) and applied to CHO cells. The next day, transfected cells are passaged at $2 \times 10^3$ cells per plate in gpt selection medium (DMEM/10% FCS, hypoxanthine 15 μg, xanthine μg/ml, thymidine 10 μg/ml, glycine 10 μg/ml, methotrexate 0.1 μM, and mycophenolic acid 25 μg/ml). After 21 days under selection, colonies are dispersed by brief exposure to trypsin/EDTA and replaced prior to exposure to viruses, allowing for enrichment of cells that have acquired human DNA.

PA317/LNL6 amphotropic retrovirue producer fibroblasts are grown to confluence and refed with fresh medium. Twelve to twenty hours later, the culture medium is filtered (0.45 gm, Nalge), brought to 8 μg/ml of polybrene, and incubated with the transfected CHO cells. After 4–12 hours fresh medium is added, and the infection protocol repeated the next day. Three days later, these cells are replated at $2 \times 10^3$ cells per 82 mm plate in DMEM/I0% FCS containing 1 mg/ml of G418, and selection medium is replaced every 3 days for 15 days. It is expected that out of 20,000 transfectants, only a few (10–20) will develop into g418 resistant colonies. To authenticate that clones are infectable by this amphotropic virus indeed express the amphotropic virus receptor, they are also infected by a second amphotropic virus (ψ-2-AM-ZIP-DHFR). It is possible for cells to acquire the virus through a low efficiency pathway not involving the virus receptor. G418-resistant colonies are isolated with cell cloning cylinders and each is exposed to ψ-2-AM-ZIP-DHFR virus as described above for the neomycin virus. Following exposure to the virus, cells are selected in DMEM/10% dialyzed FCS containing methotrexate (150 nM). After 14 days, plates are stained for the presence of methotrexate-resistant colonies with 1% crystal violet.

DNA is then prepared from this primary transfected cell line (1° TF) and used in a second cycle of the transection/ infection protocol. To identify the receptor gene is the secondary transfectant cell lines, Southern blots using a panel of human repetitive sequences as probes are made. Because of the low efficiency of DNA transection (0.1% genome/cycle), cycles of transection/selection are adequate to segregate the receptor gene away from the remainder of the murine genome (Murray et al., 1981). To isolate the desired fragment, a lambda phage library is prepared from secondary transfectants DNA and hybridized with the radio-labeled repetitive probe that seems most appropriate from the Southern blot screening. To identify molecular clones that contain the protein encoding portion of an amphotropic receptor gene, RNA transcript present in the 2° TFs growing the amphotropic viruses are identified. The specific transfer of the gene in question is expected to transfer susceptibility to amphotropic virus infection in a consistent manner.

EXAMPLE X

Expression of Therapeutic Delivery Vector According to the Present Invention

A complementary DNA (cDNA) from the antibody B3 (e.g., Brinkmann et al, 1991) is used to construct an Fv fragment that is fused to a CVR polypeptide of the present invention. This single-chain recombinant receptor, then is used to allow retrovirus infection of targeted human cells. Antibody to B3, which binds to a carbohydrate antigen expressed on the surface of many, carcinomas, has been used to make a single-chain recombinant toxin that causes the complete regression of human tumors in mice (Brinkmann et al, 1991). A single-chain Fv and two different (B3 (Fv) immunotoxins, B3 (Fv)-PE40 and B3 (Fv) PE38KDEL vectors are used via standard recombinant DNA technologies to insert into the CVR polypeptide encoding nucleic acid, or substitute its recombinant toxin with the virus binding domain of the gene encoding the modified region of the human ecotropic virus receptor. The resulting plasmid (B3 (Fv)-mH13) as well as the immunotoxin vector B3 (Fv)PE38KDEL are expressed in a host, such as, but not limited to, *E. coli*, and the single chain immunoreceptor and single-chain immunotoxin are purified to homogeneity as known in the art.

The antitumor activity of the B3 (Fv)-mH13 is determined first in vitro. The B3 antibody reacts uniformly with the surface of many mucinous carcinomas of the colon, stomach, and ovary and with normal tissues, such as, but not limited to, glands of the stomach, epithelia of the trachea and bladder, differentiated epithelium of the esophagus, and small bowel mucin. (Pastan et al. (*Cancer Res.*, 51:3781–3787, 1991)). The B3 antibody also reacts uniformly with many human tumor cell lines, including MCF7, MDA-MB-468, and HTB20 (breast), A431 (epidermoid), TH29 (colon), HTB33 (cervical), and DU145 (prostrate). Infection in some or all of these cells is expected, such as, but not limited to, A431, of a non-human specific recombinant retroviral vector, such as, but not limited to, a murine ecotropic retrovirus vector carrying the neomycin resistant gene, after first delivering to those cells the modified receptor peptide by use of the fusion protein derived from B3 (Fv)-mH13. The viral vector having an env binding domain which binds the CVR polypeptides and a therapeutic agent, such as, but not limited to, a murine ecotropic retrovirus vector carrying the thymidine kinase gene, is used preliminarily to cause cell death of cultured tumor cells, such as, but not limited to, A431 cells, by the addition of ganciclovir to the cell cultures.

When such cell is shown to work in culture, then pathological cell killing in animal model systems is used, such as a rabbit model or a rat model. Thus, murine ecotropic virus based vectors of the present invention are expected to be incapable of infecting these cells, unless a CVR polypeptide or the corresponding region of the murine ecotropic virus receptor is expressed on the selected animal model cell surface via the delivery vector presented herein. At various intervals after the fusion protein injection, a viral vector (including time 0, i.e., simultaneously with the fusion protein) carrying the thymidine kinase gene is used to infect the animal models expressing the CVR polypeptide on the selected target cells. This expression is followed by the administration of ganciclovir to the animals. This protocol is expected to achieve tumor reduction as the ganciclovir is phosphorylated within tumor cells to its toxic form and in conjunction with the associated "bystander effect".

EXAMPLE XI

Construction of a Vector for the Expression of the Fusion Protein of a CVR Polypeptide and a Single-chain Antigen-binding Protein Recognizing Tumor or Pathologic Cells or Tissues An example of a suitable methodology for constructing a fusion protein is illustrated in FIG. 4. The expression plasmid pUL1 contains the gene for the immunotoxin B3 (Fv)-PE40, which is a fusion protein including an antibody fragment to an antibody to B3 specific of carcinoma cells, conjugated to the toxin PE40. The pUL1 expression plasmid is modified to replace the PE40 toxin encoding portion with a CVR polypeptide of the present invention or the corresponding region of the murine ecotropic virus receptor to provide a delivery vector that transforms carcinoma cells in vivo, in situ or in vitro, to express a CUR polypeptide. This could also be replaced with an $F_v$ to the envelope of the virus to follow.

B3 (Fv) is a single chain antigen-binding protein derived from a monoclonal antibody to B3. The B3 antibody fragment recognizes a carbohydrate antigen which is found on the surface of many mucinous carcinomas. However, the antibody fragment reacts with only a limited number of normal tissues, such that the antibody fragment will preferentially bind carcinoma cells in vivo. PE40 is a truncated derivative of Pseudomonas exotoxin. The PE40 coding region has a Hind III restriction site at the 5' end, the point of connection to the DNA encoding B3 (Fv), and an EcoRI site just beyond 3' end. This Hind III-EcoRI fragment encoding PE40 is removed from pUL1 and both termini of the linearized pUL1 are partially filled-in with dATP, yielding cohesive ends -AA. The -TTCGA at 3' end of B3 (Fv) coding region and AATTC- at the other terminus of the linearized plasmid are similarly modified to complement the CVR polypeptide encoding DNA, as follows.

Nru 1-Pst 1 fragment of a CVR polypeptide the present invention, as a modified H13 cDNA, which contains whole coding region of modified H13, is digested with Tfi I and the 850 by fragment, which contains the region encoding the third extracellular domain of the modified H13, is purified on a 1.5% agarose gel. The purified 850 by Tfi 1 fragment is then digested with BsrI and 85 by Bsr 1-Tfi 1 fragment, which encodes the whole third extracellular domain of the modified H13 designated Ex3mH13. The resulting restriction fragment EX3m13 is purified on 2.0% agarose gel. The purified 85 by Bsr 1-Tfi 1 fragment has cohesive ends AGC- at 5' end and -GG at 3' end.

CGTCG- -CCTAA

This 3' end is partially filled-in with dATP, making the 3' end

-CCTAA.

-GGA.

After partial filling-in, the 85 by Bsr 1-Tfi fragment is be ligated to the partially filled-in Hind III-EcoRI site of the linearized pUL1 using adapters CGCTTTCAACTGGC (SEQ ID NO:19)

AAGTTGAC and TTCTAATTAG (SEQ ID NO:20)

GATTAATCTT (as 3'-5'TTCTAATTAG (SEQ ID NO:21)), which are specially designed to prevent any frame shift. The resulting plasmid is designated pBH30.

The gene encoding B3 (Fr) has a Ndel site at 5' end. The resulting plasmid pBH30 is then digested with Ndel and the termini are filled in with dATP and dTTP to become blunt ends. Then, the linearized and filed-up plasmid is digested with EcoRI and the fragment containing B3 (Fv)-Ex3mHl3 coding region is purified on an agarose gel.

The purified fragment is integrated into an expression vector pTrcHisB at the BglII-EcoRI site, which is positioned downstream of the series of a Trc promoter, an ATG initiation codon, a polyhistidine coding region and an enterokinase-cleavable site coding region, using an adaptor

GATCCCCGGG (SEQ ID NO:22)

GGGCCC so that any frameshift should be prevented.

The resulting plasmid is designated pBH3

Expression and purification of B3 (Fv)-Ex3mH13 fusion protein.

The expression plasmid pBH3 allows B3 (Fv)-Ex3MH13 to be expressed as a fusion protein composed of a polyhistidine metal binding domain, an enterokinase-cleavable site and B3 (Fv)-Ex3mH13.

*E. coli* HB101 is then transformed with pDH3. The expression is induced with isopropyl β-d-thiogalactoside and the cells are harvested and resuspended in a buffer solution. The suspension is sonicated and the supernatant is loaded on a $Ni^{2+}$metal affinity resin column. The protein bound to the resin is eluted by competition with glycine.

The eluted protein is then treated with enterokinase for the polyhistidine sequence to be removed.

The resulting fusion protein is expected to specifically bind the pathologic cells described and is suitable for providing a chimeric cell as a target for therapy as described herein.

EXAMPLE XII

Increasing the Efficiency of In Vivo Virus Replication Through Definition of Critical Regions of the Viral Envelope Which Binds to a Receptor Equally important to the goal of developing improved vectors is understanding the critical regions of the viral envelope which binds to the receptor. Engineering of new vectors is dramatically improved according to the present invention and their in vivo titers effectively increased. Consequently, the present invention provides for the dissection of viral envelope elements required for binding to both receptors' as well as the characterization of the degree of modification that these proteins will tolerate without abrogating their capacity to bind the receptors, as well as to examine how the limited differences between the human and mouse ecotropic receptors responsible for allowing binding of the virus. A second aim is to eliminate any potential complement binding region on the viral envelope which might lead to virus lysis in humans, a problem which has been argued by some investigators to probably limit the infectious potential in vivo of therapeutic vectors based on murine retroviruses.

The finding of nonspecific inactivation and lysis of murine, feline, and simian C-type viruses was originally published by Welsh et al. (1975, 1976). The lysis is due to antibody-independent binding of the human Clq complement component to p156, leading to the activation of the classic complement pathway (Cooper et al., 1976). It is believed that Clq recognizes p156 because the p156 molecules have a domain resembling the C1q recognition site on the Fc fragment of immunoglobulin. It was suggested (Welsh et al., 1975; Cooper et al., 1976) that the nonspecific lysis of retroviruses by human complements is an adaptive defense system that may protect against viremia and cause the lysis of cells expressing p156 on the surface. However, preliminary findings suggest that complement-deficient patients do not exhibit elevated levels of cross-reacting antibodies to primate retroviruses, indicating no greater susceptibility to retrovirus infection in these patients (Kurth et al., 1979b). Further, Gallagher et al. (1978) have shown a similar lytic activity of gibbon ape sera for retroviral envelopes, yet some of the same gibbons were infected with GALV and synthesized anti-GALV antibodies. The protective effect of the complement-dependent lysis of retrovirus, therefore, remains controversial.

Sequence of the murine ecotropic viral envelope which binds to the virus receptor.

One way of defining the binding parameters of Murine leukemia virus (MuLV) surface glycoprotein ($gp70^{SU}$) is to determine which regions of $gp70^{SU}$ participate in the specific interactions with cell surface receptors. A variety of studies have suggested that the determinants for receptor specificity lie in the N-terminal two thirds of $gp70^{SU}$ (Ott and Rein J. Virol 66:4632–1638, 1992). In fact, Heard and Danos 1991) have recently shown than an env fragment containing most of this region of Friend MULV $gp70^{SU}$ can bind to the ecotropic receptor in NIH 3T3 cells. Recently Ott and Rein have attempted to map receptor specificity in $gp70^{SU}$ by constructing a series of chimeric env genes, using Moloney MCF (Mo-MCF), 10A1, and amphotropic $gp70^{SU}$ sequences. The analysis of MgLVs containing these chimeric $gp70^{SU}$ gave both simple and complex results. In some cases, receptor specificity could be mapped to a single region of $gp70^{SU}$. Finally, some combinations seemed to be capable of fully functional interactions with one receptor but also a partial or abortive interaction with one or two receptors.

Heard and Danos (*J. Virol.* 65:4026–4032, 1991) have shown, using an interference assay, that the gp70 amino-terminal domain folds into a structure which recognizes the ecotropic receptor regardless of the carboxy-terminal part of the molecule. They have argued that it may be difficult to interpret the functional consequences of structural modifications, introduced in envelope glycoprotein by using virus entry assays. On the other hand, in cells constitutively expressing envelope glycoproteins, the interference phenomenon results from envelope-receptor interactions alone. Therefore, the delineation of cell resistance to further entry of virus particles that bind the same receptor provides a functional receptor binding assay.

Experimentation

Interference assays are used to more precisely define the region of the murine ecotropic envelope glycoprotein (MuLVE-gp70) which is critical for binding to its receptor. To establish more precisely the structural requirements for binding to the ecotropic receptor the MuLVE-gp70 is modified by in-frame deletions within the amino-terminal domain, and by oligonucleotide directed mutagenesis. A comparison of envelope sequences shows that MLVgp70s differ in two limited regions in their amino-terminal domains. These are amino acids 50 to 116 and 170 to 183. They also differ in the proline-rich segment, amino acids 244 to 283. By analogy with the avian sarcoma and leukemia virus envelope glycoproteins, in which determinants for receptor interactions have been ascribed to short hypervariable sequences (Heard and Danos *J. Virol.* 65:4026–4032, 1991;), one or more of these three hypervariable regions are expected to include receptor binding cells. Defective retroviral vector transducing a modified *E. coli* lacZ gene is used to infect cells expressing wild-type or modified MuLVE-gp70s. Susceptibilities to infection are determined by counting X-Gal-positive foci.

The ecotropic envelope N-terminal domain vectors is transiently transfected into simian Cos-7 cells that express the exogenous murine ecotropic retroviral receptor gene (Albritton et al, 1989). Since the pSG5 vector utilizes the early SV40 eukaryotic promoter, the Cos cells (expressing to T antigen gene) permits a high level of env gene expression (Gluzman, 1981). Transfected cells are infected with the ecotropic pseudotype ψ CRE/BAG (ATCC CRL 1850) virions (Price et al, 1987) and the number of β-galactosidase (gal) foci are assayed. Modified env fragments which decrease the number of β-gal foci are further examined for their ability to interact with the ERR.

Transection of the ERR Gene into Cos-7 Cells.

The ERR gene was cloned into the pcDNA/neo expression vector (Invitrogen) and transfected into Cos-7 cells by the CaPO4 method (Stratagene). Cos-7 cells have been shown to be capable of producing high-titers of MuLV retroviruses (Landau and Littman, 1993). Transfected cells are selected for neomycin resistance to 500 µg/ml G418. Resistant clones are tested for their ability to be infected by ψ CRE/BAG virions (Price et al, 1987). Cells are fixed with 0.5% glutaraldehyde in physiological buffered saline and stained with a histochemical solution containing 1 mg/ml X-gal (Sanes et al, 1986). Those cells having the highest number of β-gal foci are used for interference assays.

Construction of modified env genes to further delineate receptor binding sequences. This experiment determines the smallest N-terminal fragment that will block ecotropic virus infection. The gp70 gene from the Akv endogenous murine leukemia virus is used in these studies; the Akv genome is capable of producing active virions and the env sequence has been determined (Lenz et al, 1982).

The entire gp70 gene, contained between AccI and XbaI restriction sites is cloned into the psG5 eukaryotic expression vector (Stratagene). Fragments of the env gene are also cloned to produce the following N-terminal peptides: AccI/AluI 247 aa fragment produces the results of Heard and Danos (1991) and functionally block infection. Of particular interest is the 122aa Acc 1/Sma 1 fragment which contains the region thought to determine receptor binding specificity (Battini et al, 1992).

Interference assays of modified env gene constructs. Recombinant env gene constructs are transiently transfected into Cos-7 cells containing the murine ERR. This system is expected to eliminate any potential problems caused by endogenous env transcripts that might be present in murine cells. Cos cells are expected to permit high expression of the SV40 promoter-containing expression plasmids (Gluzman, 1981). The cells are transfected by the DEAE dextran method according to Stratagene protocols. Approximately 48 hrs after env gene transection, $2 \times 10^5$ cells are plated onto a six-well culture dish and infected with $10^2$–$10^3$ ψCRE/BAG virions in the presence of Bug polybrene/ml according to the method of Heard and Danos (1991). When the cells have grown to confluence, they are fixed in 0.5% glutaraldehyde in PBS and stained with a histochemical solution containing 1 mg/ml X-gal (Sanes et al, 1986). The number of β-gal foci are scored relative to cells which were transfected with the pSG5 vector alone. A decreased number of β-gal foci are expected to be scored relative to cells which were transfected with the pSG5 vector alone. A decreased number of β-gal foci determines that the transfected env construct is likely to be able to bind the ERR and block virion interaction.

Analysis of modified-env biosynthesis in transfected cells. To determine whether recombinant env gene products are produced by the transfected cells, protein analysis is performed. Cells are metabolically labeled with a mixture of $^{35}$S methionine and $^{35}$S cysteine (ICN), since the env protein is relatively rich in cysteine residues in the regions of interest. After labelling for 30–60 minutes, cells are pelleted and both the pellets and supernatant are processed for immunoprecipitation with polyclonal goat anti-Rauscher gp70 antibody (NUIH repository) or non-murine sera followed by *S. aureaus* A cells. Process immunoprecipitates are analyzed on SDS-polyacrylamide gels. The absence of immunoprecipitated protein is expected to signify that the env protein is degraded or unable to be recognized by the anti-gp70 antibody in this event, the presence of env RNA transcripts is determined by extracting total RNA from the transfected cells followed by northern blot analysis using an Akv env sequence probe.

Fragments which are able to be detected by immunoprecipitation and which block ψ CRE/BAG virion infection are utilized in further examples and methods of the present invention.

Figure 19:
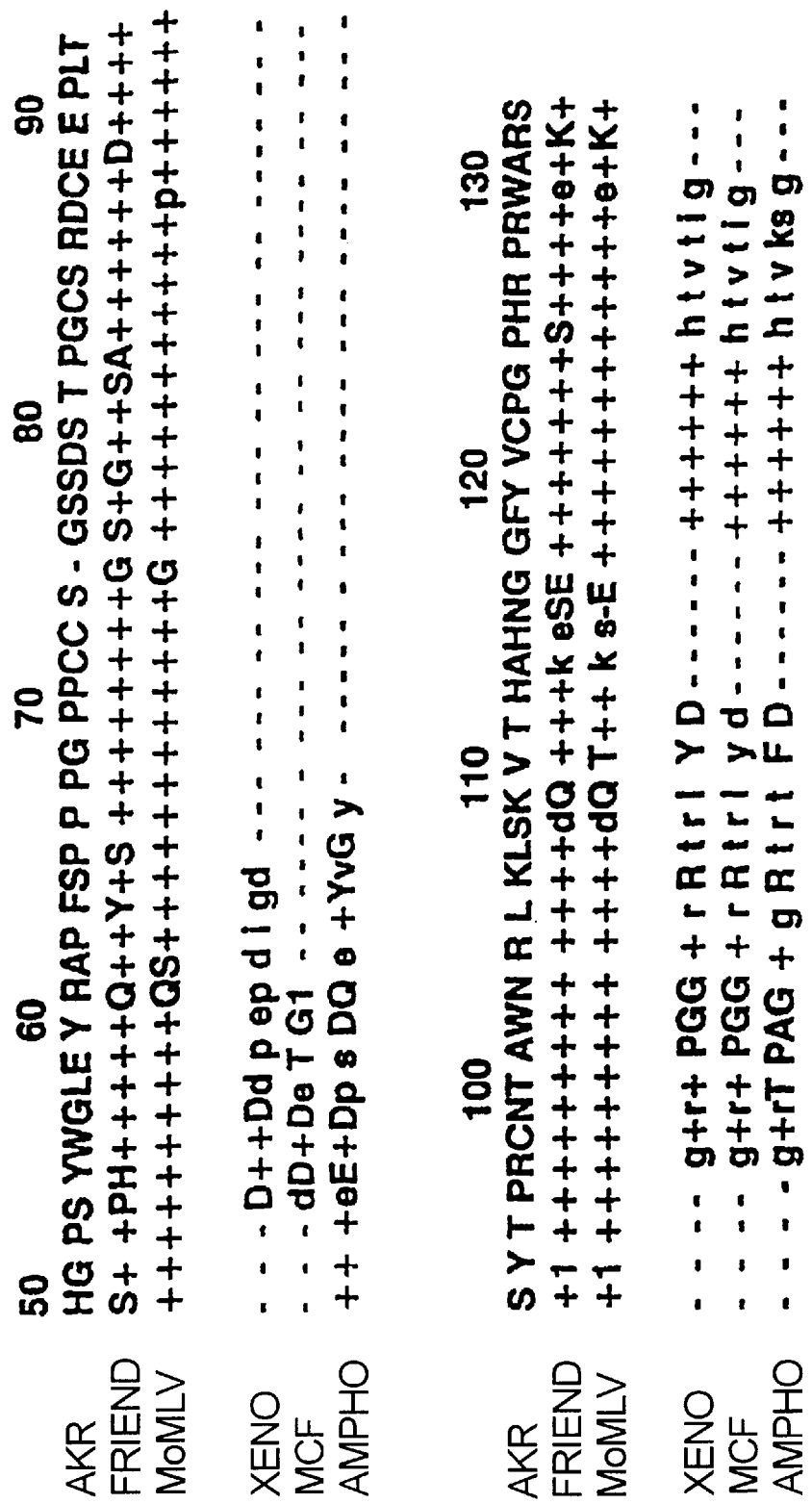
FIG. 19 shows the alignment of gp70 amino acid sequences associated with receptor specificity with leukemia virus sequences. Ecotropic retrovirus sequences: AKv(8); Friend MLV (11); Moloney MLV (12). Non-ecotropic retrovirus sequences: xenotropic MLV NZB.1U.6(2); polytropic MCF 247 (2); amphotropic MLV 4070A(2); (+)–amino acid identity; (−)—gap in sequence; Caps—conserved amino acid substitution lower case—non-conserved amino acid substitutions. Number indicate the position of amino acids in the gp70 sequence.

Mutation of modified env fragments. The DNA sequences of several ecotropic and non-ecotropic retrovirus gp70 genes have been determined. Comparison of these sequences will suggest regions which are important for receptor interaction. For example, FIG. 19, shows a comparison of 3 ecotropic and non-ecotropic gp70 amino acid sequences, within the N-terminal region, thought to be involved in receptor specificity. The three ecotropic retroviruses show strong sequence homology. There are considerable differences between the ecotropic and non-ecotropic sequences, the most salient being a gap of approximately 30 amino acids located at positions 68 to 97 (Battini et al, 1992). While this region may contain an ecotropic binding site, it is also likely to confer different conformations upon the different subgroups of retroviruses. This is a region of the env which might be suitably modified by the introduction of sequences that will help target the virus to specific uses.

When limited regions of the N-terminal env protein are found to block viral-receptor interactions, then it is possible to systematically modify amino acids in order to identify critical residues. In vitro mutagenesis is then accomplished utilizing mutagenic oligonucleotides and the pSelected (pAlter) system of Promega as previously described for the modification of ERR (Yoshimoto et al, 1993).

If it is not possible to limit the location of the receptor binding domain such that it is feasible to create point mutations, the creation of deleted molecules or chimeric molecules between limited gp70 regions of the different viral subgroups are provided.

a) Creation of deletion mutants criteria and protocol.

1. Digestion with an enzyme having sites within the region of interest and relatively few elsewhere in the recombinant plasmid.

2. If the reading frame is altered, use exonuclease III to progressively remove nucleotides.
3. Use S1 nuclease to create blunt ends (13). Ligate and transform the deleted molecules.
4. Determine the sequence of the deleted clones to find those which maintain the correct reading frame.

For example (FIG. 20), a 163 bp SmaI fragment is present (404 bp, 567 bp) within the variable region of the Akv env N-terminal sequence (Lenz et al, 1992). This fragment includes the 30 amino acids which are deleted from the amphotropic sequence (FIGS. 19 and 20). Simple removal of this sequence will create an incorrect reading frame since one SmaI site (404 bp) lacks 1 nucleotide of an amino acid triplet.

b) Creation of Insertions.

The insertion of a specific sequence is performed by using the polymerase chain reaction (PCR) to amplify the sequence of interest according to standard protocols (Sambrook, supra; Ausubel, supra). The PCR primers are designed to maintain the proper reading frame of the env protein.

For example, the insertion of the 30 amino acid region of the ecotropic virus into the amphotropic virus sequence is accomplished by the following steps.

1. Digestion of the amphotropic env sequence with Rsa1 at position 325 creates a blunt end site and separates the 1st nucleotide (T) from the 2nd and 3rd (A, C) of the amino acid colon for tyrosine.
2. In order to insert the ecotropic sequence, a primer is synthesized which contains an extra AC at the 5' end in order to retain the tyrosine residue. A 3' primer is synthesized with an extra T at its 5' end which adds a tyrosine residue and retains the reading frame. The position of the proposed primers on the Akv sequence are shown in Table III.

TABLE III

| | |
|---|---|
| 5' primer: 5' AC CCG GGG CCC CCC TGC 3' | (SEQ ID NO:23) |
| 3' primer: 5' A GGG AGT ATA ATG AAG 3' | (SEQ ID NO:24) |

Following PCR, the product is run on a 2% agarose gel, the 90 bp fragment is excised, purified and ligated to the amphotropic env sequence at the Rsal site. Recombinant clones are sequenced to determine those having the correct orientation of the PCR fragment.

Identification of viral envelope sequences binding C1q. It has been suggested that p15E molecules have a domain resembling the C1q recognition site on the Fc fragment of immunoglobulin. If this correct, and if this region is in an unnecessary part of the molecule for virus binding and entry, its removal and replacement is expected to alleviate any potential effects of serum oncornavirus lytic activity (SOLA) on the direct, in vivo use of retroviral vectors for gene therapy to identify amino acid residues critical for C1q binding, the MuLVE-p15E is modified by in-frame deletions when the domain resembling the C1q recognition site on the Fc fragment of immunoglobulin, and by oligonucleotide directed mutagenesis. Once the C1p recognition is identified, we will attempt to construct a modified MuLVE-p15E env gene, is Constructed which will have this region substituted by non-C1q binding sequence.

To assay for SOLA activity in serum, and virus sensitivity, sucrose banded and purified, cloned Radiation leukemia virus is diluted with PBS to a standardized concentration, so that at least 100,000 cpm are detectable in our standard reverse transcriptase assay (Brown et al; 1990). Human serum at various dilutions are added to the virus preparation and incubated for 30 minutes. Control samples are treated with 0.5% Triton X-100 (Sigma). All samples are then analyzed for RT activity as previously described (Meruelo et al, 1988).

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the contents of the references cited within the references cited herein are also entirely incorporated by reference.

Reference to known method steps, conventional methods steps, known methods or conventional methods is not in any way an admission that any aspect, description or embodiment of the present, invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the generic concept of the present invention. Therefore, such adaptations and modifications are intended to be comprehended within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein.

TABLE 2

Abolishment of ability of ERR to function as a receptor for MuLV-E by mutation.
ERR Oligonucleotide use for mutagenesis

| AA change | | Infectivity | Mutant (ERR) | (H13) |
|---|---|---|---|---|
| Extracellular domain 3 | | | | |
| A*<br>1 AAGGCTCCGTTAAAAAC | | (SEQ ID No: 19) I | V | +++ |
| T  T<br>2 TACAGGAGAAATCTTCCTCCGTGAGCTG**<br>TC --- | | (SEQ ID No: 20) KN | ED | +++ |

TABLE 2-continued

Abolishment of ability of ERR to function as a receptor for
MuLV-E by mutation.
ERR Oligonucleotide use for mutagenesis

| AA change | | Infectivity | Mutant (ERR) | (H13) |
|---|---|---|---|---|
| 3 | GAGAAAAATTTCGGCAACTGTAACAACAAC | (SEQ ID No: 21) S– | GN | +++ |
| 4 | AAAAATTTCTCCCGTCTCTGTAACAACAAC (------) | (SEQ ID No: 22) – – | RL | +++ |
| 5 | AATTTCTCCTGTTTCAACAACGACAC (AA) | (SEQ ID No: 23) N | L | +++ |
| 6 | TCACCGTATTTCCCTTCTGTGTCGTTGTT** (A G T) | (SEQ ID No: 24) NV | EG | +++ |
| 7 | ACAAACGTGAAACCCGGTGTGGGAGGGTTTAT (TA  A) | (SEQ ID No: 25) YGE | PGV | – |
| 7A | ACAAACGTGAAACCCGGTGAGGGAGG (TA) | (SEQ ID No: 26) Y | P | + |
| 7B | ATACGGTGTGGGAGGGT (A) | (SEQ ID No: 27) E | V | +++ |

Extracellular domain 4

| 8 | TCTGCCTGGACAACAACAGCCCGCTGC (T   G) | (SEQ ID No: 28) ID | NN | +++ |
| 9 | GCCCGCTGCCTGACGCCTTCAAGCAC (GT) | (SEQ ID No: 29) G | D | +++ |
| 10 | GCCTTCAAGCACGTGGGCTGGGAAGGAGCTAAGTACGC (CA      A) | (SEQ ID No: 30) QG EE | VGWEG | +++ |
| 11 | GCCTTCAAGCACGTGGGCTGGGAAGGAGCTAAGTACGC (CA      A) | (SEQ ID No: 31) E | G | +++ |

This is one of the representative result of three different experiments.
*Letters above each oligonucleotide sequence are those in the original ERR
sequence. "–" means the absence of corresponding nucleotide sequence in ERR
sequence according to the alignment (SEQ ID NO. 3)
**These two are antisense oligonucleotides and the others are sense oligonucle-
otides.

REFERENCES

Aaronson, S., et al. Endogenous C-type of BALB/c cells: frequencies of spontaneous and chemical induction, J. Virol. 13:181–185, 1974.

Adam, M. A., et al. J. Virol. 62:3802–3806, 1988.

Albritton, L. M., et al. A putative murine ecotropic retrovirus receptor gene encodes a multiple membrane-spanning protein and confers susceptibility to virus infection. Cell, 57:659–666, 1989.

Anderson, C. Gene therapy researcher under fire over controversial cancer trials. Nature, 360:399–400, 1992.

Anderson, K. P. et al. Endogenous origin of defective retroviruslike particles from a recombinant Chinese hamster ovary cell line. Virology, 181:305–311, 1991.

Anderson, W. F. Human gene therapy. Science, 256:808–813, 1992.

Armentano, D., et al. Effect of internal viral sequences on the utility of retroviral vectors. J. Virol., 62:1647–1650, 1987, Battint, et al. Receptor choice determinants in the envelope glycoproteins of amphotropic, xenotropic, and polytropic murine leukemia viruses. J. Virol., 66:1468–1475, 1992.

Bender, M. A., et al. Evidence that the packaging signal of Moloney murine leukemia virus extends into the gag region. J. Virol., 61:1639–1649, 1987.

Bestwick, R. K., et al. Overcoming interference to retroviral superinfection results in amplified expression and transmission of clones genes. Proc. Natl. Acad. Sci. U.S.A., 85:5404–5408, 1988.

Bird, R. E., et al. Single-chain antigen-binding proteins. Science, 242:423–426, 1988.

Bodine, D. Y., et al. Combination of interleukins 3 and 6 preserves stem cell function in culture and enhances retrovirus-mediated gene transfer into hematopoietic stem cells. Proc. Natl. Acad. Sci. U.S.A., 86:8897–8901, 1989.

Bodine, D. M., et al. Proc. Natl. Acad. Sci., 87:3738–3742, 1990.

Brinkmann, U., et al. B3 (Fv)-PE38KDEL, a single-chain immunotoxin that causes complete regression of a human carcinoma in mice. Proc. Natl. Acad. Sci. U.S.A., 88:8616–8620, 1991.

Brown, D. G., et al. Increased H-2D$^d$ expression following infection by a molecularly cloned ecotropic MuLV. Immunogenetics, 31:94–103, 1990.

Chang, S. M. W., et al. Construction of a defective retrovirus containing the human hypoxanthine phosphoribosyltransferase cDNA and its expression in cultured cells and mouse bone marrow. Mol. Cell. Bio., 7:854–863, 1987.

Chaudhary, V. K., et al. Nature, 339:394, 1989.

Cooper, N. R., et al. Lysis of RNA tumor viruses by human serum: direct antibody-independent triggering of the classical complement pathway. J. Exp. Med., 144:970–985, 1976.

Culver, K. W., et al. In vivo gene transfer with retroviral vector-producer cells for treatment of experimental brain tumors. Science, 256:1550–1152, 1992.

Dalglelsh, A. G., et al. The CD4 (T4) antigen is an essential component of the receptor for the AIDS retrovirus. Nature, 312:763–767, 1984.

Danos, O., et al. Safe and efficient generation of recombinant retroviruses with amphotropic and ecotropic host ranges, Proc. Natl. Acad. Sci. USA., 85:6460–6464, 1988.

Davies, D. R., et al. Ann. Rev. Immunol., 1:87, 1963.

Devereux, J., et al. A comprehensive set of sequence analysis programs for the VAX. Nucleic Acids Res., 12:387–395, 1984.

Dunn, W. A., et al. J. Cell Biol., 102:24, 1986.

Fraenkel, A. E., et al. J. Biol. Response Mod., 4:273, 1985.

Friedmann, T. Progress toward human gene therapy. Science, 244:1275–1281, 1989.

Gallagher, R. E., et al. Oncornavirus lytic activity in the serum of gibbon apes. J. Natl. Cancer Inst., 60:677, 1978.

Ghetie, M. A., et al. Cancer Res., 48:261, 1988.

Gluzman, Y. SV40-transformed simian cells support the replication of early SV40 mutants. Cell, 23:175–182, 1981.

Hartley, J. W., et al. Naturally occurring murine leukemia viruses in wild mice: Characterization of a new "amphotropic" class. J. Virol., 19:19–25, 1976.

Harwood, P. J., et al. Bur. J. Cancer Clin Oncol., 21:1515, 1985.

Heard, J. M., et al. An amino-terminal fragment of the Friend Murine leukemia virus envelope glycoprotein binds the ecotropic receptor. J. Virol., 65:4026–4032, 1991.

Hellstrom, K. E., et al. FASEB J., 3:1715, 1989.

Hendler, F. J., et al. J. Clin. Invest., 74:647, 1984.

Henikoff, S. Unidirectional digestion with exonuclease III in DNA sequence analysis. Method Enz., 155:156, 1987.

Hertler, A. A., et al. J. Biol. Response Mod., 7:97, 1988.

Hesdorffer, C., et al. Somatic gene therapy. Hematology/Oncology Clinics of North America, 5:423–432, 1991.

Hock, R. A., et al. Retrovirus-mediated transfer and expression of drug-resistant genes in human hematopoietic progenitor cells. Nature, 320:275–277, 1986.

Huang et al. J. Virol., 50:417–424, 1384.

Huber, B. E., et al. Retroviral-mediated gene therapy for the treatment of hepatocellular carcinoma: An innovative approach, for cancer therapy. Proc. Natl. Acad. Sci. U.S.A., 83:8039–8043, 1991.

Huston, J. S., et al. Protein engineering of antibody binding sites: Recovery of specific activity in an anti-digoxin single-chain Fv analogue produced in *Escherichia coli*. Proc. Natl. Acad. Sci. U.S.A., 85:5879–5883, 1988.

Jones, N. R., et al. Cancer, 66:152, 1990.

Kawano, T. J., et al. Nature, 332:83, 1988.

Kim, J. W., et al. Transport of cationic amino acids by the mouse retrovirus receptor. Nature, 352:725–729, 1991.

Koch, W., et al. Nucleotide sequence of the env gene of a Friend murine leukemia virus. J. Virol., 45:1–9, 1983.

Kohn, D. B., et al. Genetic Therapy for Genetic Diseases. Cancer Invest., 7:179–192, 1989.

Kurth, R., et al. Recognition of simian sarcoma virus antigen by human sera. In Modern trends in human leukemia (R. Neth et al., eds.), vol. 3, pp. 385–394, Springer, Heidelbezg, 1979.

Landau, N. R., et al. Packaging system for rapid production of murine leukemia virus vectors with variable tropism. J. Virol., 66:5110–5113, 1992.

Lander, R. C., U.S. Pat. No. 4,704,692; 1987.

Lasky, L. A., et al. Neutralization of the AIDS retrovirus by antibodies to a recombinant envelope glycoprotein. Science, 233:209–212, 1986.

Lau, J. L. T., et al. J. Urol., 139:170, 1988.

Lenz, J., et al. Nucleotide sequence of the AKv env gene. J. Virol., 42:519–529, 1982.

Lieber, M. M., et al. Mammalian cells in culture frequently release type C viruses. Science, 182:56–58, 1973.

MacLeod, C. L., et al. Activated T cells express a novel gene on chromosome 8 that is closely related to the murine ecotropic retroviral receptor. Mol. Cell. Biol., 10:3663–3674, 1990.

Manlatis, T., et al. J. Molecular Cloning: A Laboratory Manual. Cold Spring Harbor Laboratory, New York, N.Y., 1982.

Mann, R., et al. Construction of a retrovirus packaging mutant and its use to produce helper-free defective retrovirus. Cell, 33:153–159, 1983.

Markowitz, D., et al. A safe packaging in line for gene transfer: Separating viral genes on two different plasmids. J. Virol., 62:1120–1124, 1988.

Markowitz, D., et al. Construction and use of a safe and efficient-amphotropic packaging cell line. Virol., 167:400–406, 1988a.

Meruelo D., et al. Therapeutic agents with dramatic antiretroviral activity and little toxicity at effective doses: Aromatic polycyclic diones hypericin and pseudohypericin. Proc. Natl. Acad. Sci., 85:5230–5234, 1988.

Miller, A. D., et al. Re-design of retrovirus packaging cell lines to avoid recombination leading to helper virus production. Mol. Cell Biol., 6:2895–2902, 1986.

Miller, A. D., et al. Factors involved in production of helper virus-free retrovirus vectors. Somat. Cell. Mol. Genet., 12:175–183, 1986.

Mueachau, D., et al. Short communications: analysis of retroviral packaging lines for generation of replication-competent virus. Virology, 176:262–265, 1990.

Muraro, R., et al. Cancer Res., 45:5769, 1985.

Murphy, J. R. Cancer Treat. Res., 37::13, 1988.

Murray, M. J., et al. Cell, 25:355–361, 1981.

Neville, D. J. Crit. Rev. Therap. Drug Carrier Syst., 2:329, 1986.

Ogata, M., et al. Proc. Natl. Acad. Sci. U.S.A., 86:4215, 1989.

Ogata, M., et al. J. Immunol., 141:4224, 1988.

O'Hara, B., et al. Characterization of a human gene conferring sensitivity to infection by gibbon ape leukemia virus. Cell Growth Diff., 1:119–127, 1990.

Ott, D., et al. Basis for receptor specificity of non-ecotropic murine leukemia virus surface glycoprotein gp70$^{SU}$. J. Virol., 66:4632–4638, 1992.

Pastan, I., et al. Recombinant Toxins far Cancer Treatment. Science, 254:1173–177, 1991.

Pastan, I., et al. Characterization of monoclonal antibodies B1 and B3 that react with mucinous adenocarcinomas. Cancer Res., 51:3781–3787, 1991.

Pastan, I., et al. J. Biol. Chem., 264:15157, 1989.

Pastan, I., et al. Cell, 47:641, 1986.

Poljak, R. S., et al. Proc. Natl. Acad. Sci. U.S.A., 70:3305, 1973.

Porter, R. R. Science, 180:713, 1973.

Price, J., et al. Lineage analysis in the vertebrate nervous system by retrovirus-mediated gene transfer. Proc. Natl. Acad. Sci., 84:156–160, 1987.

Rasheed, S., et al. Amphotropic host .range of naturally occurring wild mouse leukemia virus. J. Virol., 19:13–18, 1976.

Rein, A., et al. Different recombinant murine Leukemia viruses use different cell surface receptors. Virology, 136:144–152, 1984.

Sambrook, J., et al. In Molecular Cloning: a Laboratory Manual, CSH Press, 1989.

Sanes, J. R., et al. Use of recombinant retrovirus to study post-implantation cell lineage in mouse embryos. EMBO J., 5:3133–3142, 1986.

Sattentau, Q. J., et al. The human and simian immunodeficiency viruses HIV-1, HIV-2 and SIV interact with similar epitopes on their cell surface receptor, the CD4 molecule. AIDS, 2:101–105, 1988.

Scadden, D. T., et al. Human cells infected with retrovirus vectors acquire an endogenous murine provirus. J. Virol., 64:424–427, 1990.

Schiffer, et al. Biochemistry, 12:4620, 1973.

Shih, C. -C., et al. Highly preferred targets for retrovirus integration. Cell, 53:531–537, 1988.

Shinnick, T. M., et al. Nucleotide sequence of Moloney murine leukemia virus. Nature, 293:543–548, 1941.

Simonsen, C. C., et al. Isolation and expression of an altered mouse dihydrofolate reductase cDNA. Proc. Natl. Acad. Sci. USA, 80:2495–2499, 1983.

Skerra, A., et al. Assembly of a functional immunoglobulin Fv fragment in *Escherichia coli*. Science, 240:1038–1041, 1988.

Sommerfelt, M. A., et al. Receptor interference groups of 20 retroviruses plating on human cells. Virology, 176:58–69, 1990.

Sommerfelt, M. A., et al. Human T cell leukemia viruses use a receptor determined by human chromosome 17. Science, 242:1557–1559, 1988.

Sommerfelt, M. A., et al. Localization of the receptor gene for type D simian retroviruses on human chromosome 19. J. Virol., 64:6214–6220, 1990.

Stenback, W. A., et al. Virus particles in hamster tumors as revealed by electron microscopy. Pro:. Soc. Exp. Biol. Med., 122:1219–1223, 1966.

Stoye, J. P., et al. The four classes of endogenous murine leukemia virus: Structural relationships and potential recombination. J. Virol., 61:2859–2669, 1981.

Thompson, L. Science, 258:744–746, 1992.

Thompson, L. Monkey Tests Spark Safety review. Science, 257:1854, 1992.

Urlab, G., et al. Isolation of Chinese hamster cell mutants deficient in dihydrofolate reductase activity. Proc. Natl. Acad. Sci. U.S.A., 77:4216–4220, 1980.

Varkl, N., et al. Cancer Res., 44:681, 1984.

Velu, T. J., et al. Science, 238:1406. 1987.

Verma, I. M., 1990. Gene therapy. Sci. Am., 262:68–84.

Vile, R. G., et al. Virus receptors as permeases. Nature, 352:666–567, 1991.

Vitetta, E. S., et al. Science, 238:1098–177, 1987.

Wahl, R. L., et al. J. Nucl. Med., 24:316, 1983.

Waldemann. Cell. Immunol., 99:53–731, 1986.

Walz, G., et al. Proc. Natl. Acad. Sci. U.S.A., 86:9485, 1989.

Wang, H., et al. Cell-surface receptor for ecotropic murine retroviruses is a basic amino-acid transporter. Nature, 352:729–731, 1991.

Weiss, R., et al. RNA tumor viruses: molecular biology of tumor viruses. Cold Spring Harbor Laboratory, Cold Spring Harbor, N.Y., 1984.

Welsh, R. M., et al. Human serum lyses RNA tumor viruses. Nature, 257:612–614, 1975.

Welsh, R. M., et al. Inactivation and lysis of oncornaviruses by human serum. Virology, 74:432–440, 1976.

Wigler, M., et al. Biochemical transfer of single-copy eucaryotic genes using total cellular DNA as donor. Cell, 14:725–731, 1978.

Williams, D. P., et al. Protein Eng., 1:498, 1987.

Willingham, M. C., et al. Proc. Natl. Acad. Sci. U.S.A., 84:2474, 1987.

Yee, J. -K., et al. Cold Spring Harbor Symp. Quant., Biol., 51:1021, 1986.

Yoshimoto, T., et al. Molecular cloning and characterization of a novel human gene homologous to the murine ecotropic retroviral receptor. Virology, 185:10–17, 1991.

Yoshimoto, T., et al. Identification of Amino acid residues critical for infection with ecotropic murine leukemia retroviruses. Virol., in press, 1993.

Yu, S. -F., et al. Self-inactivating retroviral vectors designed for transfer of whole genes into mammalian cells. Proc. Natl. Acad. Sci. U.S.A., 83:3194–3198, 1986.

---

What is claimed is:

1. A chimeric cellular viral receptor (CVR) for a virus or a virus-based delivery vector, comprising an amino acid sequence of a binding site for a first virus having a first host range, said sequence modified to contain at least one site which binds a second virus having a second host range, wherein said first host range is different from said second host range and wherein, prior to said modification, said amino acid sequence comprises a binding site within amino acids 210–250 of SEQ ID NO:8.

2. The CVR polypeptide according to claim 1, wherein said sequence modification comprises modifying at least a first and second residue of said polypeptide, said first residue being Pro 242of SEQ ID NO:8, which is modified to Tyr and said second residue being an amino acid selected form the group consisting of Val244, Glu239, and Gly 225 of SEQ ID NO:8.

3. The CVR polypeptide according to claim 2, wherein said second residue modification is selected from Gly240 to Val or Val244 to Glu.

4. A chimeric cellular viral receptor (CVR) for a virus or a virus-based delivery vector, comprising an amino acid sequence of a binding site for a first virus having a first host range, said sequence modified to contain at least one site which binds a second virus having a second host range, wherein said first host range is different from said second host range and wherein, prior to said modification, said amino acid sequence has at least 80% homology to the amino acid sequence 210–250 of SEQ ID NO:8.

5. The CVR polypeptide according to claim 4, wherein said homology is at least 95% homology.

6. An isolated or recombinant polypeptide, wherein said polypeptide sequence is SEQ ID NO:8.

* * * * *